US008883798B2

(12) United States Patent
Jansa et al.

(10) Patent No.: US 8,883,798 B2
(45) Date of Patent: Nov. 11, 2014

(54) PYRIMIDINE COMPOUNDS INHIBITING THE FORMATION OF NITRIC OXIDE AND PROSTAGLANDIN E2, METHOD OF PRODUCTION THEREOF AND USE THEREOF

(75) Inventors: Petr Jansa, Lanskroun (CZ); Antonin Holy, Prague (CZ); Ludmila Hola, legal representative, Prague (CZ); Zdenek Zidek, Prague (CZ); Eva Kmonickova, Prague (CZ); Zlatko Janeba, Prague (CZ)

(73) Assignees: Ustav Organicke Chemie a Biochemie Akademie Ved CR, V.V.I., Prague (CZ); Ustav Experimentalni Mediciny Akademie Ved CR, V.V.I., Prague (CZ)

( * ) Notice: Subject to any disclaimer, the term of this patent is extended or adjusted under 35 U.S.C. 154(b) by 0 days.

(21) Appl. No.: 14/000,461

(22) PCT Filed: Feb. 27, 2012

(86) PCT No.: PCT/CZ2012/000020
§ 371 (c)(1),
(2), (4) Date: Aug. 20, 2013

(87) PCT Pub. No.: WO2012/116666
PCT Pub. Date: Sep. 7, 2012

(65) Prior Publication Data
US 2013/0324566 A1 Dec. 5, 2013

(30) Foreign Application Priority Data
Feb. 28, 2011 (CZ) .................................. 2011-103

(51) Int. Cl.
| | | |
|---|---|---|
| *A01N 43/54* | (2006.01) | |
| *C07D 239/42* | (2006.01) | |
| *C07D 401/04* | (2006.01) | |
| *A61K 31/505* | (2006.01) | |
| *C07D 409/04* | (2006.01) | |
| *C07D 239/34* | (2006.01) | |
| *C07D 239/38* | (2006.01) | |
| *C07D 405/04* | (2006.01) | |
| *C07D 239/24* | (2006.01) | |
| *C07D 239/20* | (2006.01) | |
| *C07D 405/14* | (2006.01) | |
| *C07D 401/14* | (2006.01) | |
| *C07D 403/04* | (2006.01) | |
| *A61K 31/506* | (2006.01) | |

(52) U.S. Cl.
CPC ............ *C07D 239/24* (2013.01); *A61K 31/505* (2013.01); *C07D 409/04* (2013.01); *C07D 239/34* (2013.01); *C07D 239/38* (2013.01); *C07D 405/04* (2013.01); *C07D 239/20* (2013.01); *C07D 239/42* (2013.01); *C07D 405/14* (2013.01); *C07D 401/14* (2013.01); *C07D 403/04* (2013.01); *A61K 31/506* (2013.01); *C07D 401/04* (2013.01)
USPC ........................................................ 514/256

(58) Field of Classification Search
CPC .. C07D 239/42; C07D 347/00; A61K 31/506; A61K 31/505
USPC ........................... 544/330, 331, 332; 514/275
See application file for complete search history.

(56) References Cited

U.S. PATENT DOCUMENTS

| | | | |
|---|---|---|---|
| 5,811,428 A | 9/1998 | Suto et al. | |
| 5,917,041 A | 6/1999 | Daluge et al. | |
| 6,271,376 B1 | 8/2001 | Saikali et al. | |
| 2002/0156087 A1 | 10/2002 | Nuss et al. | |
| 2004/0204386 A1 | 10/2004 | Bhatt et al. | |
| 2005/0004149 A1* | 1/2005 | Harada et al. ................ | 514/275 |
| 2006/0142576 A1 | 6/2006 | Meng et al. | |
| 2006/0217390 A1 | 9/2006 | Gunic et al. | |
| 2007/0135437 A1 | 6/2007 | Benjamin et al. | |

FOREIGN PATENT DOCUMENTS

| | | |
|---|---|---|
| EP | 0684236 | 11/1995 |
| EP | 684236 A2 * | 11/1995 |
| EP | 2221053 | 8/2010 |
| WO | WO9513267 | 5/1995 |

(Continued)

OTHER PUBLICATIONS

J.M. Sprague et al., 63 Journal of the American Chemical Society, 3028-3030 (1941).*

(Continued)

*Primary Examiner* — James O Wilson
*Assistant Examiner* — Alexander R Pagano
(74) *Attorney, Agent, or Firm* — Notaro, Michalos & Zaccaria P.C.

(57) ABSTRACT

The invention provides pyrimidine compounds of general formula (I), which reduce simultaneously the production of nitric oxide (NO) and prostaglandin E2 (PGE2). They have no negative effect on the viability of cells in concentrations decreasing the production of these factors by up to 50%; they are not cytotoxic. Furthermore, a method of preparation of the pyrimidine compounds of general formula (I), carrying 2-formamido group, a pharmaceutical composition comprising the substituted pyrimidine compounds according to the invention, and the use of these compounds for the treatment of inflammatory and cancer diseases are provided.

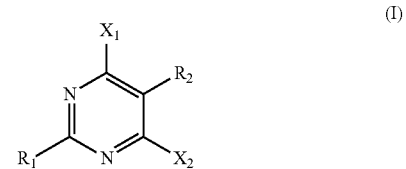

FIG. 7

5 Claims, 6 Drawing Sheets

(56) References Cited

FOREIGN PATENT DOCUMENTS

| WO | WO0006569 | 2/2000 |
|---|---|---|
| WO | WO0019994 | 4/2000 |
| WO | WO 0162233 A2 * | 8/2001 |
| WO | WO03082859 | 10/2003 |
| WO | WO2004009560 | 1/2004 |
| WO | WO2004073594 | 9/2004 |
| WO | WO2005030758 | 4/2005 |
| WO | WO2006079556 | 8/2006 |
| WO | WO2006136442 | 12/2006 |
| WO | WO2007031829 | 3/2007 |
| WO | WO2007084786 | 7/2007 |
| WO | WO 2007098835 A1 * | 9/2007 |
| WO | WO2008067121 | 6/2008 |
| WO | WO2009067081 | 5/2009 |
| WO | WO2009082526 | 7/2009 |
| WO | WO2009095773 | 8/2009 |
| WO | WO2009112461 | 9/2009 |
| WO | WO2010098344 | 9/2010 |
| WO | WO2011015641 | 2/2011 |
| WO | WO2011026835 | 3/2011 |

OTHER PUBLICATIONS

P. B Grove and Merriam-Webster, Inc., Webster's Third New International Dictionary of the English Language, Unabridged (2002).*
Sprague et al., 63 Journal of the American Chemical Society, 3028-3030 (1941).*
F. Cheng et al., 45 European Journal of Medicinal Chemistry, 3459-3471 (2010).*
J. van Veldhoven et al., 16 Bioorganic & Medicinal Chemistry, 2741-2752 (2008).*
Cushing, T.D., et al. "Discov. of a novel series of inhibitors of human cytomega . . . ", Science Direct, Bioorganic & Med. Chem. Letters 16 (2006) 4879-4883, Amgen Inc., CA.
Nishimura, Tamiki et al. "Conformational Analysis of Tandospirone in Aqueous Sol.: Lead Evolution . . . " Bioorganic & Med. Chem. Letters 11 (2001) 1141-1144, Sumitomo Pharm.., JP.
Agarwal, Nidhi, et al., "Chloroprimidines as a New Class of Antimicrobial Agents", Bioorganic & Medicinal Chemistry, Pergamon, GB, vol. 10, No. 4, Apr. 1, 2002, pp. 869-874, Aug. 13, 2014.
Agarwal, Nidhi et al. "Suitably Functionalised Pyrimidines as Potential Antimycotic Agents", Bioorganic & Med. Chem. Letters, Pergamon, Elsevier Science, GB, vol. 16, No. 8, (2000).
Babu, Padavala Ajay, et al., "Identification of Novel CDK2 Inhibitors by QSAR and Virtual Screening Procedures", QSAR & Combin. Science, vol. 27, No. 11-12, Dec. 1, 2008.
Ellsworth, et al., "Discovery of pyrazine carbozamide CB1 antagonists: The introduction of a hydrozyl group . . . ", Bioorganic & Med. Chem., vol. 17, No. 14, Jul. 1, 2007.
Ghosh, Usha, "Estrogenic diazenes: Heterocyclic Non-steroidal Estrogens of Unusual Structure . . . ", Bioorganic & Med. Chem., Pergamon, GB, vol. 11, No. 4, Feb. 1, 2003.
Seela, Frank, et al., "Synthesis of 2'-Deoxyribofuranosides of 8-Aza-7-deazaguanine and Related Pyrazolo[3,4-d]pyrimidines", Helvetica Chimica Acta, vol. 69, No. 7, 1986.
Van Veldhoven, Jacobus, P.D., et al., "A new generation of adenosine receptor antagonists: From di- to trisub . . . ", Bioorganic & Med. Chem., Pergamon, GB, Jan. 12, 2008.

* cited by examiner

Fig. 5
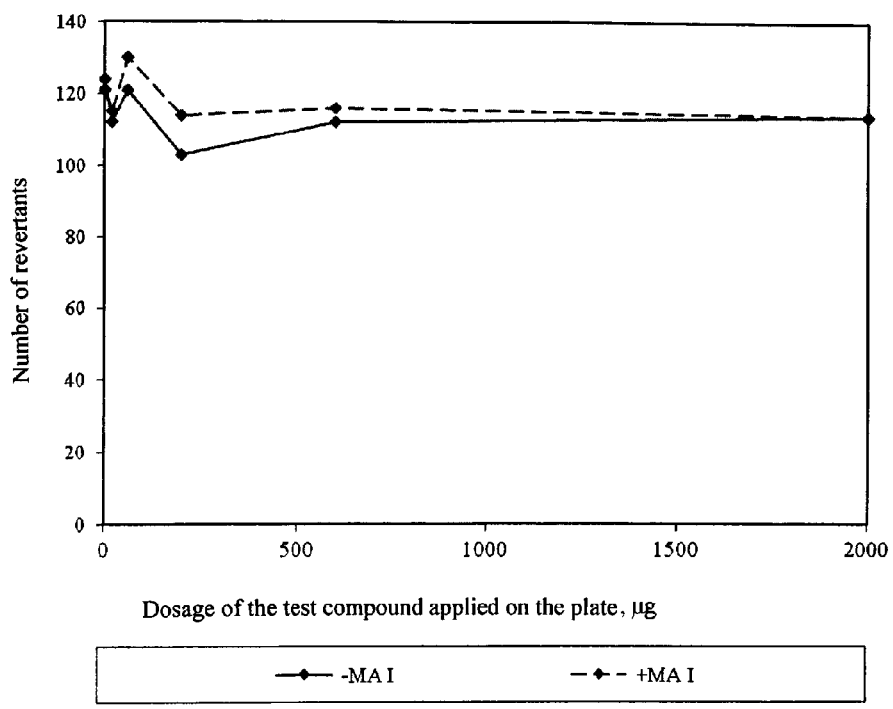
Fig. 6A,B
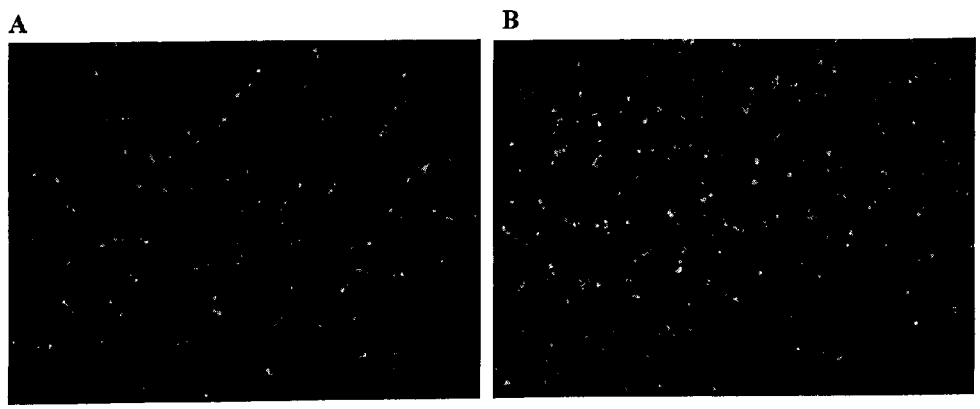

PYRIMIDINE COMPOUNDS INHIBITING THE FORMATION OF NITRIC OXIDE AND PROSTAGLANDIN E2, METHOD OF PRODUCTION THEREOF AND USE THEREOF

FIELD OF ART

The invention concerns polysubstituted pyrimidine derivatives showing the effect of a simultaneous decrease in the production of nitric oxide (NO) and prostaglandin E2 (PGE2) and their use as medicaments.

BACKGROUND ART

The specialized literature provides reliable data that long-term and distinctly elevated concentrations of prostaglandin E2 (PGE2) and nitric oxide (NO) appear with many serious diseases. Although their precise role in the etiopathogenesis of the diseases has not been defined as yet, the experimental and clinical findings so far document that both PGE2 and NO are rightfully the targets in the development of new medicaments.

PGE2 is a biologically active prostanoid produced by a multiple-step enzymatic conversion of arachidonic acid, which is contained in cell membranes. The final and key role in the formation of PGE2 is played by cyclooxygenase-2 (COX-2). Under normal circumstances, the activity of this protein in tissues and cells is negligible. A rapid rise of activity occurs under pathological conditions in reaction to various impulses of biological, chemical or physical nature. Pro-inflammatory cytokines, particularly interleukin-1β (IL-1β), the tumor-necrosis factor (TNF-α) and interferon-γ (IFN-γ) are significant activators [see e.g. Arterioscler. Thromb. Vasc. Biol. 20, 677-682, 2000 and Clin. Exp. Allergy 30, 1275-1284, 2000], as well as infections and UV radiation.

NO is a product of the conversion of the amino acid L-arginine by the enzyme NO synthase (NOS). There are three isoforms of this enzyme. Two of them (endothelial and neuronal NOS; i.e., eNOS and nNOS) produce constitutively very small amounts of NO. Their function is the regulation of the vascular tone and neurotransmission. Inducible NOS (iNOS) is found in almost all cells and tissues of the organism but under normal circumstances does not show any activity. Like in the case of COX-2, iNOS is activated, and consequently a very intensive production of NO occurs, under various pathological conditions, e.g., during hypoxia. The most important iNOS-activity stimulators are bacterial products (lipopolysaccharide, lipoteichoic acid, peptidoglycans) and some cytokines. NO has a fundamental importance in immune protection against viruses, bacteria and other parasites, but the damage of regulation processes resulting from permanent iNOS activation under pathological conditions, and hence from the long-term overproduction of NO, has very adverse consequences for the organism. Increased concentrations cause fatal hypotension and participate in the etiopathogenesis of especially inflammatory and cancerous diseases. Gaseous NO is unstable and easily transformed into toxic products such as peroxynitrite and others. A long-term increase in NO production subsequently leads to DNA damage.

Very effective inhibitors of COX-2 activity are glucocorticoids, which are however strongly immunosuppressive. In practice, both non-selective (ibuprofen, indomethacin) and selective COX-2 inhibitors, e.g., celecoxib, refecoxib, valdecoxib, parecoxib, etoricoxib, lumiracoxib (so-called 'coxibs'), are used. They allow a relatively effective treatment of inflammatory diseases, predominantly of rheumatoid arthritis and osteoarthritis. However, they show undesirable side effects on the cardiovascular system, such as those discovered in rofecoxib, which was the reason for its withdrawal from the pharmaceutical market.

PGE2 is considered to be the cause of pain and fevers related to the process of inflammation. It is assumed that COX-2 activity and the increased PGE2 production play an important role also in the pathogenesis of neurodegenerative diseases with an inflammatory component [J. Mol. Neurosci. 33, 94-99, 2007]. Selective COX-2 inhibitors therefore reduce the risk of Alzheimer's [Brain 131, 651-664, 2008] and Parkinson's diseases and probably also of asthma. Likewise atherosclerosis is connected with the increased levels of PGE2, but in this case the administration of the selective COX-2 inhibitors known so far is not recommended due to the above-mentioned cardiotoxicity, and it is also for this reason that new types of inhibitors are currently being sought [Curr. Drug Targets Cardiovasc. Haematol. Disord. 5, 303-311, 2005].

The inhibition of PGE2 is considered to be one of the very prospective approaches not only with arthritic diseases but also in tumor-disease therapy [W. K. Wu, J. J. Yiu Sung, C. W. Lee, J. Yu, C. H. Cho, Cancer Lett. 2010, electronically published before its publication in print]. The increased activity of the COX-2 enzyme and the excessive production of PGE2 were found in tumors of the large intestine [Gastroenterology 107, 1183-1188, 1994], stomach [Cancer Res. 57, 1276-1280, 1997], lungs [Cancer Res. 58, 3761-3764, 1998] and breast [Int. J. Oncol. 10, 503-507, 1997]. Of the mechanisms which participate in the procancerogenous effect of PGE2, antiapoptic and angiogenic effects have been described [J. Cancer Res. Clin. Oncol. 127, 411-417, 2001]. In connection with a possible antitumor use of the PGE2-production inhibitors, tumors of the large intestine are most often considered [Biochim. Biophys. Acta 1766, 104-119, 2006]; but their applicability may be wider [Oncogene 29, 781-788, 2010]. COX-2 inhibition reduces, e.g., the risk of the formation of non-melanoma skin tumors after UV irradiation [Photochem. Photobiol. 84, 322-329, 2008]. Two of the COX-2 inhibitors, celecoxib and rofecoxib, have been authorized by the FDA as supplements in the standard treatment of patients with familial adenomatous polyposis [Front. Biosci. 9, 2697-2713, 2004].

According to recent, experimentally substantiated, results it is expected that the treatment of inflammatory and cancer diseases is more effective when the PGE2 inhibitors are administered simultaneously with NO inhibitors, although both show antitumor effects already on their own. For instance, the selective COX-2 inhibitor nimesulide and iNOS inhibitor L-NG-nitroarginine reduce the carcinoma of the large intestine in sewer rats [Biofactors 12, 129-133, 2000]. The maximum protective effect against the development of experimental ulcerative colitis in sewer rats was described under simultaneous administration of the COX-2 inhibitor rofecoxib and the iNOS inhibitor aminoguanidine [Inflammopharmacology 15, 188-195, 2007]. The simultaneous inhibitory activity of melatonine on NO and PGE2 production is also considered to be the most likely mechanism of its positive effect on colitis in experimental animals [World J. Gastroenterol. 9, 1307-1311, 2003].

The PGE2 inhibitor (celecoxib) and also selective iNOS inhibitors (aminoguanidine and SC-51) reduce the development of the tumor of large intestine, experimentally induced in sewer rats. The antitumor efficiency distinctly increases when both types of inhibitors are administered at the same time [Cancer Res. 62, 165-170, 2002]. The simultaneous inhibitory effect on NO and PGE2 production is used to explain also the antitumor effects of some substances of natural origin, e.g., obtained from *rubus occidentalis* (blackberry) [Cancer Res. 66, 2853-2859, 2006].

Within the scope of the present invention, it was discovered that novel 5-substituted pyrimidine derivatives are able to provide a dual, or simultaneous, reduction of NO and PGE2 production, and thus they can be used for the treatment of inflammatory and cancer diseases.

Substituted pyrimidines are substances well known from the literature [e.g., the synoptic review: Rewcastle, G. W. Pyrimidines and their Benzo Derivatives; Comprehensive Heterocyclic Chemistry III, 2008, 8, 117-272. Elsevier, Oxford]. For their preparation, 2,4-dihalogenopyrimidines are often used, the halogen atoms of which are subsequently modified by means of a wide range of reactions. These 2,4-dihalogenopyrimidines were studied predominantly as intermediates in the preparation of other substituted pyrimidines, mostly without their biological activity being tested. The antiviral activity of 2-amino-4,6-dichloropyrimidine is known in the literature [Annals of the New York Academy of Sciences 284, 294-304, 1977; Experientia 35(3), 321-322, 1979]. Some works have even dealt with the testing of the anti-inflammatory activities of pyrimidine derivatives, but actual 4,6-dihalogenopyrimidines had been considered to be intermediates only and their biological activity has therefore not been studied [Československá farmacie 10, 433-439, 1986]. Furthermore, the halogen atoms in positions 4 and 6 offer the possibility to prepare the corresponding mono- or diarylpyrimidines using methods described in the literature [Journal of Medicinal Chemistry 50, 2060-2066, 2007; Journal of Heterocyclic Chemistry 46, 960, 2009].

5-Substituted 4,6-dihalogenopyrimidines are very little known from the literature. The exception is 2,5-diamino-4,6-dichloropyrimidine which is abundantly used as an intermediate product in the preparation of purine derivatives [e.g. Nucleosides, Nucleotides & Nucleic Acids, 19(1.2), 297-327, 2000].

The following further examples of the use of 5-substituted pyrimidine derivatives are known from the literature:

1) The compounds of the following formula as glycogen synthase kinase (type 3) inhibitors—this enzyme is one of the main regulating enzymes of glycogen turnover WO 2007/040440]:

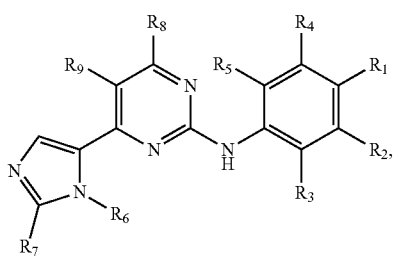

wherein $R_8$ and $R_9$ are only H, CN and halogens.

2) The compounds of the following formula as non-selective inhibitors of the formation of a wide range of cytokines such as TNF-α, IL-1, IL-6, IL-1β, IL-8, IL-12 and as non-selective inhibitors of a wide range of enzymes such as thromboxane-synthase and cyclooxygenase (types 1, 2 and 3):

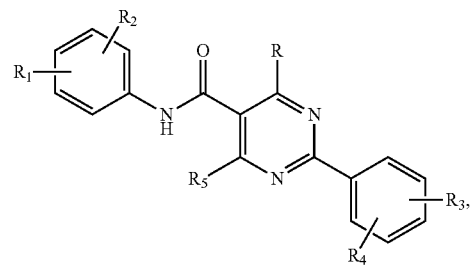

wherein $R_5$ can only be hydrogen, —OH, —$NH_2$, —$N_3$, alkyl, alkyloxy, aryloxy, heteroaryloxy, —$SR_6$, —$S(O)_n$ $R_7$, haloalkyl, aminocycloalkyl, aminoalkyl, aminodialkyl, —$NH(C_1$-$C_5)_nX$, —$NH(CH2)_nOH$, —$NHNH_2$ and alkylhydrazines.

The substances of this formula show a very high toxicity in the concentrations used for determining the production of cytokines [WO 2007/031829] and an essential part of their effect can thus be solely cytocidal effect on the cells of the immunity system. Such substances have practically no therapeutic potential.

3) The compounds of the following formula as strong cancerostatics [WO 2006/079556]. These compounds are highly cytotoxic in nanomolar concentrations:

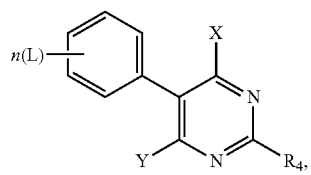

wherein X can only be $NR_1R_2$, OR or SR.

4) The compounds of the following formula as substances stimulating the immunity system through an interaction with the TLR 7 receptor [WO 2009/067081]:

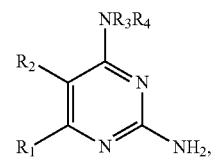

wherein $R_1$ can only be alkyl, alkoxy, alkylthio and wherein $R_3$ is only hydrogen or alkyl.

5) The compounds of the following formula as substances inhibiting a wide range of kinases and phosphatases with a cytotoxic effect for use as cancerostatics [US 2009/0318446]:

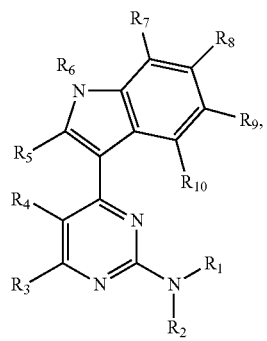

wherein $R_3$ and $R_4$ are any hydrocarbon substituents or OR, COR, COOR, CN, $CONR_1R_2$, $NR_1R_2$, SR, SOR, $SO_2R$, $SO_2NR_1R_2$, R, halogen, $CF_3$, $NO_2$ or an alicyclic substituent. All substances contain an indole ring connected directly to the pyrimidine ring.

6) The compounds of the following formula as substances inhibiting phosphoinositide-3-kinase (PI3Ks) with a cytotoxic effect for use as cancerostatics [WO 2009/120094]:

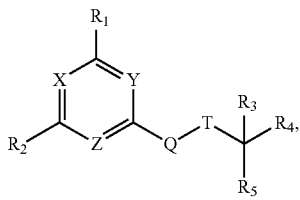

wherein $R_1$ and $R_2$ are independently aryl, heteroaryl or heterocycloalkyl; $R_5$ is only halogen or —$OSO_2R$; Q is any linker; T is only —CO—, —CS—, —$SO_2$—; X, Y and Z are independently nitrogen or CR, R is hydrogen or a lower alkyl.

The necessary pre-requisite for the biological activities of these substances is the presence of the chemically reactive alkylation group T-C—$R_5$.

7) The compounds of the following formula as substances inhibiting (protein-tyrosin)kinase for use as cancerostatics [WO 2006/000420]:

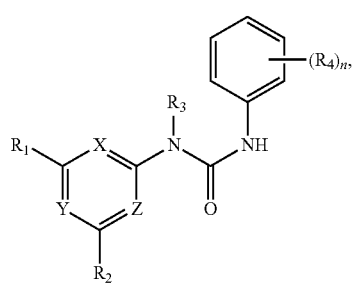

wherein $R_1$, $R_2$, $R_3$, $R_4$ and $R_5$ are almost any substituent; X, Y and Z are independently nitrogen or $CR_5$. Among the substituents X and Y, however, only an arbitrarily substituted phenylaminocarbonylamino group is possible.

8) The compounds of the following formula as substances inhibiting HMG-CoA-reductase, thereby reducing the speed of cholesterol biosynthesis [WO 2005/030758]:

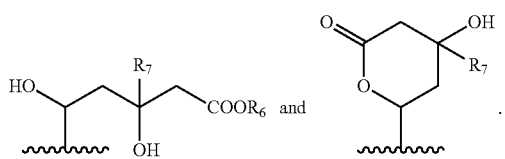

wherein $R_1$, $R_2$, $R_3$ and $R_4$ are almost any substituents; X is nitrogen or $CR_5$; Z can only be fragments corresponding to these formulas:

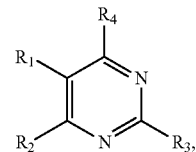

9) The compounds of the following formula as substances inhibiting the production of IL-1, IL-6, IL-8, TNF-α and TNF-β for the treatment of diseases caused by these cytokines [US 2000/006096748]:

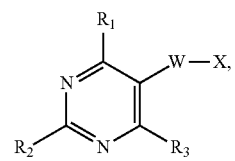

wherein $R_3$ and $R_4$ can only be $NR_5R_6$, $NHS(O)_2R_7$, $NR_{10}C(Z)R_8$, $NR_{10}C(Z)NR_5R_6$, $NR_{10}C(=NR_{11})OR_{10}$ or $NR_{10}C(Z)NR_5R_6$.

10) The compounds of the following formula as stimulators of the production of a nerve-growth factor for the treatment of neurodegenerative diseases [WO 99/19305]:

wherein $R_1$ can only be an amino group substituted by one or two alkyl residues, which may be further substituted. These alkyl residues may even jointly form a ring, but this ring can only be heterocycloalkyl.

11) The compounds of the following formula for use as cancerostatics [CA 2093203]:

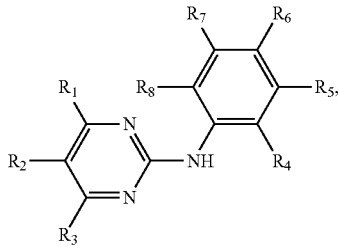

wherein R$_2$ and R$_3$ can only be hydrogen or a lower alkyl.

12) The compounds of the following formula as inhibitors of transcription factor activation (such as NF-κB and AP-1) for use as anti-inflammatory medicaments [U.S. Pat. No. 5,811,428]:

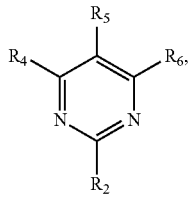

wherein R$_2$, R$_4$ and R$_6$ are almost any substituents and R$_5$ can only be —C(O)NR$_a$R$_b$, —C(S)NR$_a$R$_b$, —NR$_a$C(O)R$_b$ and —NR$_a$C(S)R$_b$.

These substances inhibit the production of a wide range of cytokines and other signal molecules, such as IL-1, IL-2, IL-8, TNF-α, TAP-1, MHC, E-selectin, VCAM-1, ICAM-1, c-mys, ras and p53. These factors (NF-κB and AP-1) also have further natural biological functions such as the participation of NF-κB in the transfer of the nerve signal (synaptic plasticity) or memory storage [Synapse 35 (2), 151-159, 2000]. The above-mentioned substances with a non-selective effect have little therapeutic potential.

DISCLOSURE OF THE INVENTION

A first aspect of the invention is polysubstituted pyrimidine compounds of general formula I,

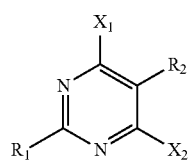

(I)

wherein
X$_1$ is selected from a group comprising —Cl, —Br, —I, aryl, heteroaryl, whereas the aromatic ring of the substituents aryl and heteroaryl is bound directly to the pyrimidine ring;
X$_2$ is selected from a group comprising —Cl, —Br, —I, aryl, heteroaryl, whereas the aromatic ring of the substituents aryl and heteroaryl is bound directly to the pyrimidine ring;
R$_1$ is selected from a group comprising —H, —NH$_2$, —OH, —SH, —NHNH$_2$, alkyl, alkenyl, alkynyl, cycloalkyl, cycloalkenyl, aryl, heteroaryl;
R$_2$ is selected from a group comprising halogen, —NH$_2$, —OH, —NHNH$_2$, —NO, —NO$_2$, —N$_3$, —SH, —SO$_3$H, —SO$_2$NH$_2$, —SCN, alkyl, alkenyl, alkynyl, cycloalkyl, cycloalkenyl, aryl, heteroaryl and phosphono;
wherein
alkyl is a linear or branched C$_1$-C$_{10}$, preferably C$_2$-C$_6$, most preferably C$_3$-C$_5$ alkyl chain, in which any —CH$_2$— group can optionally be replaced by —O—, —S— or —NR$_c$— group, wherein R$_c$ is H or a group selected from alkyl, alkenyl, alkynyl, cycloalkyl, cycloalkenyl, aryl, heteroaryl as defined herein, whereas alkyl can be unsubstitued or substitued by 1 to 5 substituents selected from a group comprising —OH, —SH, =O, =NH, =S, ≡N, halogen, aryl, heteroaryl, —NH$_2$, —CN, —NO$_2$, —COOR$_d$, wherein R$_d$ is H or C$_1$-C$_6$ alkyl;
alkenyl is a linear or branched C$_2$-C$_{10}$, preferably C$_2$-C$_6$, most preferably C$_3$-C$_5$ hydrocarbon chain comprising at least one double bond, wherein any —CH$_2$— group can optionally be replaced by —O—, —S— or —NR$_e$— group, wherein R$_e$ is H or a group selected from a group comprising alkyl, alkenyl, alkynyl, cycloalkyl, cycloalkenyl, aryl, heteroaryl as defined herein and any =CH— group can optionally be replaced by =N— group, whereas the alkenyl can be unsubstituted or substituted by 1-5 substituents selected from a group comprising —OH, —SH, =O, =NH, =S, ≡N, halogen, —NH$_2$, aryl, heteroaryl, —CN, —NO$_2$, and —COOR$_f$, wherein R$_f$ is H or C$_1$-C$_6$ alkyl;
alkynyl is a linear or branched C$_2$-C$_{10}$, preferably C$_2$-C$_6$, most preferably C$_3$-C$_5$ hydrocarbon chain comprising at least one triple bond, which can optionally comprise also a double bond, whereas in this hydrocarbon chain any —CH$_2$— group can optionally be replaced by —O—, —S— or —NR$_g$— group, wherein R$_g$ is H or a substituent selected from a group comprising alkyl, alkenyl, alkynyl, cycloalkyl, cycloalkenyl, aryl, heteroaryl as defined herein and any =CH— group can optionally be replaced by =N— group, whereas the alkynyl can be unsubstituted or substituted by 1-5 substituents selected from a group comprising —OH, —SH, =O, =NH, =S, ≡N, halogen, —NH$_2$, —CN, —NO$_2$, aryl, heteroaryl and —COOR$_h$, wherein R$_h$ is H or C$_1$-C$_6$ alkyl;
cycloalkyl is a linear or branched C$_3$-C$_{10}$, preferably C$_3$-C$_8$, most preferably C$_5$-C$_8$ hydrocarbon chain comprising at least one cycle, in which any —CH$_2$— group can optionally be replaced by —O—, —S— or —NR$_i$— group, wherein R$_i$ is H or a substituent selected from a group comprising alkyl, alkenyl, alkynyl, cycloalkyl, cycloalkenyl, aryl, heteroaryl as defined herein, whereas the cycloalkyl can be unsubstituted or substituted by 1-5 substituents selected from a group comprising —OH, —SH, =O, =NH, =S, ≡N, halogen, —NH$_2$, —CN, —NO$_2$, aryl, heteroaryl and —COOR$_j$, where R$_j$ is H or C$_1$-C$_6$ alkyl;
cycloalkenyl is a linear or branched C$_4$-C$_{10}$, preferably C$_4$-C$_8$, most preferably C$_5$-C$_8$ hydrocarbon chain comprising at least one double bond and at least one cycle, in which any —CH$_2$— group can optionally be replaced by —O—, —S— or —NR$_k$— group, wherein R$_k$ is H or a substituent selected from a group comprising alkyl, alkenyl, alkynyl, cycloalkyl, cycloalkenyl, aryl, heteroaryl as defined herein, and any =CH— group can optionally be replaced by =N— group, whereas the cycloalkenyl can be unsubstituted or substituted by 1-5 substituents selected from a group comprising —OH, —SH, =O, =NH, =S, ≡N, halogen, —NH₂, —CN, —NO₂, aryl, heteroaryl and —COOR$_m$, wherein R$_m$ is H or C$_1$-C$_6$ alkyl;

alkoxy is a group —OR$_a$, wherein R$_a$ is a group selected from a group comprising alkyl, alkenyl, alkynyl, cycloalkyl, cycloalkenyl as defined above;

alkylthio is a group —SR$_b$, wherein R$_b$ is a group selected from a group comprising alkyl, alkenyl, alkynyl, cycloalkyl, cycloalkenyl as defined above;

aryl is a hydrocarbon group comprising 6-14 carbon atoms, preferably 6-12 carbon atoms, and comprising at least one aromatic cycle, whereas the aryl can be unsubstituted or substituted by 1-5 substituents selected from a group comprising —OH, —SH, =O, =NH, =S, ≡N, halogen, C$_1$-C$_6$ alkyl, C$_1$-C$_6$ alkoxy, C$_1$-C$_6$ alkylthio, —NH₂, —CN, —NO₂, and —COOR$_n$, wherein is R$_n$ or C$_1$-C$_6$ alkyl; aryl is preferably selected from a group comprising phenyl, benzyl, naphthyl;

heteroaryl is a hydrocarbon group comprising 2-14 carbon atoms, preferably 4-10 carbon atoms and at least one heteroatom, preferably 1-2 heteroatoms selected from a group comprising O, S, N, and comprising at least one aromatic cycle; preferably the heteroaryl is selected from pyrrolyl, furanyl, thiophenyl, imidazolyl, thiazolyl, oxazolyl, indolyl and pyridinyl; whereas the heteroaryl can be unsubstituted or substituted by 1-5 substituents selected from a group comprising —OH, —SH, =O, =NH, =S, ≡N, halogen, C$_1$-C$_6$ alkyl, C$_1$-C$_6$ alkoxy, C$_1$-C$_6$ alkylthio, —NH₂, —CN, NO₂, and —COOR$_p$, wherein R$_p$ is H or C$_1$-C$_6$ alkyl;

halogen is selected from a group comprising —F, —Cl, —Br, —I;

phosphono is a group comprising 0 až 8 carbon atoms, —P(O)OR$_w$OR$_x$, where R$_w$ and R$_x$ are the same or different groups selected from a group comprising H, alkyl, alkenyl, alkynyl, cycloalkyl, cycloalkenyl, aryl or heteroaryl as defined above;

provided that:
1) X$_1$ and/or X$_2$ are not unsubstituted or substituted indole bound directly to the pyrimidine ring by the position 3 of the indole ring; or
2) R$_2$ is not selected from arbitrarily substituted phenyl bound directly to the pyrimidine ring, from the groups —C(O)NR$_a$R$_b$, —C(S)NR$_a$R$_b$, —NR$_a$C(O)R$_b$ and —NR$_a$C(S)R$_b$, wherein R$_a$ and R$_b$ are any substituents, R$_2$ is not the group —CN, and R2 is not selected from the following groups:

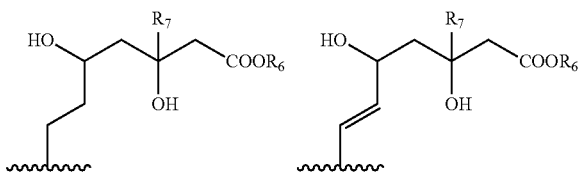

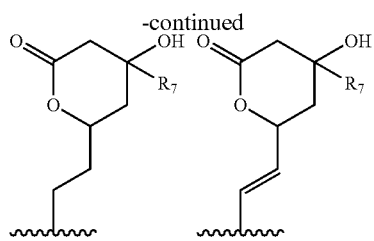

wherein R$_6$ and R$_7$ is any substituent; or
3) R$_1$ is not the substituent -Q-T-C—R$_5$, wherein R$_5$ is halogen or —OSO₂R; Q is any linker; T is solely —CO—, —CS—, —SO₂— and C is arbitrarily substituted carbon, and R$_1$ is not an arbitrarily substituted phenylaminocarbonylamino group;

or their pharmaceutically acceptable salts, for use as medicaments.

The substituted pyrimidine derivatives according to the present invention effectively reduce NO and prostaglandin E2 (PGE2) production. This dual effect makes them suitable mainly for the treatment of diseases which are induced or the severity of which is potentiated by overproduction of NO and/or prostaglandin E2. Such diseases are mainly, but not exclusively, inflammatory and cancer diseases.

Another aspect of the present invention are the polysubstituted pyrimidine compounds of the general formula I for use as dual inhibitors of NO and prostaglandin E2 production.

The pharmaceutically acceptable salts include salts with alkali metals, salts with inorganic or organic anions, salts with inorganic or organic cations and addition salts with inorganic or organic acids or bases, as well as other salts suitable for pharmaceutical administration.

R$_1$ is preferably selected from the group comprising NH₂, formamido (formylamino), dimethylamino, [(dimethylamino)methylene]amino, OH, SH, C$_1$-C$_6$ alkoxy, C$_1$-C$_6$ alkylthio, C$_1$-C$_6$ alkyl, hydrogen.

X$_1$ and X$_2$ are preferably selected independently from the group comprising halogen, phenyl, pyridyl, furanyl, thiophenyl, pyrrolyl, imidazolyl, benzofuranyl, benzothienyl, naphthyl, wherein the aromatic and heteroaromatic groups can optionally be substituted by one or more substituents selected from halogen, C$_1$-C$_6$ alkoxy and NO₂.

Preferably, R$_2$ is selected from the group comprising C$_1$-C$_6$ alkyl, C$_2$-C$_6$ alkenyl, C$_2$-C$_6$ alkynyl, NH₂, phenyl, benzyl, wherein these groups can optionally be substituted by one or more substituents selected from the group comprising halogen, NO₂, C$_1$-C$_6$ alkoxy.

In a preferred embodiment, the pyrimidine compounds of general formula I can contain at least one deuterium atom, i.e., at least one substituent can be deutered, or perdeutered.

More preferably, the invention relates to the following compounds of the general formula I:

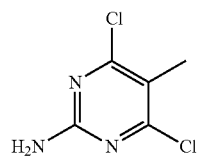

2-amino-4,6-dichloro-5-methylpyrimidine

-continued
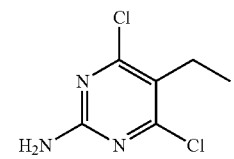 2-amino-4,6-dichloro-5-ethylpyrimidine
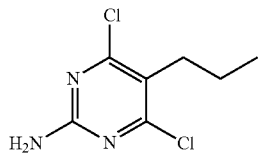 2-amino-4,6-dichloro-5-propylpyrimidine
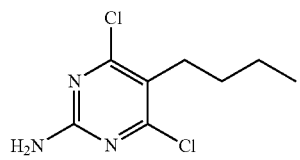 2-amino-5-butyl-4,6-dichloropyrimidine
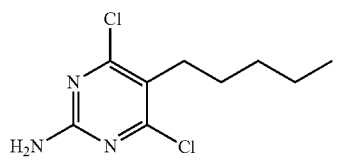 2-amino-4,6-dichloro-5-pentylpyrimidine
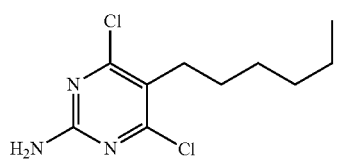 2-amino-4,6-dichloro-5-hexylpyrimidine
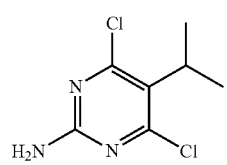 2-amino-4,6-dichloro-5-isopropylpyrimidine
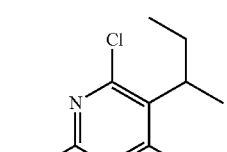 2-amino-5-(sec-butyl)-4,6-dichloropyrimidine
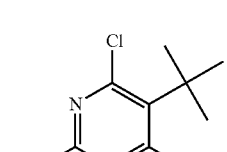 2-amino-5-(tert-butyl)-4,6-dichloropyrimidine
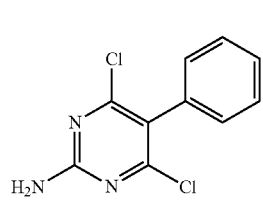 2-amino-4,6-dichloro-5-phenylpyrimidine

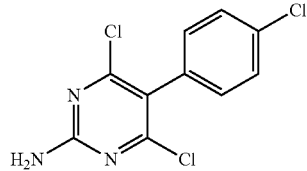 [SMILES: Nc1nc(Cl)c(-c2ccc(Cl)cc2)c(Cl)n1] 2-amino-4,6-dichloro-5-(4-chlorophenyl)pyrimidine
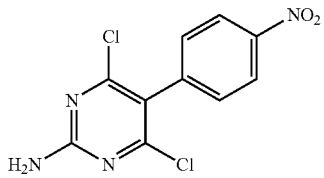 [SMILES: Nc1nc(Cl)c(-c2ccc([N+](=O)[O-])cc2)c(Cl)n1] 2-amino-4,6-dichloro-5-(4-nitrophenyl)pyrimidine
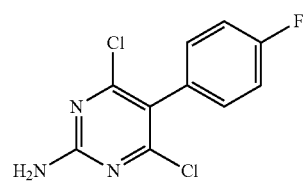 2-amino-4,6-dichloro-5-(4-fluorophenyl)pyrimidine
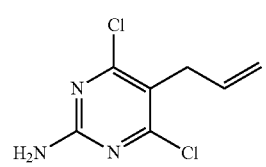 5-allyl-2-amino-4,6-dichloropyrimidine
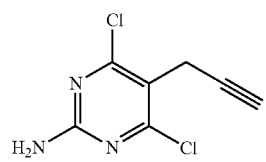 2-amino-4,6-dichloro-5-(prop-2-yn-1-yl)pyrimidine
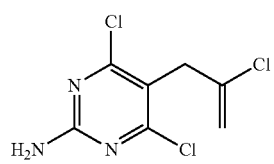 2-amino-4,6-dichloro-5-(2-chloroallyl)pyrimidine
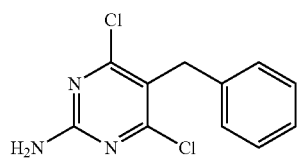 2-amino-5-benzyl-4,6-dichloropyrimidine
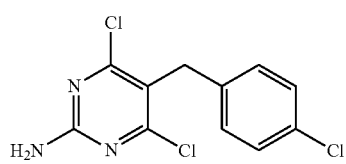 [SMILES: Nc1nc(Cl)c(Cc2ccc(Cl)cc2)c(Cl)n1] 2-amino-4,6-dichloro-5-(4-chlorobenzyl)pyrimidine
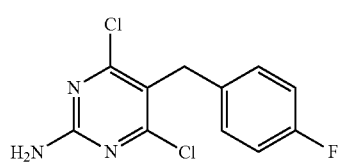 [SMILES: Nc1nc(Cl)c(Cc2ccc(F)cc2)c(Cl)n1] 2-amino-4,6-dichloro-5-(4-fluorobenzyl)pyrimidine -continued
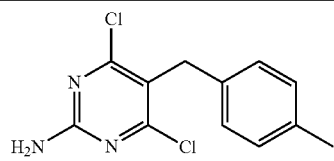 2-amino-4,6-dichloro-5-(4-methylbenzyl)pyrimidine
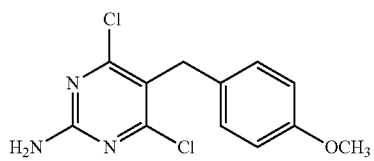 [SMILES: COc1ccc(Cc2c(Cl)nc(N)nc2Cl)cc1] 2-amino-4,6-dichloro-5-(4-methoxybenzyl)pyrimidine
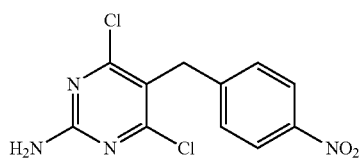 [SMILES: Nc1nc(Cl)c(Cc2ccc([N+](=O)[O-])cc2)c(Cl)n1] 2-amino-4,6-dichloro-5-(4-nitrobenzyl)pyrimidine
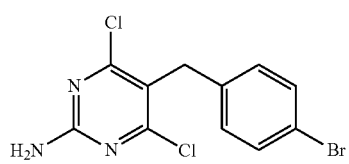 [SMILES: Nc1nc(Cl)c(Cc2ccc(Br)cc2)c(Cl)n1] 2-amino-5-(4-bromobenzyl)-4,6-dichloropyrimidine
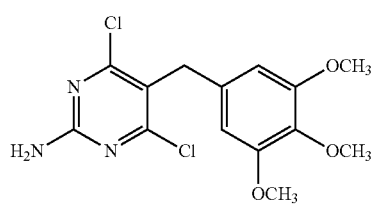 2-amino-4,6-dichloro-5-(3,4,5-trimethoxybenzyl)pyrimidine
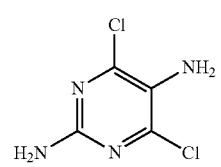 2,5-diamino-4,6-dichloropyrimidine
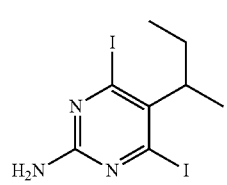 2-amino-5-sec-butyl-4,6-diiodopyrimidine
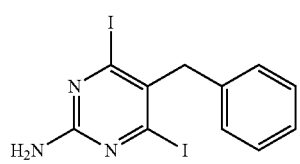 [SMILES: Nc1nc(I)c(Cc2ccccc2)c(I)n1] 2-amino-5-benzyl-4,6-diiodopyrimidine
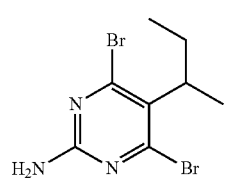 2-amino-4,6-dibromo-5-sec-butylpyrimidine -continued
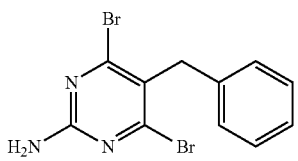 [SMILES: Nc1nc(Br)c(Cc2ccccc2)c(Br)n1]
2-amino-5-benzyl-4,6-dibromopyrimidine
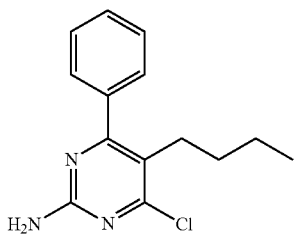 [SMILES: CCCCc1c(Cl)nc(N)nc1-c1ccccc1]
2-amino-5-butyl-4-chloro-6-phenylpyrimidine
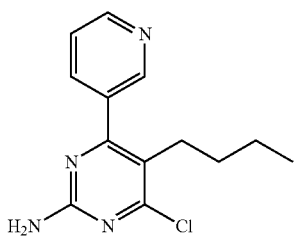 [SMILES: CCCCc1c(Cl)nc(N)nc1-c1cccnc1]
2-amino-5-butyl-4-chloro-6-(pyridin-3-yl)pyrimidine
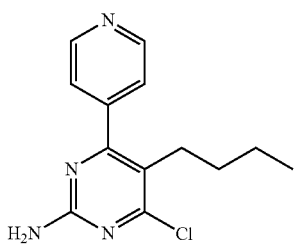 [SMILES: CCCCc1c(Cl)nc(N)nc1-c1ccncc1]
2-amino-5-butyl-4-chloro-6-(pyridin-4-yl)pyrimidine
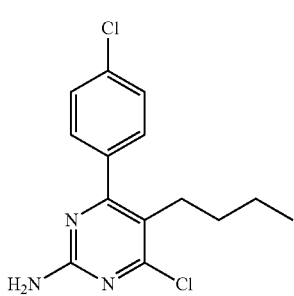 [SMILES: CCCCc1c(Cl)nc(N)nc1-c1ccc(Cl)cc1]
2-amino-5-butyl-4-chloro-6-(4-chlorophenyl)pyrimidine
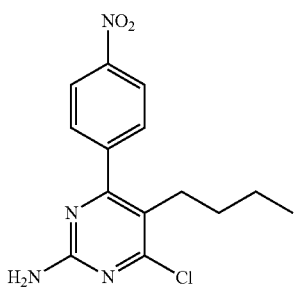
2-amino-5-butyl-4-chloro-6-(4-nitrophenyl)pyrimidine

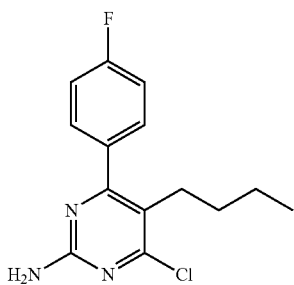
2-amino-5-butyl-4-chloro-6-(4-fluorophenyl)pyrimidine
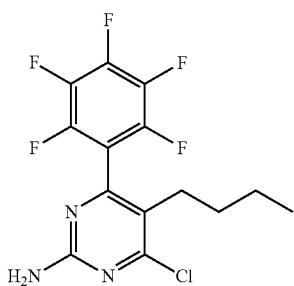 [SMILES: CCCCc1c(Cl)nc(N)nc1-c1c(F)c(F)c(F)c(F)c1F]
2-amino-5-butyl-4-chloro-6-(perfluorophenyl)pyrimidine
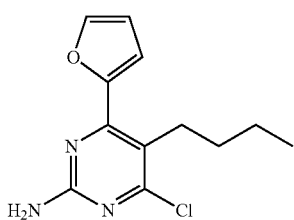 [SMILES: CCCCc1c(Cl)nc(N)nc1-c1ccco1]
2-amino-5-butyl-4-chloro-6-(furan-2-yl)pyrimidine
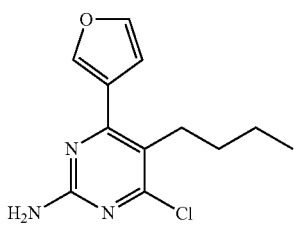 [SMILES: CCCCc1c(Cl)nc(N)nc1-c1ccoc1]
2-amino-5-butyl-4-chloro-6-(furan-3-yl)pyrimidine
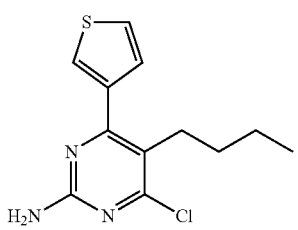
2-amino-5-butyl-4-chloro-6-(thiophen-3-yl)pyrimidine
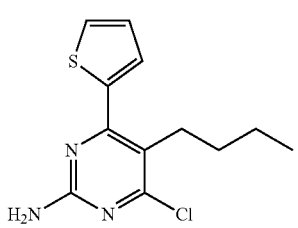
2-amino-5-butyl-4-chloro-6-(thiophen-2-yl)pyrimidine -continued
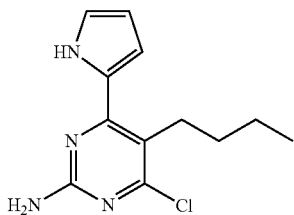 [SMILES: CCCCc1c(Cl)nc(N)nc1-c1ccc[nH]1]
2-amino-5-butyl-4-chloro-6-(1H-pyrrol-2-yl)pyrimidine
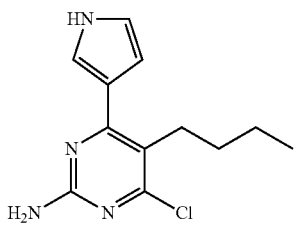 [SMILES: CCCCc1c(Cl)nc(N)nc1-c1cc[nH]c1]
2-amino-5-butyl-4-chloro-6-(1H-pyrrol-3-yl)pyrimidine
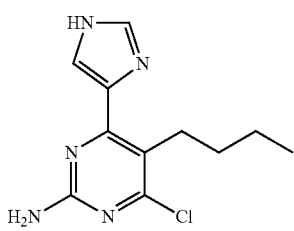 [SMILES: CCCCc1c(Cl)nc(N)nc1-c1c[nH]cn1]
2-amino-5-butyl-4-chloro-6-(1H-imidazol-4-yl)pyrimidine
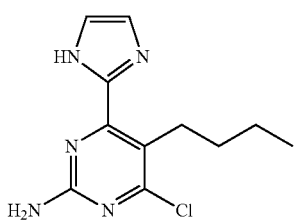
2-amino-5-butyl-4-chloro-6-(1H-imidazol-2-yl)pyrimidine
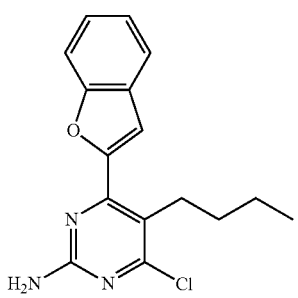 [SMILES: CCCCc1c(Cl)nc(N)nc1-c1cc2ccccc2o1]
2-amino-4-(benzofuran-2-yl)-5-butyl-6-chloropyrimidine
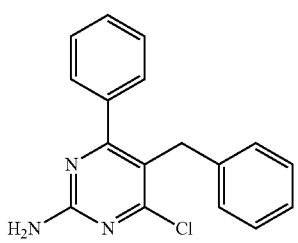 [SMILES: Nc1nc(Cl)c(Cc2ccccc2)c(-c2ccccc2)n1]
2-amino-5-benzyl-4-chloro-6-phenylpyrimidine -continued
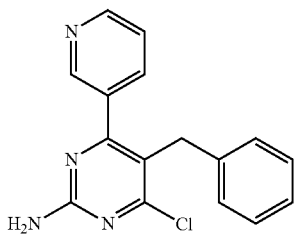 [SMILES: Nc1nc(Cl)c(Cc2ccccc2)c(-c2cccnc2)n1]
2-amino-5-benzyl-4-chloro-6-(pyridin-3-yl)pyrimidine
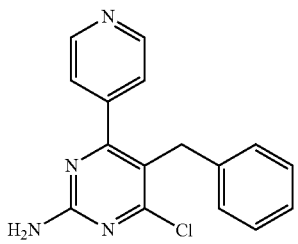 [SMILES: Nc1nc(Cl)c(Cc2ccccc2)c(-c2ccncc2)n1]
2-amino-5-benzyl-4-chloro-6-(pyridin-4-yl)pyrimidine
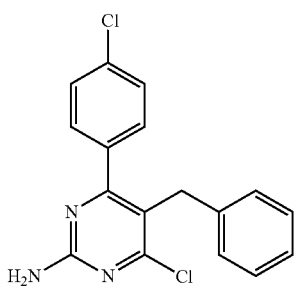 [SMILES: Nc1nc(Cl)c(Cc2ccccc2)c(-c2ccc(Cl)cc2)n1]
2-amino-5-benzyl-4-chloro-6-(4-chlorophenyl)pyrimidine
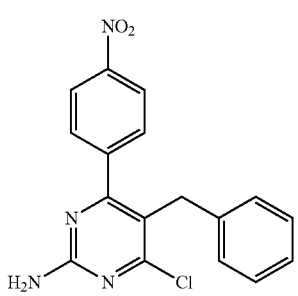 [SMILES: Nc1nc(Cl)c(Cc2ccccc2)c(-c2ccc([N+](=O)[O-])cc2)n1]
2-amino-5-benzyl-4-chloro-6-(4-nitrophenyl)pyrimidine
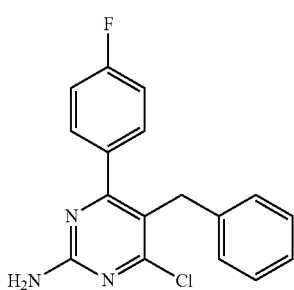
2-amino-5-benzyl-4-chloro-6-(4-fluorophenyl)pyrimidine

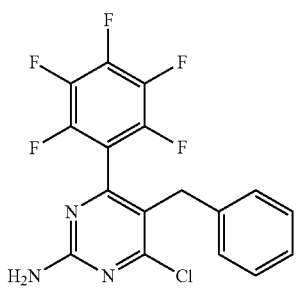 [SMILES: Nc1nc(Cl)c(Cc2ccccc2)c(-c2c(F)c(F)c(F)c(F)c2F)n1]
2-amino-5-benzyl-4-chloro-6-(perfluorophenyl)pyrimidine
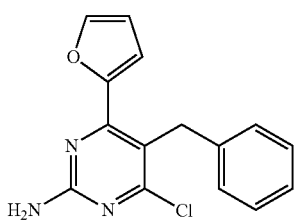 [SMILES: Nc1nc(Cl)c(Cc2ccccc2)c(-c2ccco2)n1]
2-amino-5-benzyl-4-chloro-6-(furan-2-yl)pyrimidine
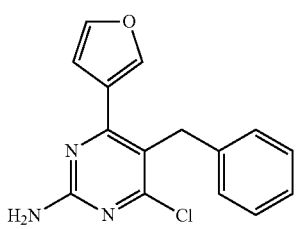 [SMILES: Nc1nc(Cl)c(Cc2ccccc2)c(-c2ccoc2)n1]
2-amino-5-benzyl-4-chloro-6-(furan-3-yl)pyrimidine
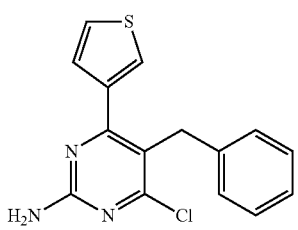 [SMILES: Nc1nc(Cl)c(Cc2ccccc2)c(-c2ccsc2)n1]
2-amino-5-benzyl-4-chloro-6-(thiophen-3-yl)pyrimidine
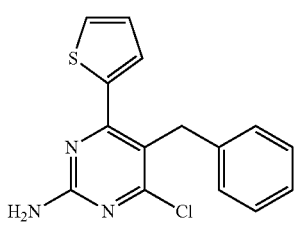 [SMILES: Nc1nc(Cl)c(Cc2ccccc2)c(-c2cccs2)n1]
2-amino-5-benzyl-4-chloro-6-(thiophen-2-yl)pyrimidine
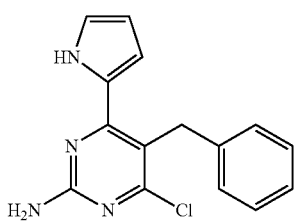
2-amino-5-benzyl-4-chloro-6-(1H-pyrrol-2-yl)pyrimidine -continued
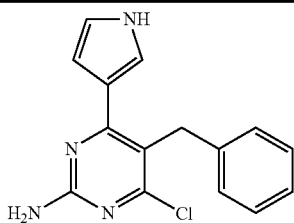
2-amino-5-benzyl-4-chloro-6-(1H-pyrrol-3-yl)pyrimidine
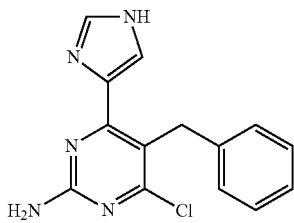 [SMILES: Nc1nc(Cl)c(Cc2ccccc2)c(-c2c[nH]cn2)n1]
2-amino-5-benzyl-4-chloro-6-(1H-imidazol-4-yl)pyrimidine
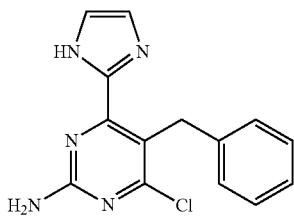 [SMILES: Nc1nc(Cl)c(Cc2ccccc2)c(-c2ncc[nH]2)n1]
2-amino-5-benzyl-4-chloro-6-(1H-imidazol-2-yl)pyrimidine
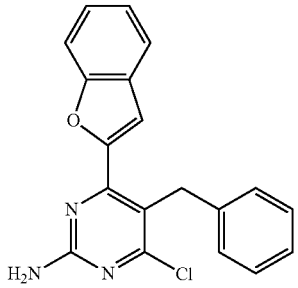 [SMILES: Nc1nc(Cl)c(Cc2ccccc2)c(-c2cc3ccccc3o2)n1]
2-amino-4-(benzofuran-2-yl)-5-benzyl-6-chloropyrimidine
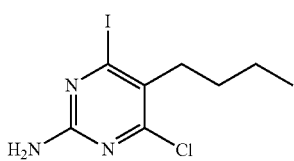
2-amino-5-butyl-4-chloro-6-iodopyrimidine
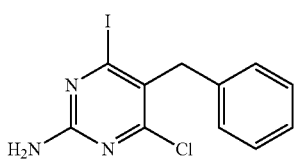 [SMILES: Nc1nc(Cl)c(Cc2ccccc2)c(I)n1]
2-amino-5-benzyl-4-chloro-6-iodopyrimidine
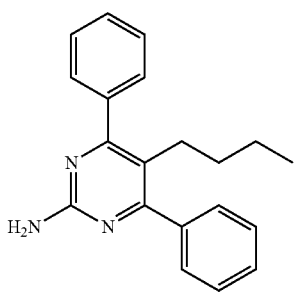 [SMILES: CCCCc1c(-c2ccccc2)nc(N)nc1-c1ccccc1]
2-amino-5-butyl-4,6-diphenylpyrimidine

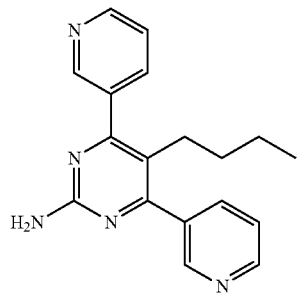 [SMILES: CCCCc1c(-c2cccnc2)nc(N)nc1-c1cccnc1]
2-amino-5-butyl-4,6-bis(pyridin-3-yl)pyrimidine
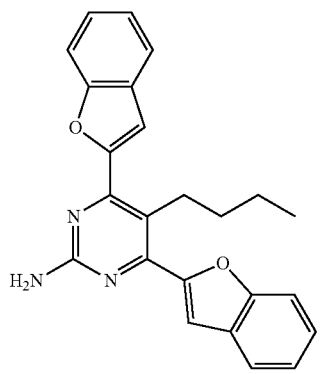 [SMILES: CCCCc1c(-c2cc3ccccc3o2)nc(N)nc1-c1cc2ccccc2o1]
2-amino-4,6-bis(benzofuran-2-yl)-5-butylpyrimidine
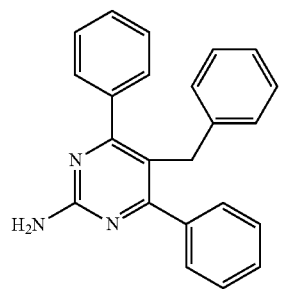 [SMILES: Nc1nc(-c2ccccc2)c(Cc2ccccc2)c(-c2ccccc2)n1]
2-amino-5-benzyl-4,6-diphenylpyrimidine
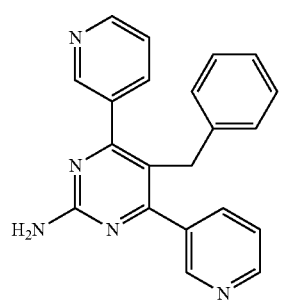 [SMILES: Nc1nc(-c2cccnc2)c(Cc2ccccc2)c(-c2cccnc2)n1]
2-amino-5-benzyl-4,6-bis(pyridin-3-yl)pyrimidine
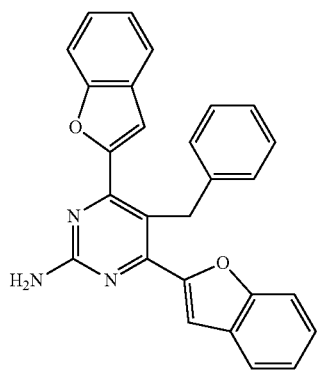 [SMILES: Nc1nc(-c2cc3ccccc3o2)c(Cc2ccccc2)c(-c2cc3ccccc3o2)n1]
2-amino-4,6-bis(benzofuran-2-yl)-5-benzylpyrimidine

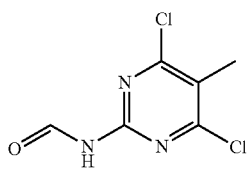 4,6-dichloro-2-formamido-5-methylpyrimidine

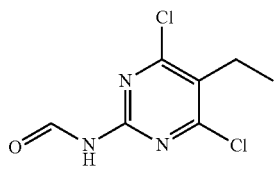 4,6-dichloro-5-ethyl-2-formamidopyrimidine

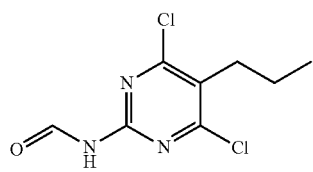 4,6-dichloro-2-formamido-5-propylpyrimidine

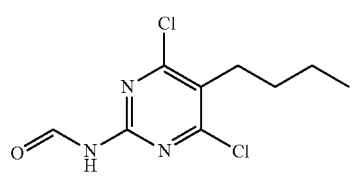 5-butyl-4,6-dichloro-2-formamidopyrimidine

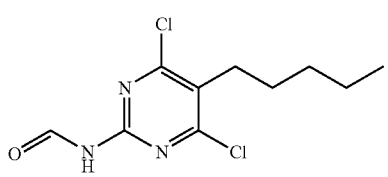 [SMILES: CCCCCc1c(Cl)nc(NC=O)nc1Cl] 4,6-dichloro-2-formamido-5-pentylpyrimidine

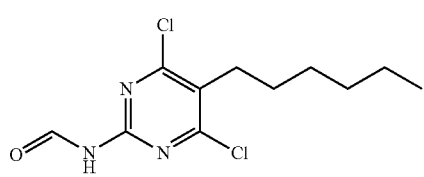 [SMILES: CCCCCCc1c(Cl)nc(NC=O)nc1Cl] 4,6-dichloro-2-formamido-5-hexylpyrimidine

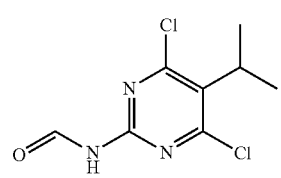 4,6-dichloro-2-formamido-5-isopropylpyrimidine

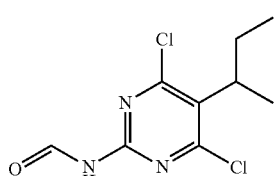 5-(sec-butyl)-4,6-dichloro-2-formamidopyrimidine

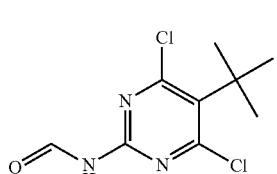 5-(tert-butyl)-4,6-dichloro-2-formamidopyrimidine

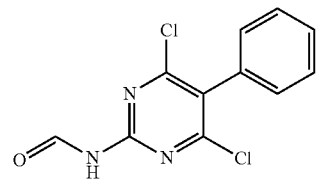 [SMILES: O=CNc1nc(Cl)c(-c2ccccc2)c(Cl)n1] 4,6-dichloro-2-formamido-5-phenylpyrimidine
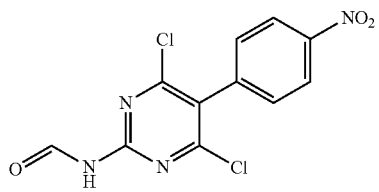 [SMILES: O=CNc1nc(Cl)c(-c2ccc([N+](=O)[O-])cc2)c(Cl)n1] 4,6-dichloro-2-formamido-5-(4-nitrophenyl)pyrimidine
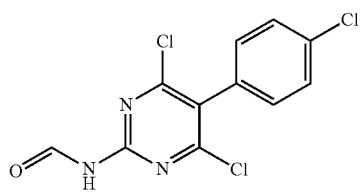 [SMILES: O=CNc1nc(Cl)c(-c2ccc(Cl)cc2)c(Cl)n1] 4,6-dichloro-5-(4-chlorophenyl)-2-formamidopyrimidine
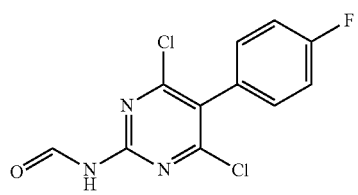 [SMILES: O=CNc1nc(Cl)c(-c2ccc(F)cc2)c(Cl)n1] 4,6-dichloro-5-(4-fluorophenyl)-2-formamidopyrimidine
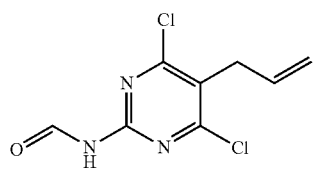 5-allyl-4,6-dichloro-2-formamidopyrimidine
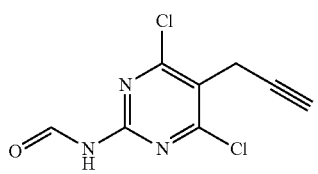 4,6-dichloro-2-formamido-5-(prop-2-yn-1-yl)pyrimidine
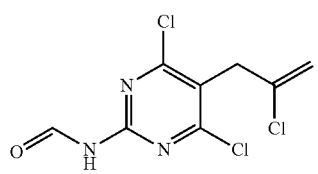 4,6-dichloro-5-(2-chloroallyl)-2-formamidopyrimidine
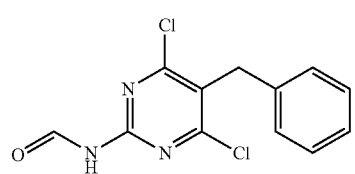 [SMILES: O=CNc1nc(Cl)c(Cc2ccccc2)c(Cl)n1] 5-benzyl-4,6-dichloro-2-formamidopyrimidine

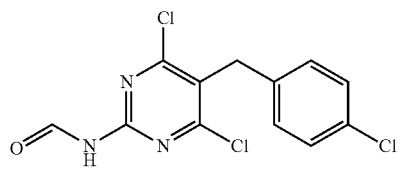 [SMILES: O=CNc1nc(Cl)c(Cc2ccc(Cl)cc2)c(Cl)n1] 4,6-dichloro-5-(4-chlorobenzyl)-2-formamidopyrimidine

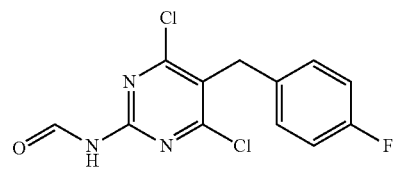 [SMILES: O=CNc1nc(Cl)c(Cc2ccc(F)cc2)c(Cl)n1] 4,6-dichloro-5-(4-fluorobenzyl)-2-formamidopyrimidine

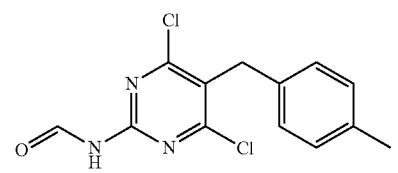 [SMILES: Cc1ccc(Cc2c(Cl)nc(NC=O)nc2Cl)cc1] 4,6-dichloro-2-formamido-5-(4-methylbenzyl)pyrimidine

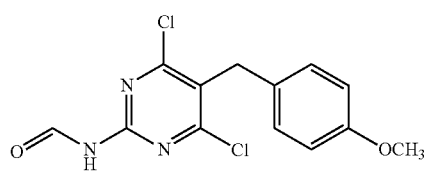 [SMILES: COc1ccc(Cc2c(Cl)nc(NC=O)nc2Cl)cc1] 4,6-dichloro-2-formamido-5-(4-methoxybenzyl)pyrimidine

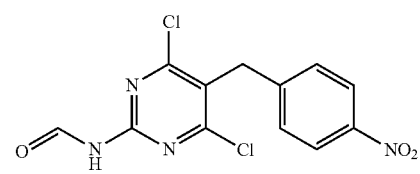 [SMILES: O=CNc1nc(Cl)c(Cc2ccc([N+](=O)[O-])cc2)c(Cl)n1] 4,6-dichloro-2-formamido-5-(4-nitrobenzyl)pyrimidine

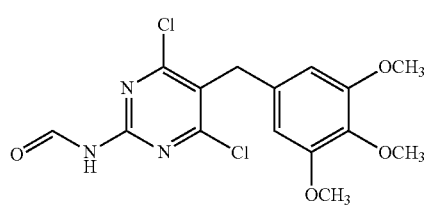 [SMILES: COc1cc(Cc2c(Cl)nc(NC=O)nc2Cl)cc(OC)c1OC] 4,6-dichloro-2-formamido-5-(3,4,5-trimethoxybenzyl)pyrimidine

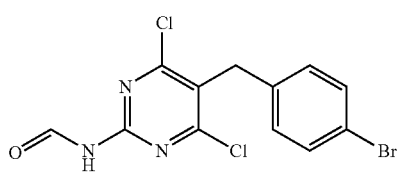 [SMILES: O=CNc1nc(Cl)c(Cc2ccc(Br)cc2)c(Cl)n1] 5-(4-bromobenzyl)-4,6-dichloro-2-formamidopyrimidine

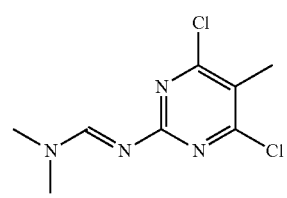 4,6-dichloro-5-methyl-2-{[(dimethylamino)methylene]amino}pyrimidine

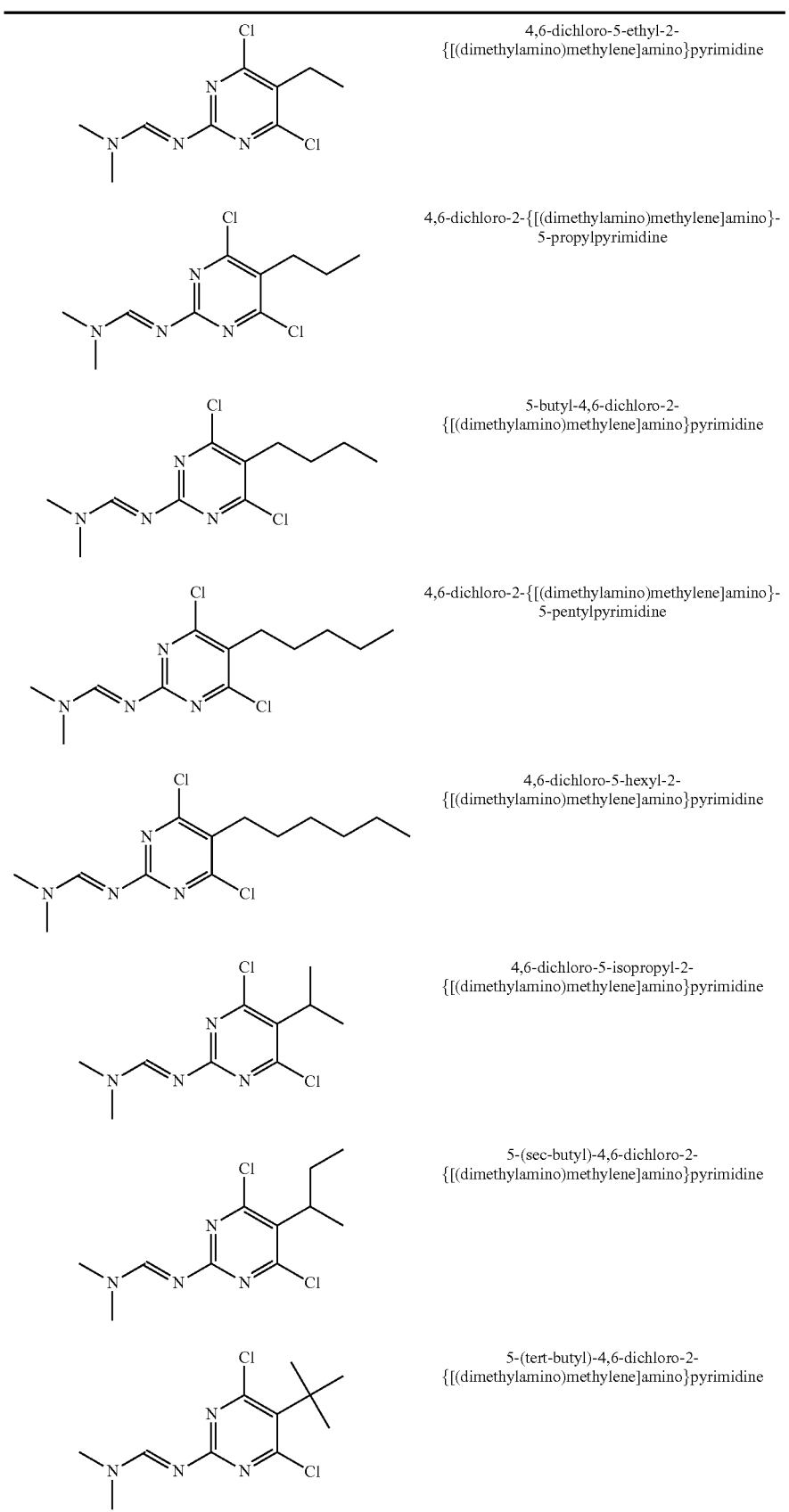

4,6-dichloro-5-ethyl-2-{[(dimethylamino)methylene]amino}pyrimidine 4,6-dichloro-2-{[(dimethylamino)methylene]amino}-5-propylpyrimidine 5-butyl-4,6-dichloro-2-{[(dimethylamino)methylene]amino}pyrimidine 4,6-dichloro-2-{[(dimethylamino)methylene]amino}-5-pentylpyrimidine 4,6-dichloro-5-hexyl-2-{[(dimethylamino)methylene]amino}pyrimidine 4,6-dichloro-5-isopropyl-2-{[(dimethylamino)methylene]amino}pyrimidine 5-(sec-butyl)-4,6-dichloro-2-{[(dimethylamino)methylene]amino}pyrimidine 5-(tert-butyl)-4,6-dichloro-2-{[(dimethylamino)methylene]amino}pyrimidine

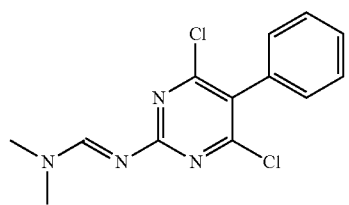 [SMILES: CN(C)/C=N/c1nc(Cl)c(-c2ccccc2)c(Cl)n1] 4,6-dichloro-2-{[(dimethylamino)methylene]amino}-5-phenylpyrimidine

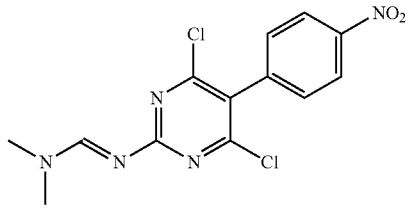 [SMILES: CN(C)/C=N/c1nc(Cl)c(-c2ccc([N+](=O)[O-])cc2)c(Cl)n1] 4,6-dichloro-2-{[(dimethylamino)methylene]amino}-5-(4-nitrophenyl)pyrimidine

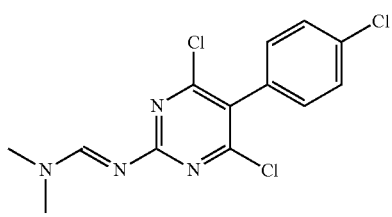 [SMILES: CN(C)/C=N/c1nc(Cl)c(-c2ccc(Cl)cc2)c(Cl)n1] 4,6-dichloro-5-(4-chlorophenyl)-2-{[(dimethylamino)methylene]amino}pyrimidine

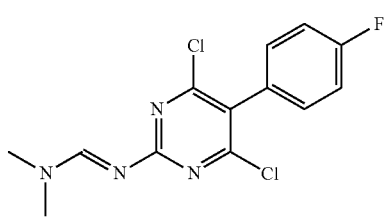 [SMILES: CN(C)/C=N/c1nc(Cl)c(-c2ccc(F)cc2)c(Cl)n1] 4,6-dichloro-5-(4-fluorophenyl)-2-{[(dimethylamino)methylene]amino}pyrimidine

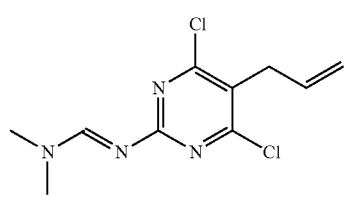 [SMILES: C=CCc1c(Cl)nc(/N=C/N(C)C)nc1Cl] 5-allyl-4,6-dichloro-2-{[(dimethylamino)methylene]amino}pyrimidine

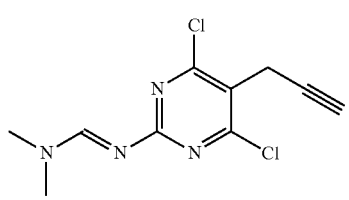 [SMILES: C#CCc1c(Cl)nc(/N=C/N(C)C)nc1Cl] 4,6-dichloro-2-{[(dimethylamino)methylene]amino}-5-(prop-2-yn-1-yl)pyrimidine

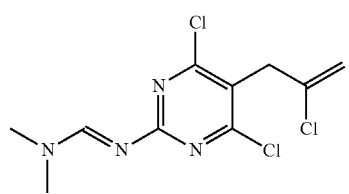 [SMILES: C=C(Cl)Cc1c(Cl)nc(/N=C/N(C)C)nc1Cl] 4,6-dichloro-5-(2-chloroallyl)-2-{[(dimethylamino)methylene]amino}pyrimidine

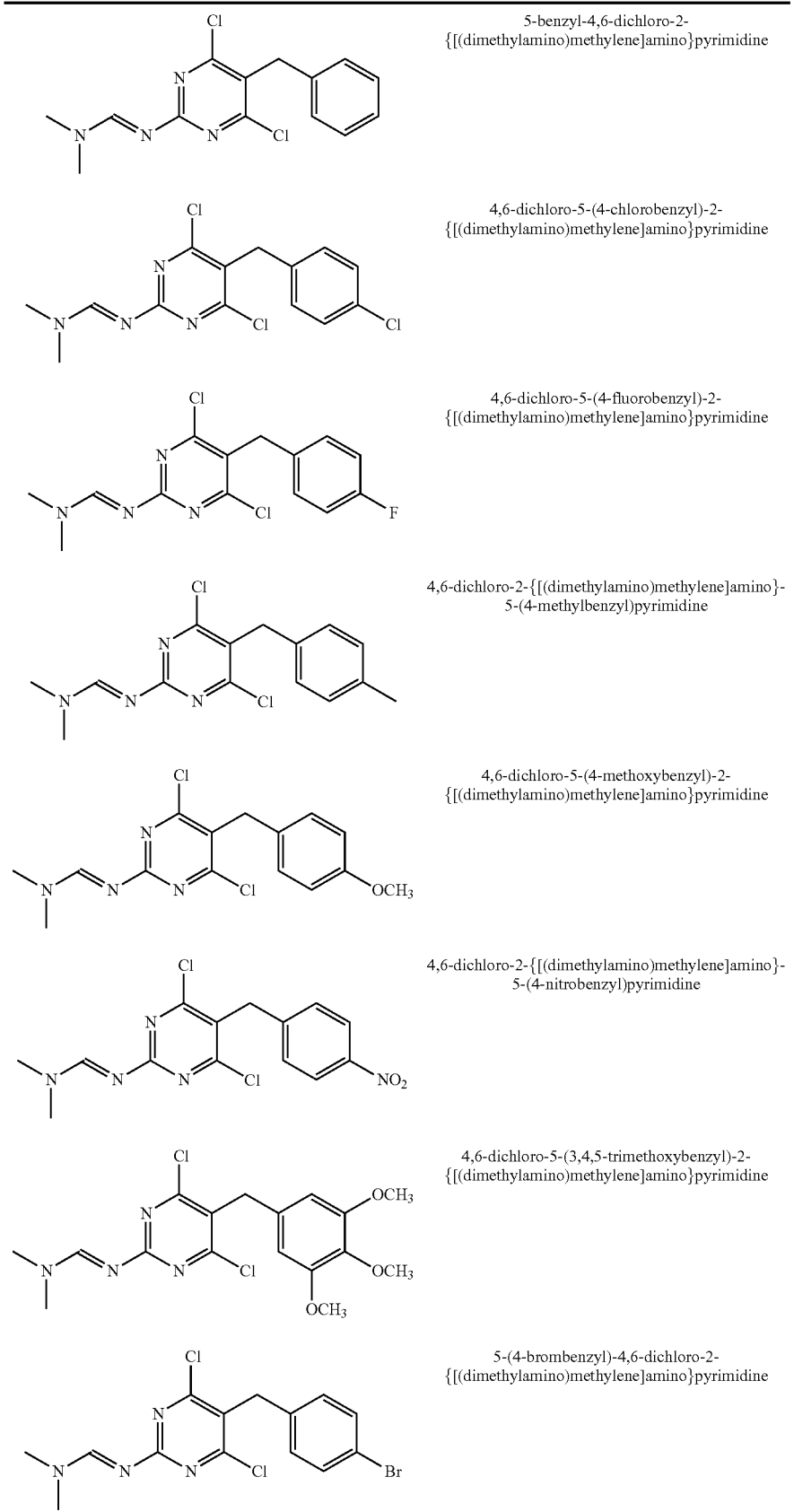

5-benzyl-4,6-dichloro-2-{[(dimethylamino)methylene]amino}pyrimidine 4,6-dichloro-5-(4-chlorobenzyl)-2-{[(dimethylamino)methylene]amino}pyrimidine 4,6-dichloro-5-(4-fluorobenzyl)-2-{[(dimethylamino)methylene]amino}pyrimidine 4,6-dichloro-2-{[(dimethylamino)methylene]amino}-5-(4-methylbenzyl)pyrimidine 4,6-dichloro-5-(4-methoxybenzyl)-2-{[(dimethylamino)methylene]amino}pyrimidine 4,6-dichloro-2-{[(dimethylamino)methylene]amino}-5-(4-nitrobenzyl)pyrimidine 4,6-dichloro-5-(3,4,5-trimethoxybenzyl)-2-{[(dimethylamino)methylene]amino}pyrimidine 5-(4-brombenzyl)-4,6-dichloro-2-{[(dimethylamino)methylene]amino}pyrimidine

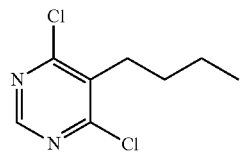 5-butyl-4,6-dichloropyrimidine
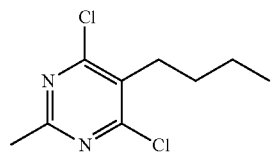 5-butyl-4,6-dichloro-2-methylpyrimidine
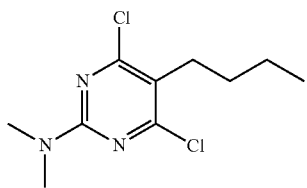 5-butyl-4,6-dichloro-2-(dimethylamino)pyrimidine
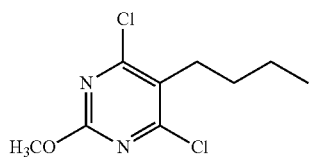 5-butyl-4,6-dichloro-2-methoxypyrimidine
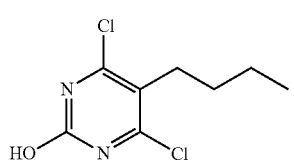 5-butyl-4,6-dichloro-2-hydroxypyrimidine
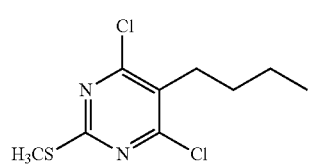 5-butyl-4,6-dichloro-2-(methylthio)pyrimidine
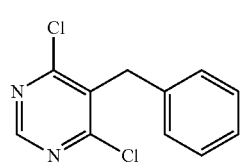 [SMILES: Clc1ncnc(Cl)c1Cc1ccccc1] 5-benzyl-4,6-dichloropyrimidine
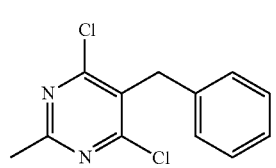 [SMILES: Cc1nc(Cl)c(Cc2ccccc2)c(Cl)n1] 5-benzyl-4,6-dichloro-2-methylpyrimidine
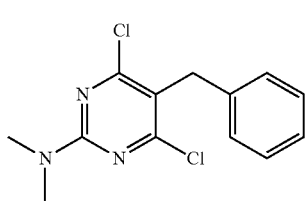 [SMILES: CN(C)c1nc(Cl)c(Cc2ccccc2)c(Cl)n1] 5-benzyl-4,6-dichloro-2-(dimethylamino)pyrimidine

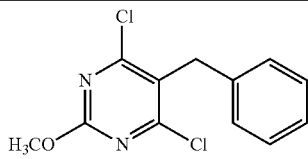

5-benzyl-4,6-dichloro-2-methoxypyrimidine

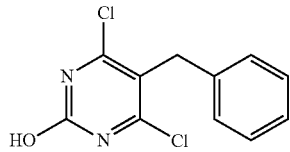 [SMILES: Oc1nc(Cl)c(Cc2ccccc2)c(Cl)n1]

5-benzyl-4,6-dichloro-2-hydroxypyrimidine

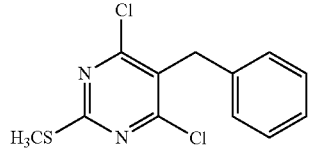

5-benzyl-4,6-dichloro-2-(methylthio)pyrimidine for use as medicaments.

Another aspect of this invention are the pyrimidine compounds of general formula I according to this invention for use in the treatment of diseases which are induced or the severity of which is potentiated by NO and/or prostaglandin E2 overproduction, in particular inflammatory or cancer diseases.

Another aspect of the invention is a method of preparation of the pyrimidine compounds of general formula I according to this invention, bearing a 2-formamido (i.e., 2-formylamino) group, which are prepared by a selective hydrolysis of the corresponding 2-[(dimethylamino)methylene] derivatives in an organic solvent in the presence of water, silica gel and acetic acid at room temperature. Ethyl acetate is preferably used as the organic solvent and the reaction is carried out at a temperature in the range from 10 to 30° C.

A further aspect of the invention is a pharmaceutical composition containing at least one pyrimidine compound of general formula I according to this invention, or their pharmaceutically acceptable salts.

The compound of general formula I according to this invention can be present in the pharmaceutical composition in its free form or in the form of a pharmaceutically acceptable salt, and in a preferred embodiment the pharmaceutical composition further contains at least one pharmaceutical carrier, excipient and/or diluent.

Another aspect of this invention is a pharmaceutical composition containing the pyrimidine compound(s) of general formula I according to this invention, or their pharmaceutically acceptable salts, as an active component.

A further aspect of the invention is the pharmaceutical composition having a pyrimidine compound of general formula I according to this invention, or its pharmaceutically acceptable salt, as the active component for use in the treatment of diseases which are induced or the severity of which is potentiated by NO and/or prostaglandin E2 overproduction, particularly inflammatory or cancer diseases.

An another aspect of the invention is the use of pyrimidine compounds of general formula I according to this invention, or their pharmaceutically acceptable salts, for the preparation of a medicament for the treatment of diseases which are induced or the severity of which is potentiated by NO and/or prostaglandin E2 overproduction, particularly inflammatory or cancer diseases.

A further aspect of the invention is a method of treatment of diseases which are induced or the severity of which is potentiated by NO and/or prostaglandin E2 overproduction, in particular inflammatory or cancer diseases, comprising administering a therapeutically effective amount of the pyrimidine compound of general formula I according to this invention to a subject in need of such treatment.

The inflammatory conditions in mammals including humans can be inhibited, alleviated or prevented. Examples of inflammatory diseases in mammals which can be treated by the administration of one or more pyrimidine compounds of general formula I according to this invention include but are not limited to: arthritic conditions such as ankylosing spondylitis (Bekhterev's disease), cervical arthritis, fibromyalgia, gout, rheumatoid arthritis, lumbosacral arthritis, osteoarthritis, osteoporosis, psoriatic arthritis, rheumatic disease; eczema, psoriasis, dermatitis and inflammatory conditions, such as heatstroke; inflammatory conditions of the eyes, such as uveitis and conjunctivitis; inflammatory conditions of the heart, such as myocarditis; inflammatory diseases of the female sexual organs; inflammatory diseases of the prostate; inflammatory diseases of the kidneys; inflammatory diseases of the tendons and muscles; pulmonary diseases connected with inflammation, such as asthma, cystic fibrosis and bronchitis; conditions of the gastrointestinal tract (GI) including ulcers, gingivitis, Crohn's disease, atrophic gastritis, ulcerative colitis, coeliac disease, regional ileitis, cholecystitis, peptic ulcer disease, pyrosis, and other damage of the GI tract, for instance induced by *Helicobacter pylori*; visceral inflammation, such as irritation of the bladder and cystitis; inflammatory neurological disorders of the central or peripheral nervous system, as well as painful and feverous conditions, such as the symptoms of influenza and other viral diseases, including the common cold, pain in the lumbar and cervical spine, headache and toothache, pains in the muscles after exertion, inflammations of the muscles, inflammations of the joints and tendons, neuropathic pains such as diabetic neuropathy, non-specific pain in the tailbone, pain in multiple sclerosis, muscle pain, neuropathy in HIV infections and neuralgia; multiple sclerosis; inflammatory neuropathies and the neurological complication of AIDS, inflammation connected with an autoimmune disease, with a trauma evoked by an operation, infections, metabolic disorders and tumors, by immunological events and disorders such as sepsis, septic shock, endotoxic shock, gram-negative sepsis, toxic-shock syndrome, reaction of a graft to the host and reaction of the host to the graft, Alzheimer's disease or pyresis, restenosis, silicosis, pulmonary sarcosis, diseases of the absorption of bone tissue, other diseases connected with immune system function disorders such as diabetes dependent on insulin, diabetes independent of insulin, lupus erythematosus and progressive retinal atrophy; diseases connected with damaging of the cells by free radicals and hence also oxidative stress, such as stroke, epilepsy, epileptic seizures including grand mal, petit mal, myoclonic epilepsy and partial seizures.

The compounds of the invention are further usable as anti-angiogenic, immunomodulation, antiproliferative and antitumor substances, usable for the treatment of diseases and conditions such as, but not limited to, hematologic cancer, e.g. leukemia, lymphoma, myeloma, or solid cancers, for instance cancers of the breast, prostate, liver, bladder, lungs, esophagus, stomach, further colorectal, urinary-sexual, gastrointestinal, skin, pancreatic cancers, cancers of brain, uterus, large intestine, head, throat, ovary, melanoma, astrocytoma, small-cell lung cancer, glioma, basal carcinomas and squamous cell carcinomas, sarcomas such as Kaposi's sarcoma and osteosarcoma, or treatment of disorders of T-cell formation such as aplastic anemia, DiGeorge syndrome and Graves-Basedow disease.

Another aspect of the invention is the pyrimidine compounds of formula I for use in human or veterinary medicine, especially for the treatment of conditions mediated by COX-2 and iNOS.

The use of the pyrimidines of formula I according to this invention is surprisingly not accompanied by adverse side effects, which are usually caused by the use of classic anti-inflammatory medications, e.g. non-steroidal anti-inflammatory medications such as indomethacin, or COX-2 inhibitors.

The mechanism of the present invention is the surprising simultaneous reduction of the production of two key signaling molecules (NO and prostaglandin E2). This effect is achieved by the use of the pyrimidines of formula I according to this invention. The presence of the substituent $R_2$ has the key influence on the biological activity of the compounds of the invention. Substances bearing a hydrogen atom in this position show only a very weak reduction of NO production without any effect on prostaglandin E2 production (or even increase the production of this prostaglandin). On the other hand, the substances disclosed herein, having e.g. an alkyl, aryl or heteroaryl substituent in position $R_2$ (or their substituted analogs), show a surprising and therapeutically very important simultaneous reduction of NO and prostaglandin E2 production. It is surprising that the very presence of the substituent $R_2$ is important, with a very wide range of substituents in the position $R_2$ being shown to be functional.

The term 'treatment', 'cure' or 'therapy' used herein refers to both the treatment of the symptoms already developed and preventive or prophylactic administration.

The invention further includes the pyrimidine compounds of general formula I for administration as active substances of a pharmaceutically acceptable composition which can be produced using the usual methods known in the art of formulation, e.g. by the effective substance binding to a pharmaceutically acceptable, therapeutically inert organic and/or inorganic carrier or excipient, or by mixing the components.

The compounds of general formula I according to this invention can also be used in the form of a precursor (prodrug) or in another suitable form which releases the active substance in vivo. Such precursors provide for instance suitable modifications of the $R_1$ substituent of the compounds of general formula I, wherein by masking [Advanced Drug Delivery Reviews 59, 677-694, 2007; Nature Reviews Drug Discovery 7, 255-270, 2008] of the functionalized amino group it is possible to obtain substances with a higher solubility in water and/or a greater oral biological availability; this masking under in vivo conditions subsequently releases the actual active substance.

The pyrimidines of formula I according to this invention can be administered in the form of various pharmaceutical formulations, e.g. orally in the form of tablets, pastilles, capsules, sugar- or film-coated tablets, liquid solutions, emulsions or suspensions, rectally in the form of suppositories, parenterally e.g. by intramuscular or intravenous injection or infusion, and transdermally in the form of a patch, ointment, emulsion, lotion, solution, gel, cream and nasal spray or aerosol mixtures. A pharmaceutical composition may also have a form enabling the controlled release of a compound of general formula I according to this invention. The compounds of the invention can also be processed into the form of a depot medium. These media with long-lasting effect could be administered in the form of an implant, e.g. subcutaneous or intramuscular, or in the form of an intramuscular injection. For this purpose, the compounds according to this invention can be processed together with suitable polymer or hydrophobic materials, e.g. into the form of an emulsion in an acceptable oil or together with ion-exchange resins.

Pharmaceutically acceptable, therapeutically inert organic and/or inorganic carriers or excipients which are suitable for the production of the pharmaceutical compositions include, e.g., water, gelatin, gum arabic, lactose, starch, cellulose, glucose, magnesium stearate, talc, vegetable oils, polyalkylene glycols, titanium dioxide etc. The pyrimidines of formula I according to this invention can be sterilized. The pharmaceutical compositions can contain further components which are well known in the art, such as e.g. preservatives, colorants, sweeteners, flavors, aromatizers, solvents, antioxidants, stabilizers, emulsifiers, wetting agents or emollients, e.g. paraffin oil, mannide monooleate, salts for the modification of osmotic pressure, buffers etc.

Furthermore, the solid oral forms can contain together with the active substance also diluents, e.g., lactose, dextrose, saccharose, cellulose, corn starch or potato starch; lubricants, e.g., silica, talc, stearic acid, magnesium or calcium stearate and/or polyethylene glycols; binding agents, e.g., starches, gum arabic, gelatin, methyl cellulose, carboxymethyl cellulose or polyvinyl pyrrolidone; disintegrants, e.g., starch, alginic acid, alginates or sodium starch glycolate; soaking mixtures; colorants; sweeteners; emulsifiers and wetting agents, such as lecithin, polysorbates, lauryl sulfates; and generally non-toxic and pharmacologically inactive substances used in pharmaceutical formulations. Pharmaceutical preparations may be produced by any known method, e.g., by means of mixing, granulating, tableting, sugar- or film-coating processes.

Oral applications include also controlled-release formulations, which can be produced through a commonly used procedure, e.g. through the application of enteric-film coating of tablets and granules.

The liquid dispersions for oral administration may be, e.g., syrups, emulsions and suspensions. The syrups may further contain e.g. saccharose with glycerine, and/or mannitol and/or sorbitol as a carrier. The suspensions and emulsions may contain, e.g., natural gum, agar, sodium alginate, pectin, methyl cellulose, carboxymethyl cellulose or polyvinyl alcohol. The suspensions or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride. The solutions for intravenous administration or infusions may contain as the carrier, e.g., sterile water or preferably may be in the form of sterile, aqueous or isotonic saline solutions.

The suppositories could along with the active substance contain a pharmaceutically acceptable carrier, e.g., cocoa butter, polyethylene glycol, polyoxyethylene sorbitan fatty acid ester, surfactant or lecithin.

The optimum therapeutically effective doses to be administered may be easily determined by those skilled in the art and will vary basically with the concentration of the pharmaceutical composition, the mode of administration and the advancement of the inflammatory condition or of the type of the disorder treated. Furthermore, the factors associated with the respective patient being treated, including his/her age, weight, prescribed diet and length of administration, will require the adjustment of the dose to an appropriate therapeutically effective amount. In general, the daily doses of the compounds of general formula I according to this invention will preferably range from 0.001 to 500 mg/kg, preferably from 0.01 to 100 mg/kg of the body weight. The precise dosage will depend on the above-mentioned factors.

Yet another aspect of the invention describes polysubstituted pyrimidine compounds of general formula I bearing in position 5 a substituent other than hydrogen

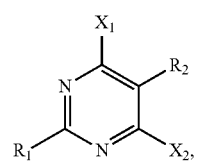

(I)

wherein
a) for $X_1=X_2=C_1$ and $R_1=NH_2$, $R_2$ is selected from the group comprising:
propyl, pentyl, hexyl, isopropyl, sec-butyl, tert-butyl, 2-chloroallyl, 4-fluorobenzyl, 4-chlorobenzyl, 4-methylbenzyl;
b) for $X_1=X_2=I$ and $R_1=NH_2$, $R_2$ is alkyl, alkenyl, alkynyl, cycloalkyl, cycloalkenyl, aryl or heteroaryl;
c) for $X_1=X_2=Br$ and $R_1=NH_2$, $R_2$ is alkyl, alkenyl, alkynyl, cycloalkyl, cycloalkenyl, aryl or heteroaryl;
d) for $X_1=C_1$, $X_2=I$ and $R_1=NH_2$, $R_2$ is alkyl, alkenyl, alkynyl, cycloalkyl, cycloalkenyl, aryl or heteroaryl;
e) for $X_1=C_1$, $X_2=Br$ and $R_1=NH_2$, $R_2$ is alkyl, alkenyl, alkynyl, cycloalkyl, cycloalkenyl, aryl or heteroaryl;
f) for $X_1=Br$, $X_2=I$ and $R_1=NH_2$, $R_2$ is alkyl, alkenyl, alkynyl, cycloalkyl, cycloalkenyl, aryl or heteroaryl;
g) for $X_1=Br$, $X_2=$aryl or heteroaryl, and $R_1=NH_2$, $R_2$ is alkyl, alkenyl, alkynyl, cycloalkyl, cycloalkenyl, aryl or heteroaryl;
h) for $X_1=I$, $X_2=$aryl or heteroaryl, and $R_1=NH_2$, $R_2$ is alkyl, alkenyl, alkynyl, cycloalkyl, cycloalkenyl, aryl or heteroaryl;
i) for $R_1=$formamido (formylamino), $X_1=Cl$, Br, I, aryl or heteroaryl, and $X_2=Cl$, Br, I, aryl or heteroaryl, $R_2$ is alkyl, alkenyl, alkynyl, cycloalkyl, cycloalkenyl, aryl or heteroaryl;
j) for $R_1=$alkylcarbonylamino, arylcarbonylamino, heteroarylcarbonylamino, $X_1=Br$, I, aryl or heteroaryl, $X_2=Br$, I, aryl or heteroaryl, $R_2$ is alkyl, alkenyl, alkynyl, cycloalkyl, cycloalkenyl, aryl or heteroaryl;
k) for $R_1=$N,N-dialkylaminomethyleneamino, $X_1=Cl$, Br, I, aryl or heteroaryl, $X_2=Cl$, Br, I, aryl or heteroaryl, $R_2$ is alkyl, alkenyl, alkynyl, cycloalkyl, cycloalkenyl, aryl or heteroaryl;
l) for $R_1=$N,N-dialkylamino-1-alkylmethyleneamino, N,N-dialkylamino-1-arylmethyleneamino, N,N-dialkylamino-1-heteroarylmethyleneamino, $X_1=Cl$, Br, I, aryl or heteroaryl, $X_2=Cl$, Br, I, aryl or heteroaryl, $R_2$ is alkyl, alkenyl, alkynyl, cycloalkyl, cycloalkenyl, aryl or heteroaryl;
wherein individual substituents have the meanings as defined above,
provided that:
1) $X_1$ and/or $X_2$ are not unsubstituted or substituted indole bound directly to the pyrimidine ring by the position 3 of the indole ring; or
2) $R_2$ is not selected from arbitrarily substituted phenyl bound directly to the pyrimidine ring, from the groups —C(O)NR$_a$R$_b$, —C(S)NR$_a$R$_b$, —NR$_a$C(O)R$_b$ and —NR$_a$C(S)R$_b$, wherein R$_a$ and R$_b$ are any substituents, $R_2$ is not the group —CN, and $R_2$ is not selected from the following groups:

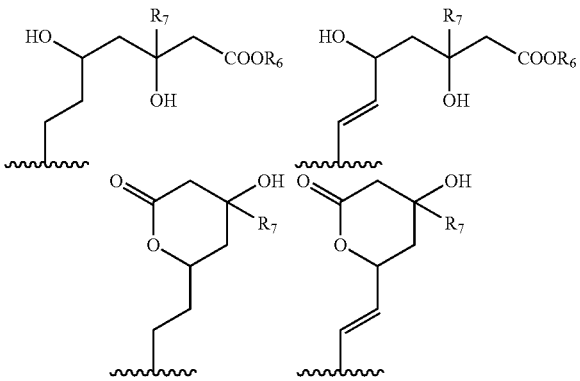

wherein $R_6$ and $R_7$ is any substituent; or
3) $R_1$ is not the substituent -Q-T-C—$R_5$, wherein $R_5$ is halogen or —OSO$_2$R; Q is any linker; T is solely —CO—, —CS—, —SO$_2$— and C is arbitrarily substituted carbon, and $R_1$ is not an arbitrarily substituted phenylaminocarbonylamino group;
or their pharmaceutically acceptable salts, for use as medicaments.

The invention is further illustrated by the following examples, which should not be construed as limiting.

BRIEF DESCRIPTION OF THE DRAWINGS

FIG. 2A shows the effect of the substances administered on the length of the intestine (on the y axis), FIG. 2B shows the effect of the substances administered on the severity of the illness according to a point scale (on the y axis), FIG. 2C shows the effect of the substances administered on the size of the spleen (on the y axis) and FIG. 2D shows the effect of the substances administered on the severity of the illness according to a histological evaluation (on the y axis).

FIG. 5 depicts the results of the testing of the mutagenicity of compound 28 under the usage of the bacterial strain *Salmonella typhimurium* TA 100 under the usage of metabolic activation (+MA I) and without it (−MA I). On the x axis, the dosage of the test compound applied on the plate is plotted, on the y axis the number of revertants created.

FIG. 6A,B depicts in vitro HUVEC tube formation on a gel of basement membrane extract (Matrigel™). The calcein AM stained image of well-developed tubular network of untreated cells is on the 6A and tube disruption induced by 10 μM of compound 23 is on 6B.

EXAMPLES

Figure 1:
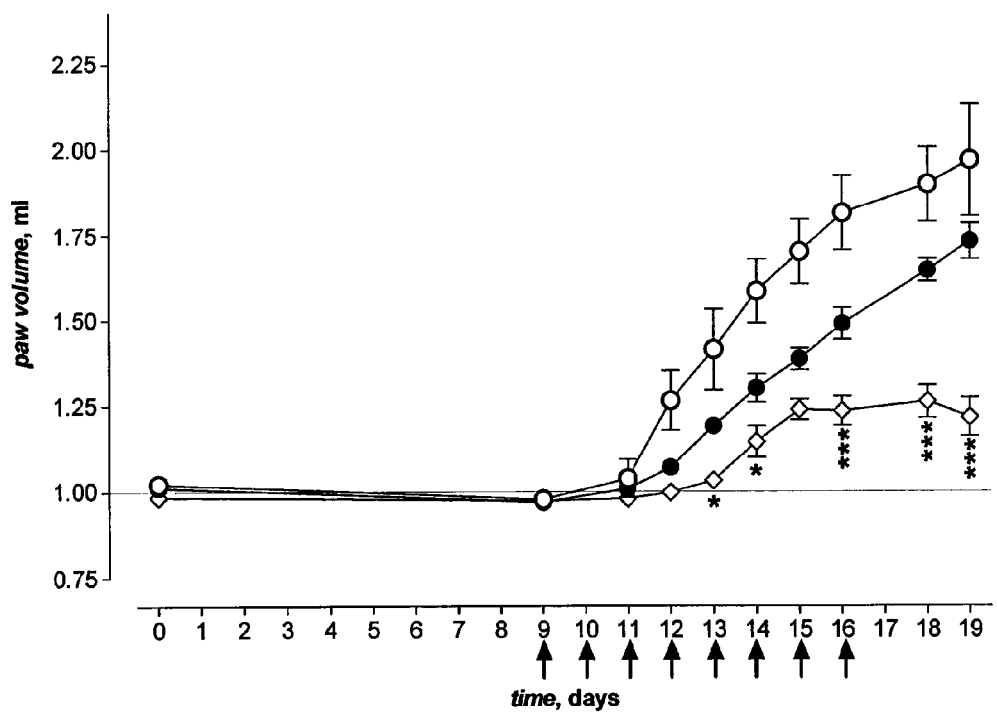
FIG. 1 shows the effect of compound 51 on the severity of adjuvant arthritis in sewer rats, a model of human rheumatoid arthritis. It represents the changes in the size of the paws of the sewer rats after the application of Freund's complete adjuvant (FCA), in dependence on time. The groups are labeled in the following way: ○ control group, the animals were treated with FCA; ● control group, the animals were treated with FCA and 0.5% methylcellulose (i.e. vehicle); ◇ experimental group, the animals were treated with FCA and compound 51. The application was begun on Day 9, completed on Day 16 after the induction of arthritis (marked with arrows on the x axis). The asterisks mark the statistically significant reduction of the swelling of the paws on the probability level $P<0.05$ (*) or $P<0.001$ (***).
Figure 2A:
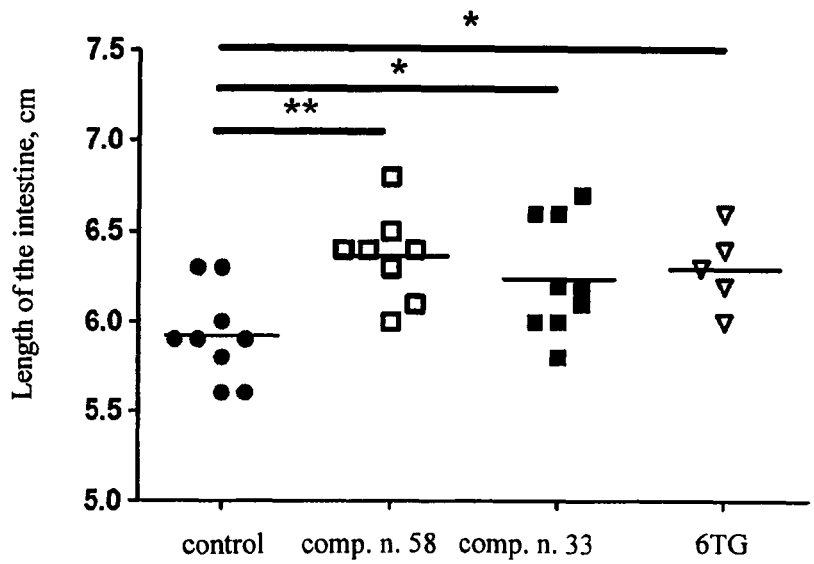
FIG. 2A-D documents the therapeutic efficiency of compounds 28 and 51 according to the invention on acute colitis, induced in mice females with dextran sulphate sodium. The effectiveness was evaluated after the administration of the actual methylcellulose (●) as a placebo, of compound 28 (□) and compound 51 (■), dissolved always in a 0.5% solution of methylcellulose, and 6-thioguanine (∇) in a 0.5% solution of methylcellulose as a positive control. Statistical significance: * p<0.05;  p<0.01; *p<0.001.
Figure 2B:
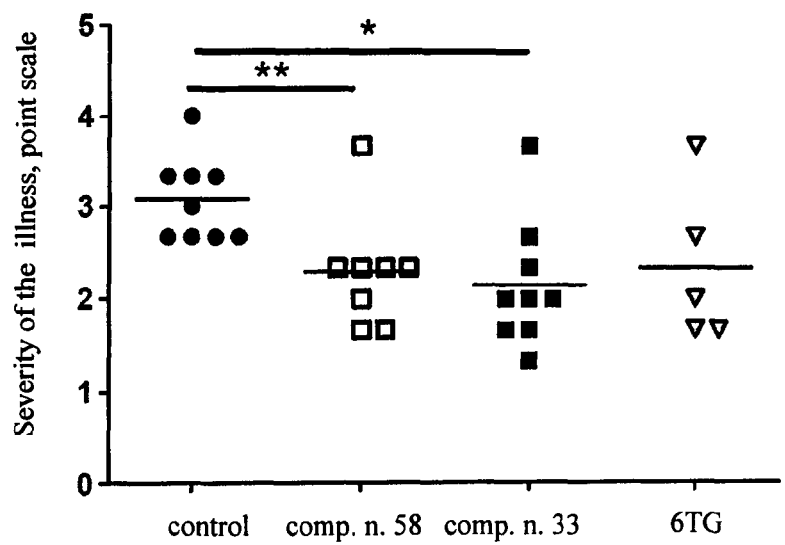
Figure 2C:
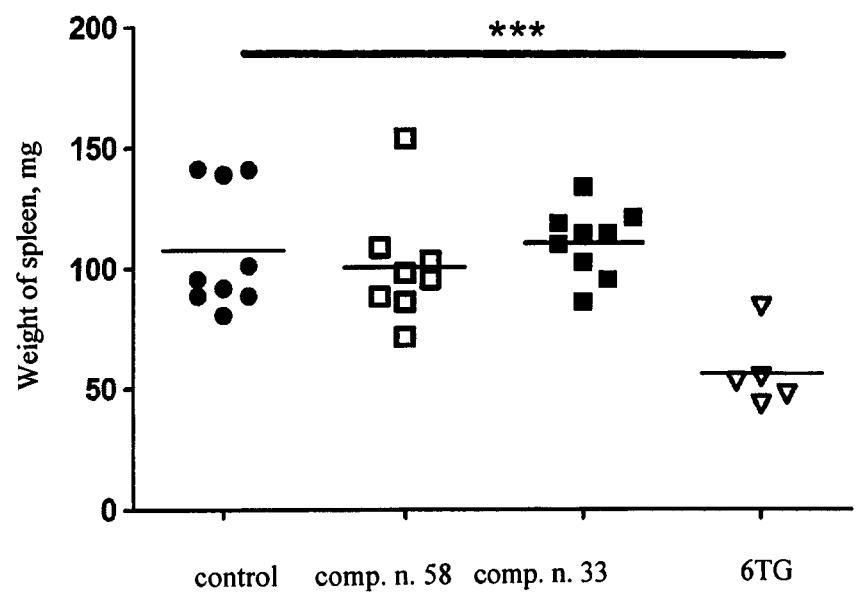
Figure 2D:
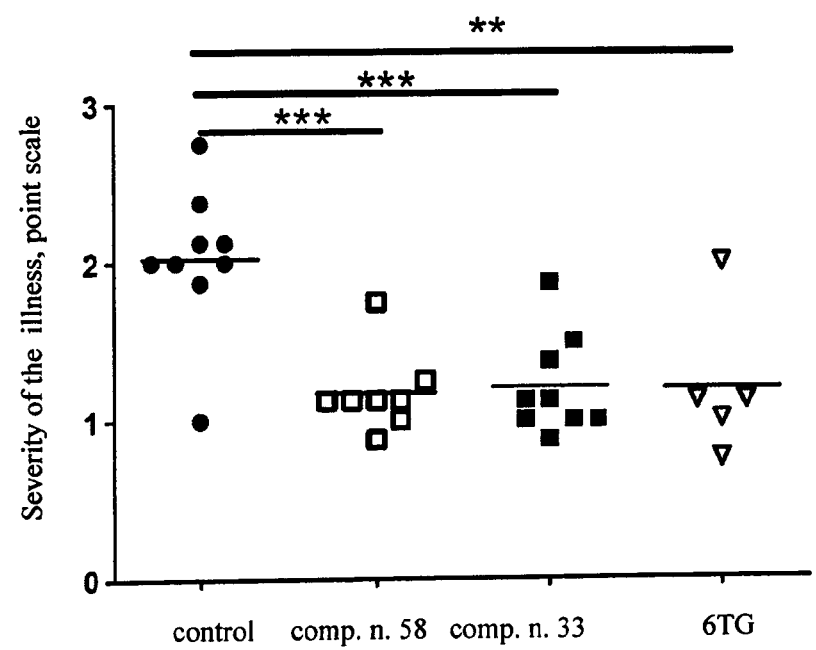

I. Synthesis of the Compounds of Formula I According to this Invention

GC/MS analyses were measured using a 6890N gas chromatograph (Agilent, Santa Clara, Calif., USA) attached to a quadrupole mass detector. A HP-5 ms capillary (30 m×0.25 mm; 0.25 μm; Agilent) was used for the analyses. The carrier gas was helium with a flow rate of 1 ml/min. The EI mass spectra were measured on a GCT Premier (Waters) OA-TOF GC mass spectrometer.

The FAB mass spectra were measured on a ZAB-EQ (VG Analytical) spectrometer using FAB (ionization by Xe, accelerating voltage 8 kV, glycerol matrix).

The elemental composition of the prepared compounds was determined using a PE 2400 Series II CHNS/O Elemental Analyzer (Perkin Elmer, USA, 1999).

The melting point was set by a Stuart SMP3 Melting Point Apparatus.

TLC was performed on TLC aluminum sheets—silica gel 60 $F_{254}$ (MERCK KGaA, Germany).

The NMR spectra were measured on an FT NMR spectrometer (Bruker Avance II 500) in DMSO-$d_6$ ($^1$H at 500 MHz, $^{13}$C at 125.7 MHz and $^{19}$F at 188.2 MHz), chemical Shift are expressed in parts per million, ppm, and interaction constants J in Hz.

The X-ray structure was acquired with an Oxford Diffraction Xcalibur PX X-ray diffractometer.

The essential pyrimidine ring of the compounds according to this invention is prepared through the known condensation of malonic acid diesters with guanidine in a basic medium. This reaction is well known from the literature [Chemische Berichte, 96, 2786, 1963; Journal Organic Chemistry Vol. 40, 3713-3716, 1975; U.S. Pat. Appl. Publ. No., 2004204386; PCT Int. Appl., 9208705,], but its performance has a crucial impact on the yield and purity of the product.

Example 1

Preparation of 5-substituted 2-amino-4,6-dihydroxypyrimidines

In 300 ml of absolute ethanol, 12.9 g (0.56 mol) of metallic podium were dissolved under inert gas (argon) while being intensively mixed with a shaft stirrer. The reaction vessel was equipped with a condensation cooler with a chlorocalcium stopper in order to prevent the pressure of the reaction mixture from increasing because of the massive generation of hydrogen and fast heating of the solvent, which shifts even to boiling. After all the sodium was dissolved and the reaction mixture was cooled to room temperature, 21.02 g (0.22 mol) of guanidine hydrochloride were added under intensive stirring, followed by 0.2 mol of the respective monosubstituted malonic acid diester (e.g. 43.26 g of diethyl butylammonate. The reaction mixture was further intensively stirred due to the production of the solid product, which is so massive that after two hours it already practically precludes stirring. After another two hours, 200 ml of absolute ethanol were added and the reaction mixture was heated to the boiling point for one hour while being stirred. Afterward, ca 200-300 ml of ethanol were evaporated on a vacuum rotary evaporator and 500 ml of water were added to the reaction mixture. After stirring, the product (in the form of sodium salt) was partially dissolved. This suspensions was subsequently neutralized by by adding ethanoic acid dropwise, causing an immediate separation of the desired product in the form of a sediment. This was subsequently refluxed for 10 minutes and then cooled to laboratory temperature. This refluxing and cooling was repeated twice more, with the yield being a well-filterable solid product. Having been drained and rinsed with 2×50 ml of water, 2×50 ml of ethanol and 2×50 ml of acetone, the product was dried in a vacuum drier at 60° C. and under 0.1 mbar for two days. The obtained purity of the product prepared in this manner is sufficient for the following reaction and based on analyses contains only crystalline water.

2-amino-4,6-dihydroxy-5-methyl-pyrimidine (1)

Yield: 30.86 g (corresponding to 91% of the theor. yield); melting point (hereinafter only as m.p.) >250° C. $^1$H NMR (DMSO-$d_6$): 10.701 bs, 2H, (2×OH); 6.88 bs, 2H, (NH$_2$); 1.57 s, 3H, (H-1'). $^{13}$C NMR (DMSO-$d_6$): 164.97 (C-4 and 6); 152.53 (C-2); 84.06 (C-5); 8.11 (C-1'). For $C_5H_7N_3O_2$+1.6 $H_2O$: calculated: 35.34% C, 6.05% H, 24.72% N. found: 35.57% C, 6.15% H, 24.59% N.

2-amino-5-ethyl-4,6-dihydroxypyrimidine (2)

Yield: 32.54 g (88% of the theor. yield); m.p. >250° C. $^1$H NMR (DMSO-$d_6$): 10.30 bs, 2H, (2×OH); 6.30 bs, 2H, (NH₂); 2.14 q, 2H, J(1',2')=7.3 (H-1'); 0.88 t, 3H, J(2',1')=7.3 (H-2'). ¹³C NMR (DMSO-d₆): 164.47 (C-4 and 6); 152.54 (C-2); 91.88 (C-5); 15.62 (C-1'); 13.89 (C-2'). For $C_6H_9N_3O_2+1.7\ H_2O$: calculated: 38.79% C, 6.73% H, 22.62% N. found: 38.83% C, 7.90% H, 22.41% N.

2-amino-4,6-dihydroxy-5-propylpyrimidine (3)

Yield: 33.86 g (94% of the theor. yield); m.p. >250° C. ¹H NMR (DMSO-d₆): 10.30 bs, 2H, (2×OH); 6.31 bs, 2H, (NH₂); 2.10 t, 2H, J(1',2')=7.5 (H-1'); 1.32 m, 2H, (H-2'); 0.80 t, 3H, J(3,2')=7.4 (H-3'). ¹³C NMR (DMSO-d₆): 164.75 (C-4 and 6); 152.57 (C-2); 90.20 (C-5); 22.44 (C-1'); 21.89 (C-2'); 14.17 (C-3'). For $C_7H_{11}N_3O_2+0.6\ H_2O$: calculated: 46.71% C, 6.83% H, 23.35% N. found: 46.80% C, 6.79% H, 23.32% N.

2-amino-4,6-dihydroxy-5-isopropylpyrimidine (4)

Yield: 32.36 g (93% of the theor. yield); m.p. >250° C. ¹H NMR (DMSO-d₆): 10.45 bs, 2H, (2×OH); 6.62 bs, 2H, (NH₂); 2.96 sept, 1H, J(CH,CH₃)=7.1 (H—CH); 1.08 d, 6H, J(CH₃,CH)=7.1 (2×CH₃). ¹³C NMR (DMSO-d₆): 164.19 (C-4 and 6); 152.40 (C-2); 94.80 (C-5); 22.94 (CH); 20.96 (CH₃). For $C_7H_{11}N_3O_2+0.3\ H_2O$: calculated: 48.16% C, 6.70% H, 24.07% N. found: 48.11% C, 7.62% H, 23.98% N.

5-allyl-2-amino-4,6-dihydroxypyrimidine (5)

Yield: 38.57 g (95% of the theor. yield); m.p. >250° C. ¹H NMR (DMSO-d₆): 10.35 bs, 2H, (2×OH); 6.40 bs, 2H, (NH₂); 5.73 ddt, 1H, J(2',1')=6.1, J(2',3'$_{cis}$)=10.0, J(2',3'$_{trans}$)=17.2 (H-2'); 4.87 ddt, 1H, J(3'$_{trans}$,1')=1.6, J(gem)=2.3, J(3'$_{trans}$,2')=17.2 (H-3'$_{trans}$); 4.79 ddt, 1H, J(3'₁, 1')=1.6, J(gem)=2.3, J(3'$_{cis}$, 2')=10.0 (H-3'$_{cis}$); 2.85 dt, 2H, J(1',3')=1.6, J(1',2')=6.1 (H-1'). ¹³C NMR (DMSO-d₆): 164.36 (C-4 and 6); 152.71 (C-2); 137.73 (C-2'); 113.32 (C-3'); 87.73 (C-5); 26.67 (C-1'). For $C_7H_9N_3O_2+2\ H_2O$: calculated: 41.38% C, 6.45% H, 20.68% N. found: 41.44% C, 6.17% H, 20.47% N.

2-amino-4,6-dihydroxy-5-(prop-2-yn-1-yl)pyrimidine (6)

Yield: 33.47 g (96% of the theor. yield); m.p. >250° C. ¹H NMR (DMSO-d₆): 10.55 bs, 2H, (2×OH); 6.79 bs, 2H, (NH₂); 2.95 d, 2H, J(1,3')=2.6 (H-1'); 2.43 t, 1H, J(3',1')=2.6 (H-3'). ¹³C NMR (DMSO-d₆): 163.69 (C-4 and 6); 152.69 (C-2); 89.05 (C-5); 84.97 (C-2'); 68.02 (C-3'); 12.06 (C-1'). For $C_7H_7N_3O_2+0.5\ H_2O$: calculated: 48.28% C, 4.63% H, 24.13% N. found: 48.09% C, 4.33% H, 24.23% N.

2-amino-5-butyl-4,6-dihydroxypyrimidine (7)

Yield: 39.61 g (97% of the theor. yield); m.p. >250° C. ¹H NMR (DMSO-d₆): 10.30 bs, 2H, (2×OH); 6.32 bs, 2H, (NH₂); 2.12 t, 2H, J(1',2')=7.1 (H-1'); 1.28 m, 2H and 1.23 m, 2H, (H-2' and H-3'); 0.85 t, 3H, J(4',3')=7.2 (H-4'). ¹³C NMR (DMSO-d₆): 164.67 (C-4 and 6); 152.54 (C-2); 90.36 (C-5); 31.04 (C-1'); 22.32 (C-2'); 21.98 (C-3'); 14.22 (C-4'). For $C_8H_{13}N_3O_2+1.2\ H_2O$: calculated: 46.91% C, 7.58% H, 20.52% N. found: 47.15% C, 7.69% H, 20.36% N.

2-amino-5-(perdeutero-butyl)-4,6-dihydroxypyrimidine (8)

The yield from 58 mmol of the starting substance was 8.93 g (74% of the theor. yield); m.p. >250° C. ¹H NMR (DMSO-d₆): 10.30 bs, 2H, (2×OH); 6.34 bs, 2H, (NH₂). ¹³C NMR (DMSO-d₆): 164.79 (C-4 and 6); 152.59 (C-2); 90.35 (C-5); 29.81 m (C-2'); 21.20 m (C-1' and 3'); 13.00 m (C-4'). For $C_8H_4D_9N_3O_2+0.9\ H_2O$: calculated: 46.09% C, 11.50% H (+D), 20.16% N. found: 46.17% C, 7.62% H, 20.05% N (recalculation of % H to H+D 11.58%).

2-amino-5-sec-butyl-4,6-dihydroxypyrimidine (9)

Yield: 36.89 g (93% of the theor. yield); m.p. >250° C. ¹H NMR (DMSO-d₆): 10.20 bs, 2H, (2×OH); 6.31 bs, 2H, (NH₂); 2.70 m, 1H, (H-1'); 1.65 m, 1H and 1.40 m, 1H, (H-2'); 1.06 d, 3H, J(1'',1')=7.0 (H-1''); 0.72 t, 3H, J(3',2')=7.4 (H-3'). ¹³C NMR (DMSO-d₆): 164.46 (C-4 and 6); 152.47 (C-2); 93.61 (C-5); 31.08 (C-1'); 27.09 (C-2'); 19.00 (C-1''); 13.03 (C-3'). For $C_8H_{13}N_3O_2+0.8\ H_2O$: calculated: 48.62% C, 7.45% H, 21.26% N. found: 48.57% C, 7.47% H, 21.18% N.

2-amino-5-hexyl-4,6-dihydroxypyrimidine (10)

The yield from 49 mmol of the starting substance was 8.35 g (79% of the theor. yield); m.p. >250° C. ¹H NMR (DMSO-d₆): 10.25 bs, 2H, (2×OH); 6.28 bs, 2H, (NH₂); 2.11 m, 2H, (H-1'); 1.31-1.19 m, 8H(H-2', 3', 4', 5'); 0.84 t, 3H, J(6',5')=7.0 (H-6'). ¹³C NMR (DMSO-d₆): 164.73 (C-4 and 6); 152.57 (C-2); 90.49 (C-5); 31.60 (C-4'); 28.98 and 28.79 (C-2' and 3'); 22.41 and 22.35 (C-1' and 5'); 14.26 (C-6'). For $C_{10}H_{17}N_3O_2+0.2\ H_2O$: calculated: 55.90% C, 8.16% H, 19.56% N. found: 55.84% C, 8.19% H, 19.63% N.

2-amino-5-benzyl-4,6-dihydroxypyrimidine (11)

Yield: 43.21 g (91% of the theor. yield); m.p. >250° C. ¹H NMR (DMSO-d₆): 10.42 bs, 2H, (2×OH); 7.18 m, 4H and 7.07 m, 1H (phenyl); 6.46 bs, 2H, (NH₂); 3.44 s, 2H, (CH₂). ¹³C NMR (DMSO-d₆): 164.47 (C-4 and 6); 152.68 (C-2); 143.10, 128.31, 127.90 and 125.20 (C-phenyl); 94.51 (C-5); 28.12 (CH₂). For $C_{11}H_{11}N_3O_2+1.1\ H_2O$: calculated: 55.74% C, 5.61% H, 17.73% N. found: 55.71% C, 5.54% H, 17.60% N.

2-amino-5-phenyl-4,6-dihydroxypyrimidine (12)

Yield: 41.43 g (94% of the theor. yield); m.p. >250° C. ¹H NMR (DMSO-d₆): 10.60 bs, 2H, (2×OH); 7.50 d, 2H, 7.19 t, 2H and 7.02 t, 1H (phenyl); 6.74 bs, 2H, (NH₂). ¹³C NMR (DMSO-d₆): 162.84 (C-4 and 6); 152.02 (C-2); 135.40, 130.26, 126.84 and 124.19 (C-phenyl); 106.11 (C-5). For $C_{10}H_9N_3O_2+1\ H_2O$: calculated: 54.29% C, 5.01% H, 19.00% N. found: 54.17% C, 5.19% H, 18.82% N.

The second stage of the synthesis of the compounds according to the present invention is a functional substitution of two hydroxyl groups for two chlorine atoms. For these reactions, chlorides of such mineral acids as $POCl_3$, $PCl_5$, $SOCl_2$ or $COCl_2$ with diverse additives like pyridine, 2-methylpyridine, diphenylamine or triethylamine are generally used. For the preparation of the desired 5-substituted 2-amino-4,6-dihalogenpyrimidines, these classical procedures turned out to be unsuitable owing to their very low, max. 30%, isolated yields. This synthesis problem has been resolved by applying a modified synthetic procedure for the preparation of 4,6-dichloro-2,5-bis-{[(dimethylamino)methylene]amino}pyrimidine [see Nucleosides, Nucleotides & Nucleic Acids, 19(1.2), 297-327, 2000] under the usage of the Vilsmeier-Haack-Arnold reagent.

Example 2

Preparation of 5-substituted-4,6-dichloro-2-{[(dimethylamino)methylene]amino}-pyrimidines Prior to the reaction, the starting 5-substituted 2-amino-4,6-dihydroxypyrimidine was dried again in a vacuum drier at 80° C. and under 0.1 mbar for one day, because the present crystalline water increases the amount of the Vilsmeier-Haack-Arnold reagent, which is required for a full conversion.

Subsequently, 0.1 mol of 5-substituted 2-amino-4,6-dihydroxypyrimidine (e.g. 18.32 g of 2-amino-5-butyl-4,6-dihydroxypyrimidine) was suspended under inert atmosphere in 400 ml of a 2 mol·l$^{-1}$ solution of the Vilsmeier-Haack-Arnold reagent in chloroform (0.8 mol=8 equivalents). Once the starting material and the reaction vessel are thoroughly exsiccated, it is possible to reduce the amount of the reagent down to 6 equivalents. Instead of chloroform, it is possible to use other solvents (for this reaction inert) such as e.g. dichloromethane, tetrahydrofuran or toluene. The reaction mixture was subsequently refluxed for four hours, during which the starting material was completely dissolved and the reaction mixture became yellow to red. Having been cooled to laboratory temperature, the reaction mixture was poured onto ice and rapidly neutralized by NaHCO$_3$. The obtained mixture was quickly transferred into a separatory funnel and immediately extracted by 3×100 ml of chloroform. The organic fractions were connected and dried using MgSO$_4$. The chloroform solution obtained in this manner was filtered through a thin layer (ca 0.5 cm) of neutral silica gel and subsequently thoroughly evaporated on a vacuum evaporator with a yield of an oily product of a yellow color, which gradually crystallizes into white crystals covered with yellow to reddish oil. Having been added 50 ml of a hexane and ether mixture, the product acquired in this manner was exposed to the effect of ultrasound for 10 min. Having been cooled by ice bath, the separated crystals were sucked off and twice rinsed with the hexane and ether mixture. The isolated product was dried in a vacuum drier at laboratory temperature and under 0.1 mbar for one day.

4,6-dichloro-5-methyl-2-{[(dimethylamino)methylene]amino}pyrimidine (13)

Yield: 21.78 g (93% of the theor. yield); m.p. 84-86° C. $^1$H NMR (DMSO-d$_6$): 8.55 s, 1H, (CH); 3.16 s, 3H and 3.03 s, 3H, (2×NCH$_3$); 2.27 s, 3H, (H-1'). $^{13}$C NMR (DMSO-d$_6$): 163.87 (C-2); 160.86 (C-4 and 6); 159.21 (NCH); 118.89 (C-5); 40.94 and 35.02 (2×NCH$_3$); 15.41 (C-1'). For C$_8$H$_{10}$Cl$_2$N$_4$: calculated: 41.22% C, 4.32% H, 30.42% Cl, 24.04% N. found: 41.29% C, 4.42% H, 30.56% Cl, 24.27% N. MS (EI), m/z (%): 232 and 234 [M$^+$] (100).

4,6-dichloro-5-ethyl-2-{[(dimethylamino)methylene]amino}pyrimidine (14)

Yield: 22.45 g (91% of the theor. yield); m.p. 78-80° C. $^1$H NMR (DMSO-d$_6$): 8.56 s, 1H, (CH); 3.17 s, 3H and 3.03 s, 3H, (2×NCH$_3$); 2.70 q, 2H, J(1',2')=7.4 (H-1'); 1.11 t, 3H, J(2',1')=7.4 (H-2'). $^{13}$C NMR (DMSO-d$_6$): 163.97 (C-2); 160.58 (C-4 and 6); 159.24 (NCH); 123.86 (C-5); 40.89 and 34.98 (2×NCH$_3$); 22.78 (C-1'); 12.51 (C-2'). For C$_9$H$_{12}$Cl$_2$N$_4$: calculated: 43.74% C, 4.89% H, 28.69% Cl, 22.67% N. found: 43.53% C, 4.98% H, 28.43% Cl, 22.89% N. MS (EI), m/z (%): 246 and 248 [M$^+$] (100), 231 and 233 [M$^+$-Me] (53).

4,6-dichloro-2-{[(dimethylamino)methylene]amino}-5-propylpyrimidine (15)

Yield: 23.61 g (90% of the theor. yield); m.p. 76-78° C. $^1$H NMR (DMSO-d$_6$): 8.58 s, 1H, (CH); 3.15 s, 3H and 3.05 s, 3H, (2×NCH$_3$); 2.72 t, 2H, J(1',2')=7.7 (H-1'); 1.56 m, 2H, (H-2'); 0.96 t, 3H, J(3',2')=7.3 (H-3'). $^{13}$C NMR (DMSO-d$_6$): 163.57 (C-2); 160.31 (C-4 and 6); 159.22 (NCH); 126.53 (C-5); 40.93 and 34.95 (2×NCH$_3$); 31.00 (C-1'); 20.96 (C-2'); 13.81 (C-3'). For C$_{10}$H$_{14}$Cl$_2$N$_4$: calculated: 45.99% C, 5.40% H, 27.15% Cl, 21.45% N. found: 45.87% C, 5.32% H, 27.11% Cl, 21.37% N. MS (EI), m/z (%): 260 and 262 [M$^+$] (100). MS (FAB$^+$), m/z (%): 261 and 263 [M+H$^+$] (100).

4,6-dichloro-5-isopropyl-2-{[(dimethylamino)methylene]amino}pyrimidine (16)

Yield: 22.83 g (87% of the theor. yield); m.p. 77-78° C. $^1$H NMR (DMSO-d$_6$): 8.55 s, 1H, (CH); 3.55 sept, 1H, J(CH, CH$_3$)=7.2 (CH); 3.17 s, 3H and 3.03 s, 3H, (2×NCH$_3$); 1.32 d, 6H, J(CH$_3$,CH)=7.2 (2×CH$_3$). $^{13}$C NMR (DMSO-d$_6$): 163.51 (C-2); 160.43 (C-4 and 6); 159.23 (NCH); 126.49 (C-5); 40.90 and 34.98 (2×NCH$_3$); 38.87 (CH); 19.51 (CH$_3$). For C$_{10}$H$_{14}$Cl$_2$N$_4$: calculated: 45.99% C, 5.40% H, 27.15% Cl, 21.45 N. found: 46.22% C, 5.63% H, 27.43% Cl, 21.18% N. MS (EI), m/z (%): 260 and 262 [M$^+$] (100).

5-allyl-4,6-dichloro-2-{[(dimethylamino)methylene]amino}pyrimidine (17)

Yield: 24.75 g (96% of the theor. yield); m.p. 80-81° C. $^1$H NMR (DMSO-d$_6$): 8.58 s, 1H, (CH); 5.86 ddt, 1H, J(2',1')=5.8, J(2',3'$_{cis}$)=10.1, J(2',3'$_{trans}$)=17.2 (H-2'); 5.08 dg, 1H, J(3'cis,1')=J(gem)=1.6, J(3'$_{cis}$.2')=10.1 (H-3'$_{cis}$); 4.98 dq, 1H, J(3'trans,1')=J(gem)=1.7, J(3'trans,2')=17.2 (H-3'$_{trans}$); 3.45 dt, 2H, J(1'.3')=1.7, J(1'.2')=5.8 (H-1'); 3.18 s, 3H and 3.04 s, 3H, (2×NCH$_3$). $^{13}$C NMR (DMSO-d$_6$): 164.28 (C-2); 161.16 (C-4 and 6); 159.36 (NCH); 132.99 (C-2'); 120.02 (C-5); 116.70 (C-3'); 40.93 and 35.01 (2×NCH$_3$); 33.08 (C-1'). For C$_{10}$H$_{12}$Cl$_2$N$_4$: calculated: 46.35% C, 4.67% H, 27.36% Cl, 21.62% N. found: 46.86% C, 4.89% H, 27.12% Cl, 21.33% N. MS (EI), m/z (%): 258 and 260 [M$^+$] (100).

4,6-dichloro-2-{[(dimethylamino)methylene]amino}-5-(prop-2-yn-1-yl)pyrimidine (18)

Yield: 23.69 g (92% of the theor. yield); m.p. 82-83° C. $^1$H NMR (DMSO-d$_6$): 8.59 s, 1H, (CH); 3.62 d, 2H, J(1'.3')=2.6 (H-1'); 3.18 s, 3H and 3.05 s, 3H, (2×NCH$_3$); 3.01 t, 1H, J(3'.1')=2.6 (H-3'). $^{13}$C NMR (DMSO-d$_6$): 164.50 (C-2); 160.65 (C-4 and 6); 159.57 (NCH); 118.09 (C-5); 79.28 (C-2'); 72.30 (C-3'); 41.00 and 35.07 (2×NCH$_3$); 19.40 (C-2'). For C$_{10}$H$_{10}$Cl$_2$N$_4$: calculated: 46.71% C, 3.92% H, 27.58% Cl, 21.79% N. found: 46.78% C, 3.86% H, 27.39% Cl, 21.52% N. MS (EI), m/z (%): 256 and 258 [M$^+$] (100).

5-butyl-4,6-dichloro-2-{[(dimethylamino)methylene]amino}pyrimidine (19)

Yield: 26.13 g (95% of the theor. yield); m.p. 65-67° C. $^1$H NMR (DMSO-d$_6$): 8.55 s, 1H, (CH); 3.16 s, 3H and 3.03 s, 3H, (2×NCH$_3$); 2.66 m, 2H, 1.46 m, 2H and 1.35 m, 2H (3×CH$_2$); 0.90 t, 3H, J(4'.3')=7.3 (H-4'). $^{13}$C NMR (DMSO-d$_6$): 163.92 (C-2); 160.75 (C-4 and 6); 159.21 (NCH); 122.71 (C-5); 40.89 and 34.98 (2×NCH$_3$); 30.03, 28.83 and 22.12 (C-1', 2' and 3'); 13.78 (C-4'). For C$_{11}$H$_{16}$Cl$_2$N$_4$: calculated: 48.01% C, 5.86% H, 25.77% Cl, 20.36% N. found: 47.80% C, 5.82% H, 25.49% Cl, 20.12% N. MS (EI), m/z (%): 274 and 276 [M⁺] (41), 231 and 233 [M⁺-Pr] (100). GC/MS-EI (R$_T$ 21.76 min), m/z (%): 274 and 276 [M⁺] (43), 231 and 233 [M⁺-Pr] (100), min. 99.5% purity.

5-(perdeutero-butyl)-4,6-dichloro-2-{[(dimethylamino)methylene]amino}pyrimidine (20)

The yield from 20 mmol of the starting substance was 4.87 g (86% of the theor. yield); m.p. 66-68° C. ¹H NMR (DMSO-d$_6$): 8.55 s, 1H, (CH); 3.16 s, 3H and 3.03 s, 3H, (2×NCH$_3$). ¹³C NMR (DMSO-d$_6$): 163.97 (C-2); 160.79 (C-4 and 6); 159.74 (NCH); 122.74 (C-5); 40.92 and 34.96 (2×NCH$_3$); 28.83 m, 28.04 m and 20.85 m (C-1', 2' and 3'); 12.67 m (C-4'). For C$_{11}$H$_7$D$_9$Cl$_2$N$_4$: calculated: 46.48% C, 8.86% H (+D), 24.95% Cl, 19.71% N. found: 46.60% C, 5.63 H, 24.76% Cl, 19.52% N (recalculation of % H to H+D 8.80%). MS (EI), m/z (%): 283 and 285 [M⁺] (20), 233 and 235 [M⁺-per.D-Pr] (100).

5-sec-butyl-4,6-dichloro-2-{[(dimethylamino)methylene]amino}pyrimidine (21)

Yield: 25.64 g (93% of the theor. yield); m.p. 67-68° C. ¹H NMR (DMSO-d$_6$): 8.55 s, 1H, (CH); 3.30 m, 1H, (H-1'); 3.17 s, 3H and 3.03 s, 3H, (2×NCH$_3$); 1.90 m, 1H and 1.68 m, 1H (H-2'); 1.29 d, 3H, J(1".1')=7.2 (H-1"); 0.77 t, 3H, J(3'.2')=7.4 (H-3'). ¹³C NMR (DMSO-d$_6$): 163.64 (C-2); C-4 and C-6 not found; 159.28 (NCH); 125.07 (C-5); 40.90 and 36.03 (2×NCH$_3$); 34.97 (C-1'); 26.49 (C-2'); 17.78 (C-1"); 15.50 (C-3'). For C$_{11}$H$_{16}$Cl$_2$N$_4$: calculated: 48.01% C, 5.86% H, 25.77% Cl, 20.36% N. found: 48.21% C, 5.81% H, 25.59% Cl, 20.24% N. MS (EI), m/z (%): 274 and 276 [M⁺] (100).

4,6-dichloro-5-hexyl-2-{[(dimethylamino)methylene]amino}pyrimidine (22)

The yield from 28 mmol of the starting substance was 6.94 g (82% of the theor. yield); m.p. 59-60° C. ¹H NMR (DMSO-d$_6$): 8.55 s, 1H, (CH); 3.16 s, 3H and 3.03 s, 3H, (2×NCH$_3$); 2.66 m, 2H, (H-1'); 1.49 m, 2H, (H-2'); 1.33 m, 2H, (H-3'); 1.30-1.25 m, 4H, (H-4' and 5'); 0.85 m, 3H, (H-6'). ¹³C NMR (DMSO-d$_6$): 163.93 (C-2); 160.76 (C-4 and 6); 159.22 (NCH); 122.75 (C-5); 40.89 and 34.97 (2×NCH$_3$); 31.04 (C-4'); 29.10 (C-1'); 28.59 (C-3'); 27.79 (C-2'); 22.16 (C-5'); 14.05 (C-6'). For C$_{13}$H$_{20}$Cl$_2$N$_4$: calculated: 51.49% C, 6.65% H, 23.38% Cl, 18.48% N. found: 51.56% C, 6.62% H, 23.61% Cl, 18.38% N. MS (EI), m/z (%): 302 and 304 [M⁺] (17), 231 and 233 [M⁺-Pn] (100).

5-benzyl-4,6-dichloro-2-{[(dimethylamino)methylene]amino}pyrimidine (23)

Yield: 28.74 g (93% of the theor. yield); m.p. 63-65° C. ¹H NMR (DMSO-d$_6$): 8.59 s, 1H, (CH); 7.30 t, 2H, 7.21 t, 1H and 7.16 d, 2H, (phenyl); 4.10 s, 2H, (CH$_2$); 3.18 s, 3H and 3.05 s, 3H, (2×NCH$_3$). ¹³C NMR (DMSO-d$_6$): 164.36 (C-2); 161.55 (C-4 and 6); 159.46 (NCH); 137.63, 128.77, 127.99 and 126.68 (phenyl); 121.24 (C-5); 40.95 and 35.04 (2×NCH$_3$); 34.49 (CH$_2$). For C$_{14}$H$_{14}$Cl$_2$N$_4$: calculated: 54.38% C, 4.56% H, 22.93% Cl, 18.12% N. found: 54.14% C, 4.37% H, 22.75% Cl, 18.41% N. MS (EI), m/z (%): 308 and 310 [M⁺] (100). GC/MS-EI (R$_T$ 26.85 min), m/z (%): 308 and 310 [M⁺] (100), min. 99.5% purity.

4,6-dichloro-2-{[(dimethylamino)methylene]amino}-5-phenylpyrimidine (24)

Yield: 26.31 g (89% of the theor. yield); m.p. 67-68° C. ¹H NMR (DMSO-d$_6$): 8.66 s, 1H, (CH); 7.47 t, 2H, 7.43 t, 1H and 7.35 d, 2H, (phenyl); 3.20 s, 3H and 3.08 s, 3H, (2×NCH$_3$). ¹³C NMR (DMSO-d$_6$): 164.74 (C-2); 160.08 (C-4 and 6); 159.56 (NCH); 134.01, 130.10, 128.73 and 128.63 (phenyl); 124.11 (C-5); 41.02 and 35.12 (2×NCH$_3$). For C$_{13}$H$_{12}$Cl$_2$N$_4$: calculated: 52.90% C, 4.10% H, 24.02% Cl, 18.98% N. found: 52.83% C, 4.27% H, 24.21% Cl, 18.84% N. MS (EI), m/z (%): 294 and 296 [M⁺] (100).

Example 3

Preparation of 5-substituted 2-amino-4,6-dichloropyrimidines

Substituted 4,6-dichloro-2-{[(dimethylamino)methylene]amino}pyrimidines were subjected to deprotextion of the (dimethylamino)methylene protecting group from the amino group in position 2 of the pyrimidine ring. For this reaction, the method described in the literature [Nucleosides, Nucleotides & Nucleic Acids 19(1a2), 297-327, 2000] was used, innovatively modified in order to make it possible to merely filter the product from the reaction mixture.

A flask was filled with 50 mmol of substituted 4,6-dichloro-2-{[(dimethylamino)methylene]amino}-pyrimidine, 200 ml of 99% ethanol and 20 ml of resultant HCl. The reaction mixture was subsequently warmed up to 50° C. for two hours, during which a crystalline product began to separate directly from the reaction mixture. After that, 300 ml of water were added and the reaction mixture was intensively stirred for 10 minutes while quantitatively yielding the desired product, which was subsequently sucked off and rinsed with 2×50 ml of a water/ethanol mixture (1/1), 1×5% NaHCO$_3$ aqueous solution and 1×50 ml of a water/ethanol mixture (1/1). The product was subsequently recrystallized in 99% ethanol. After complete cooling to 0° C., the separated white crystals were sucked off, rinsed with 1×50 ml of a water/ethanol mixture (1/1) and dried in a vacuum drier.

2-amino-4,6-dichloro-5-methylpyrimidine (25)

Yield: 8.53 g (96% of the theor. yield); m.p. 189-190° C. ¹H NMR (DMSO-d$_6$): 7.26 bs, 2H, (NH$_2$); 2.17 s, 3H, (H-1'). ¹³C NMR (DMSO-d$_6$): 161.01 (C-4 and 6); 160.78 (C-2); 113.60 (C-5); 14.93 (C-1'). For C$_5$H$_5$Cl$_2$N$_3$: calculated: 33.73% C, 2.83% H, 39.83% Cl, 23.60% N. found: 33.53% C, 2.78% H, 40.02% Cl, 23.42% N. MS (EI), m/z (%): 177 and 179 [M⁺] (100). MS (ESI+), m/z (%): 178 and 180 [M+H⁺] (100).

2-amino-4,6-dichloro-5-ethylpyrimidine (26)

Yield: 9.4 g (98% of the theor. yield); m.p. 183-185° C. ¹H NMR (DMSO-d$_6$): 7.32 bs, 2H, (NH$_2$); 2.61 q, 2H, J(1',2')=7.4 (H-1'); 1.07 t, 3H, J(2',1')=7.4 (H-2'). ¹³C NMR (DMSO-d$_6$): 160.83 (C-2); 160.76 (C-4 and 6); 118.90 (C-5); 22.41 (C-1'); 12.92 (C-2'). For C$_6$H$_7$Cl$_2$N$_3$: calculated: 37.52% C, 3.67% H, 36.92% Cl, 21.88% N. found: 37.59% C, 3.73% H, 36.76% Cl, 21.77% N. MS (EI), m/z (%): 191 and 193 [M⁺] (100).

2-amino-4,6-dichloro-5-propylpyrimidine (27)

Yield: 9.86 g (96% of the theor. yield); m.p. 182-183° C. ¹H NMR (DMSO-d$_6$): 7.52 bs, 2H, (NH$_2$); 2.69 t, 2H, J(1',2')=7.6 (H-1'); 1.52 m, 2H, (H-2'); 0.91 t, 3H, J(3'.2')=7.2 (H-3'). ¹³C NMR (DMSO-d$_6$): 160.78 (C-2); 160.69 (C-4 and 6); 119.20 (C-5); 31.12 (C-1'); 20.86 (C-2'); 13.75 (C-3'). For C$_7$H$_9$Cl$_2$N$_3$: calculated: 40.80% C, 4.40% H, 34.41% Cl, 20.39% N. found: 40.79% C, 4.32% H, 34.15% Cl, 20.19% N. MS (EI), m/z (%): 205 and 207 [M⁺] (100).

2-amino-5-butyl-4,6-dichloropyrimidine (28)

Yield: 10.83 g (98% of the theor. yield); m.p. 169-170° C. ¹H NMR (DMSO-d₆): 7.29 bs, 2H, (NH₂); 2.59 m, 2H, 1.45 m, 2H and 1.33 m, 2H (3×CH₂); 0.91 t, 3H, J(4',3')=7.3 (H-4'). ¹³C NMR (DMSO-d₆): 160.78 (C-2); 160.76 (C-4 and 6); 117.71 (C-5); 30.37, 28.46 and 22.04 (C-1', 2' and 3'); 13.81 (C-4'). For C₈H₁₁Cl₂N₃: calculated: 43.66% C, 5.04% H, 32.22% Cl, 19.09% N. found: 43.70% C, 4.93% H, 32.24% Cl, 18.87% N. GC/MS-EI (R$_T$ 16.03 min), m/z (%): 219 and 221 [M⁺] (18), 176 and 178 [M⁺-Pr] (100), min. 99.5% purity.

2-amino-4,6-dichloro-5-isopropylpyrimidine (29)

Yield: 10.07 g (98% of the theor. yield); m.p. 175-176° C. ¹H NMR (DMSO-d₆): 7.31 bs, 2H, (NH₂); 3.46 sept, 1H, J(CH,CH₃)=7.2 (CH); 1.28 d, 6H, J(CH₃,CH)=7.2 (2×CH₃). ¹³C NMR (DMSO-d₆): 160.62 (C-2); 160.32 (C-4 and 6); 121.65 (C-5); 28.57 (CH); 19.82 (CH₃). For C₇H₉Cl₂N₃: calculated: 40.80% C, 4.40% H, 34.41% Cl, 20.39% N. found: 40.57% C, 4.54% H, 34.69% Cl, 20.67% N. MS (EI), m/z (%): 205 and 207 [M⁺] (100).

2-amino-5-(sec-butyl)-4,6-dichloropyrimidine (30)

Yield: 10.64 g (97% of the theor. yield); m.p. 159-160° C. ¹H NMR (DMSO-d₆): 7.33 s, 2H, (NH₂); 3.23 m, 1H, (H-1'); 1.83 m, 1H and 1.64 m, 1H(H-2'); 1.25 d, 3H, J(1",1')=6.2 (H-1"); 0.77 t, 3H, J(3',2')=7.4 (H-3'). ¹³C NMR (DMSO-d₆): 163.64 (C-2); C-4 and C-6 not found; 120.12 (C-5); 35.72 (C-1'); 26.67 (C-2'); 18.13 (C-1"); 12.53 (C-3'). For C₈H₁₁Cl₂N₃: calculated: 43.66% C, 5.04% H, 32.22% Cl, 19.09% N. found: 43.63% C, 4.82% H, 32.17% Cl, 18.86% N. MS (EI), m/z (%): 219 and 221 [M⁺] (100).

2-amino-4,6-dichloro-5-phenylpyrimidine (31)

Yield: 11.57 g (96% of the theor. yield); m.p. 193-195° C. ¹H NMR (DMSO-d₆): 7.60 bs, 2H, (NH₂); 7.44 t, 2H, 7.40 t, 1H and 7.30 d, 2H, (phenyl). ¹³C NMR (DMSO-d₆): 161.46 (C-2); 160.26 (C-4 and 6); 134.24, 130.47, 128.55 and 128.46 (phenyl); 119.71 (C-5). For C₁₀H₇Cl₂N₃: calculated: 50.03% C, 2.94% H, 29.53% Cl, 17.50% N. found: 49.86% C, 2.82% H, 38.44% Cl, 17.23% N. MS (EI), m/z (%): 239 and 241 [M⁺] (100).

5-allyl-2-amino-4,6-dichloropyrimidine (32)

Yield: 9.96 g (98% of the theor. yield); m.p. 175-177° C. ¹H NMR (DMSO-d₆): 7.40 bs, 2H, (NH₂); 5.83 ddt, 1H, J(2',1')=5.8, J(2',3'$_{cis}$)=10.1, J(2',3'$_{trans}$)=17.1 (H-2'); 5.06 dq, 1H, J(3'cis,1')=J(gem)=1.6, J(3'$_{cis}$,2')=10.1 (H-3'$_{cis}$); 4.96 dq, 1H, J(3'trans,1')=J(gem)=1.7, J(3'trans,2')=17.1 (H-3'$_{trans}$); 3.36 dt, 2H, J(1',3')=1.7, J(1',2')=5.8 (H-1'). ¹³C NMR (DMSO-d₆): 161.33 (C-4 and 6); 161.08 (C-2); 133.57 (C-2'); 116.28 (C-3'); 115.01 (C-5); 32.70 (C-1'). For C₇H₇Cl₂N₃: calculated: 41.20% C, 3.46% H, 34.75% Cl, 20.59% N. found: 41.12% C, 3.37% H, 34.54% Cl, 20.56% N. MS (EI), m/z (%): 203 and 205 [M⁺] (100).

2-amino-4,6-dichloro-5-(prop-2-yn-1-yl)pyrimidine (33)

Yield: 9.76 g (97% of the theor. yield); m.p. 159-161° C. ¹H NMR (DMSO-d₆): 7.50 bs, 2H, (NH₂); 3.52 d, 2H, J(1',3')= 2.7 (H-1'); 2.96 t, 1H, J(3',1')=2.7 (H-3'). ¹³C NMR (DMSO-d₆): 161.20 (C-2); 160.84 (C-4 and 6); 113.30 (C-5); 79.86 (C-2'); 71.96 (C-3'); 19.03 (C-2'). For C₇H₅Cl₂N₃: calculated: 41.61% C, 2.49% H, 35.09% Cl, 20.80% N. found: 41.41% C, 2.48% H, 34.96% Cl, 20.55% N. MS (EI), m/z (%): 201 and 203 [M⁺] (100).

2-amino-5-benzyl-4,6-dichloropyrimidine (34)

Yield: 12.48 g (98% of the theor. yield); m.p. 196-197° C. ¹H NMR (DMSO-d₆): 7.46 bs, 2H, (NH₂); 7.29 t, 2H, 7.20 t, 1H and 7.15 d, 2H (phenyl); 4.01 s, 2H, (CH₂). ¹³C NMR (DMSO-d₆): 161.75 (C-4 and 6); 161.15 (C-2); 138.16, 128.72, 127.92 and 126.56 (C-phenyl); 116.29 (C-5); 34.15 (CH₂). For C₁₁H₉Cl₂N₃: calculated: 51.99% C, 3.57% H, 27.90% Cl, 16.54% N. found: 51.92% C, 3.66% H, 28.02% Cl, 16.68% N. MS (EI), m/z (%): 253 and 255 [M⁺] (100).

2-amino-5-(perdeutero-butyl)-4,6-dichloropyrimidine (35)

The yield from 5 mmol: 1036 mg (90% of the theor. yield); m.p. 170-171° C. ¹H NMR (DMSO-d₆): 7.29 bs, 2H, (NH₂). ¹³C NMR (DMSO-d₆): 160.82 (C-2); 160.71 (C-4 and 6); 117.53 (C-5); 28.97 m, 28.21 m and 21.41 m (C-1', 2' and 3'); 13.20 m (C-4'). For C₈H₂D₉Cl₂N₃: calculated: 41.93% C, 8.79% H (+D), 30.94% Cl, 18.34% N. found: 41.86% C, 4.76% H, 30.76% Cl, 18.17% N (recalculation of % H to H+D 8.65%). GC/MS-EI (R$_T$ 15.89 min), m/z (%): 228 and 230 [M⁺] (18), 178 and 180 [M⁺-per.D-Pr] (100), min. 99.5% purity.

Example 4

Preparation of 4,6-dihalogenopyrimidines with Other Halogens than Two Chlorine Atoms For the preparation of 4,6-diiodopyrimidines, the Finkelstein reaction of 4,6-dichloropyrimidines with sodium iodide and hydroiodic acid in dry acetone was utilized. As full conversion did not occur, also the respective 4-chloro-6-iodopyrimidines were obtained.

A flask was filled with 2 mmol of 5-substituted 2-amino-4,6-dichloropyrimidine, 1.5 g (10 mmol) of sodium iodide, 5 ml of hydroiodic acid (57%) and 30 ml of dry acetone. The reaction mixture was stirred at laboratory temperature for 12 hours, then poured onto ice, and the solid product was sucked off and rinsed with 50% aqueous acetone. The mixture of two substances which was obtained in this manner was separated by column chromatography on a silica gel with a hexane/ethyl-acetate mobile phase (gradient from 100/0 to 50/50). White crystals of the product were always acquired after recrystallization from methanol.

The yield from 440 mg of 2-amino-5-(sec-butyl)-4,6-dichloropyrimidine was:
A) 452 mg of 2-amino-5-(sec-butyl)-4,6-diiodopyrimidine (36); m.p. 173-174° C. ¹H NMR (DMSO-d₆): 7.10 s, 2H, (NH₂); 3.11 m, 1H, (H-1'); 2.00 m, 1H and 1.60 m, 1H(H-2'); 1.25 d, 3H, J(1",1')=7.3 (H-1"); 0.78 t, 3H, J(3',2')=7.5 (H-3'). ¹³C NMR (DMSO-d₆): 159.93 (C-2); 140.94 (C-4 and 6*); 130.01 (C-5); 127.21 (C-4 and 6*); 44.21 (C-1'); 26.90 (C-2'); 18.44 (C-1"); 12.52 (C-3'). * Because of atropoisomery and the present chiral centre (sec-Bu), the substance exhibits two different signals for carbons 4 and 6 of the pyrimidine ring. For C₈H₁₁I₂N₃: calculated: 23.84% C, 2.75% H, 62.98% I, 10.43% N. found: 23.67% C, 2.59% H, 62.70% I, 10.35% N.

GC/MS-EI (R$_T$ 20.36 min), m/z (%): 403 [M$^+$] (36), 374 [M$^+$-Et] (100), min. 99.5% purity.

B) 136 mg 2-amino-5-(sec-butyl)-4-chloro-6-iodopyrimidine (37); m.p. 166-168° C. $^1$H NMR (DMSO-d$_6$): 7.11 s, 2H, (NH$_2$); 3.17 m, 1H, (H-1'); 2.05 m, 1H and 1.63 m, 1H (H-2'); 1.21 d, 3H, J(1",1')=7.3 (H-1"); 0.77 t, 3H, J(3',2')=7.4 (H-3'). $^{13}$C NMR (DMSO-d$_6$): 159.90 (C-2); 155.23 (C-4); 138.50 (C-6); 130.12 (C-5); 44.21 (C-1'); 26.86 (C-2'); 18.41 (C-1"); 12.63 (C-3'). For C$_8$H$_{11}$ClIN$_3$: calculated: 30.84% C, 3.56% H, 11.38% Cl, 40.73% I, 13.49% N. found: 30.68% C, 3.74% H, 13.37% N. GC/MS-EI (R$_T$ 17.97 min), m/z (%): 311 and 313 [M$^+$] (23), 282 and 284 [M$^+$-Et] (100), min. 99.5% purity.

The yield from 508 mg of 2-amino-5-benzyl-4,6-dichloropyrimidine was:

A) 495 mg of 2-amino-5-benzyl-4,6-diiodopyrimidine (38); m.p. 198-199° C. $^1$H NMR (DMSO-d$_6$): 7.30 m, 2H, (H-3'); 7.25 bs, 2H, (NH$_2$); 7.21 m, 1H, (H-4'); 7.11 m, 2H, (H-2'); 4.14 s, 2H, (CH$_2$). $^{13}$C NMR (DMSO-d$_6$): 160.62 (C-2); 137.99 (C-1'), 135.56 (C-4 and 6); 128.66 (C-3'); 128.12 (C-5); 128.04 (C-2'); 126.40 (C-4'); 45.70 (CH$_2$). For C$_{11}$H$_9$I$_2$N$_3$: calculated: 20.23% C, 2.08% H, 58.08% I, 9.62% N. found: 20.46% C, 2.27% H, 57.86% I, 9.40% N. GC/MS-EI (R$_T$ 24.39 min), m/z (%): 437 [M$^+$] (100), min. 99.5% purity.

B) 153 mg 2-amino-5-benzyl-4-chloro-6-iodopyrimidine (39); m.p. 184-184° C. $^1$H NMR (DMSO-d$_6$): 7.36 m, 2H, (H-3'); 7.27 bs, 2H, (NH$_2$); 7.15 m, 1H, (H-4'); 7.13 m, 2H, (H-2'); 4.18 s, 2H, (CH$_2$). $^{13}$C NMR (DMSO-d$_6$): 160.96 (C-2); 138.54 (C-1'), 157.63 (C-4); 138.96 (C-6); 128.36 (C-3'); 128.27 (C-5); 128.00 (C-2'); 126.39 (C-4'); 45.43 (CH$_2$). For C$_{11}$H$_9$ClIN$_3$: calculated: 38.23% C, 2.63% H, 10.26% Cl, 36.72% I, 12.16% N. found: 38.49% C, 2.90% H, 12.02% N. GC/MS-EI (R$_T$ 22.40 min), m/z (%): 345 and 347 [M$^+$] (100), min. 99.5% purity.

For the preparation of 4,6-dibromopyrimidines, the reaction of 4,6-dihydroxypyrimidines with POBr$_3$ in an organic solvent resulting in a NEt$_3$ catalysis was used.

A flask was filled under argon with 4 mmol of the relevant 4,6-dihydroxypyrimidine, 6.88 g (24 mmol) of POBr$_3$ and 50 ml of toluene. Under intensive stirring, 810 mg (8 mmol) triethylamine were slowly added dropwise, yielding a yellow suspension, which was further heated to 120° C. for six hours. After cooling to laboratory temperature, the reaction mixture was poured onto ice and the product extracted by chloroform and subsequently purified by column chromatography on a silica gel with a hexane/ethyl-acetate mobile phase (gradient from 100/0 to 50/50). After the organic solvents evaporated, the product was recrystallized from the hexane/ethyl-acetate mixture.

2-amino-5-benzyl-4,6-dibromopyrimidine (40)

Yield: 273 mg (20% of the theor. yield); m.p. 154-155° C. $^1$H NMR (DMSO-d$_6$): 7.48 bs, 2H, (NH$_2$); 7.21 t, 2H, 7.22 t, 1H and 7.30 d, 2H (phenyl); 4.21 s, 2H, (CH$_2$). $^{13}$C NMR (DMSO-d$_6$): 161.25 (C-2); 146.83 (C-4 and 6); 138.17, 128.70, 127.98 and 126.63 (C-phenyl); 118.43 (C-5); 34.22 (CH$_2$). For C$_{11}$H$_9$Br$_2$N$_3$: calculated: 38.52% C, 2.64% H, 46.59% Br, 12.25% N. found: 38.59% C, 2.81% H, 46.23% Br, 12.05% N. GC/MS-EI (R$_T$ 22.25 min), m/z (%): 341, 343 and 345 [M$^+$] (100), min. 99.5% purity.

Example 5

Preparation of 5-substituted 2-amino-4-aryl-6-chloropyrimidines

For the preparation of 5-substituted 2-amino-4-aryl-6-chloropyrimidines, the method described in the literature [Journal of Medicinal Chemistry 50, 2060-2066, 2007] was used, which was modified to achieve preferably the exchange of one halogen atom and hence suppress to the maximum the creation of the respective diaryl derivatives. The reaction was conducted with only one equivalent of the chemical agent for introducing the aryl residue into the toluene/ethanol mixture, where the addition of ethanol has a positive effect on the selectivity of the reaction.

A flask was filled with always 2 mmol of 5-substituted 2-amino-4,6-dichloropyrimidine, 2 mmol of the relevant arylboronic acid, 92 mg (0.08 mmol) of Pd[P(C$_6$H$_5$)$_3$]$_4$ (tetrakis(triphenylphosphine)palladium) and 234 mg (2.2 mmol) of Na$_2$CO$_3$. The reaction vessel was closed by a septum and subsequently very carefully saturated with argon. After the addition of 10 ml of ethanol and 30 ml of toluene using a needle through the septum, the reaction mixture was heated to 70° C. for four hours. After cooling, the organic solvents were evaporated on a vacuum rotary evaporator and the product was purified by column chromatography with a hexane/ethyl-acetate mobile phase (gradient from 100/0 to 60/40). After recrystallization from the hexane/ethyl-acetate mixture and cooling of the crystallized solution to 0° C., white crystals were isolated, rinsed with 5 ml of hexane and dried in a vacuum drier for one day at room temperature and under of 0.1 mbar.

2-amino-5-butyl-4-chloro-6-phenylpyrimidine (41)

Yield: 494 mg (94% of the theor. yield); m.p. 183-185° C. $^1$H NMR (DMSO-d$_6$): 7.50-7.40 m, 5H, (H-2", 3" and 4"); 6.93 bs, 2H, (NH$_2$); 2.46 m, 2H, 1.35 m, 2H and 1.13 m, 2H (3×CH$_2$); 0.72 t, 3H, J(4',3')=7.4 (H-4'). $^{13}$C NMR (DMSO-d$_6$): 168.81 (C-4); 161.27 and 161.13 (C-2 and 6); 138.72 (C-1"); 128.91 (C-4"); 128.26 and 128.14 (C-2" and C-3"); 118.10 (C-5); 31.35, 27.67, 21.99 (C-1', 2' and 3'); 13.54 (C-4'). For C$_{14}$H$_{16}$ClN$_3$: calculated: 64.24% C, 6.16% H, 13.54% Cl, 16.05% N. found: 64.18% C, 6.28% H, 13.70% Cl, 15.88% N. GC/MS-EI (R$_T$ 20.50 min), m/z (%): 261 and 263 [M$^+$] (28), 218 and 220 [M$^+$-Pr] (100), min. 99.5% purity.

2-amino-5-butyl-4-chloro-6-(thiophen-3-yl)pyrimidine (42)

Yield: 428 mg (80% of the theor. yield); m.p. 154-155° C. $^1$H NMR (DMSO-d$_6$): 7.78 dd, 1H, J(2",5")=2.9, J(2",4")=1.3 (H-2"); 7.63 dd, 1H, J(5",4")=5.0, J(5",2")=2.9 (H-5"); 7.31 dd, 1H, J(4",5")=5.0, J(4",2")=1.3 (H-4"); 6.88 bs, 2H, (NH$_2$); 2.58 m, 2H, 1.41 m, 2H and 1.23 m, 2H (3×CH$_2$); 0.80 t, 3H, J(4'.3')=7.3 (H-4'). $^{13}$C NMR (DMSO-d$_6$): 163.40 (C-6); 161.55 (C-4); 161.16 (C-2); 139.34 (C-3"); 128.45 (C-4"); 126.63 (C-2"); 126.36 (C-5"); 118.03 (C-5); 31.37, 27.89, 22.13 (C-1', 2' and 3'); 13.65 (C-4'). For C$_{12}$H$_{14}$ClN$_3$S: calculated: 53.82% C, 5.27% H, 13.24% Cl, 15.69% N, 11.97% S. found: 53.57% C, 5.44% H, 13.35% Cl, 15.89% N, 11.70% S. GC/MS-EI (R$_T$ 20.98 min), m/z (%): 267 and 269 [M$^+$] (35), 224 and 226 [M$^+$-Pr] (100), min. 99.5% purity.

2-amino-5-butyl-4-chloro-6-(pyridin-3-yl)pyrimidine (43)

Yield: 336 mg (64% of the theor. yield); m.p. 189-190° C. $^1$H NMR (DMSO-d$_6$): 8.66 dd, 1H, J(6",5")=4.9, J(6",4")=1.7 (H-6"); 8.65 d, 1H, J(2",4")=2.2 (H-2"); 7.89 dt, 1H, J(4',5")=7.8, J(4",6")=J(4",2")=2.0 (H-4"); 7.51 dd, 1H, J(5", 4")=7.8, J(5",6")=4.9 (H-5"); 7.04 bs, 2H, (NH$_2$); 2.45 m, 2H, 1.35 m, 2H and 1.13 m, 2H (3×CH$_2$); 0.71 t, 3H, J(4'.3')=7.4 (H-4'). $^{13}$C NMR (DMSO-d$_6$): 165.90 (C-6); 161.49 and 161.22 (C-2 and 4); 149.95 (C-6"); 148.62 (C-2"); 135.87 (C-4"); 134.45 (C-3"); 125.37 (C-5"); 118.53 (C-5); 31.35, 27.61, 21.95 (C-1', 2' and 3'); 13.53 (C-4'). For $C_{13}H_{15}ClN_4$: calculated: 59.43% C, 5.76% H, 13.49% Cl, 21.32% N. found: 59.68% C, 5.58% H, 13.24% Cl, 21.19% N. GC/MS-EI ($R_T$ 21.16 min), m/z (%): 261, 262, 263 and 264 [$M^+$] (57), 219 and 221 [$M^+$-Pr] (100), min. 99.5% purity.

2-amino-4-(benzofuran-2-yl)-5-butyl-6-chloropyrimidine (44)

Yield: 412 mg (68% of the theor. yield); m.p. 195-196° C. $^1$H NMR (DMSO-$d_6$): 7.78 m, 1H, (H-4'); 7.63 m, 1H, (H-7'); 7.52 d, 1H, J(3',7')=0.9 (H-3'); 7.43 m, 1H, (H-6'); 7.33 m, 1H, (H-5'); 7.03 bs, 2H, (NH$_2$); 2.90 m, 2H, 1.53 m, 2H and 1.41 m, 2H (3×CH$_2$); 0.93 t, 3H, J(4",3")=7.3 (H-4"). $^{13}$C NMR (DMSO-$d_6$): 162.77 (C-6); 161.16 (C-2); 155.66 (C-4); 154.84 (C-7a'); 153.52 (C-2'); 127.51 (C-3a'); 126.47 (C-6'); 123.80 (C-5'); 122.52 (C-4'); 117.68 (C-5); 111.62 (C-7'); 110.01 (C-3'); 31.69, 27.70, 22.33 (C-1", 2" and 3"); 13.83 (C-4"). For $C_{16}H_{16}ClN_3O$: calculated: 63.68% C, 5.34% H, 11.75% Cl, 13.92% N. found: 63.45% C, 5.17% H, 11.98% Cl, 13.80% N. GC/MS-EI ($R_T$ 24.04 min), m/z (%): 301 and 303 [$M^+$] (38), 258 and 260 [$M^+$-Pr] (100), min. 99.5% purity.

Other similar 5-substituted 2-amino-4-aryl-6-chloropyrimidines are listed for clarity in Tables 1 and 2.

Example 6

Preparation of Symmetrical 5-substituted 2-amino-4,6-diarylpyrimidines

For the preparation of 5-substituted 2-amino-4,6-diarylpyrimidines, the method described in the literature [Journal of Heterocyclic Chemistry 46, 960, 2009 and Journal of Combinatorial Chemistry 11 (4), 519-522, 2009] was used, which was slightly modified to allow only the creation of the relevant diaryl derivatives. The reaction was conducted with three equivalents of the reagent for the introduction of the aryl residue into the toluene/ethanol mixture.

A flask was filled always with 2 mmol of 5-substituted 2-amino-4,6-dichloropyrimidine, 6 mmol of the relevant arylboronic acid, 184 mg (0.16 mmol) of Pd[P(C$_6$H$_5$)$_3$]$_4$ (tetrakis(triphenylphosphine)palladium) and 636 mg (6 mmol) of Na$_2$CO$_3$. The reaction vessel was closed by a septum and subsequently very carefully dried with argon. After the addition of 10 ml of ethanol and 30 ml of toluene using a needle through the septum, the reaction mixture was heated to 80° C. for four hours. After cooling, the organic solvents were evaporated on a vacuum rotary evaporator and the product was purified by column chromatography with a mobile phase of hexane/ethyl-acetate (gradient from 100/0 to 60/40). After recrystallization from the hexane/ethyl-acetate mixture and cooling of the crystallized solution to 0° C., white crystals were isolated, which were rinsed with 5 ml of hexane and dried in a vacuum drier for one day at room temperature and a under 0.1 mbar.

2-amino-5-butyl-4,6-diphenylpyrimidine (45)

Yield: 574 mg (95% of the theor. yield); m.p. 154-155° C. $^1$H NMR (DMSO-$d_6$): 7.41-7.49 m, 10H, (H-2", 3" and 4"); 6.51 bs, 2H, (NH$_2$); 2.45 m, 2H, 0.95 m, 2H and 0.81 m, 2H (3×CH$_2$); 0.43 t, 3H, J(4',3')=7.3 (H-4'). $^{13}$C NMR (DMSO-$d_6$): 167.84 (C-4 and 6); 161.24 (C-2); 139.84 (C-1"); 128.46 (C-4"); 128.37 and 128.21 (C-2" and C-3"); 118.37 (C-5); 31.98, 26.66, 21.75 (C-1', 2' and 3'); 13.29 (C-4'). For $C_{20}H_{21}N_3$: calculated: 79.17% C, 6.98% H, 13.85% N. found: 79.32% C, 7.08% H, 13.56% N. GC/MS-EI ($R_T$ 23.91 min), m/z (%): 303 [$M^+$] (34), 260 [$M^+$-Pr] (100), min. 99.5% purity.

2-amino-5-butyl-4,6-bis(pyridin-3-yl)pyrimidine (46)

Yield: 530 mg (87% of the theor. yield); m.p. 173-174° C. $^1$H NMR (DMSO-$d_6$): 8.72 dd, 2H, J(2",4")=2.3, J(2',5")=0.7 (H-2"); 8.66 dd, 2H, J(6",5")=4.9, J(6",4")=1.7 (H-6"); 7.95 ddd, 2H, J(4",5")=7.9, J(4",2")=2.3, J(4",6")=1.7 (H-4"); 7.52 ddd, 2H, J(5",4")=7.9, J(5",6")=4.9, J(5",2")=0.7 (H-5"); 6.75 bs, 2H, (NH$_2$); 2.44 m, 2H, 0.97 m, 2H and 0.85 m, 2H (3×CH$_2$); 0.45 t, 3H, J(4'.3')=7.3 (H-4'). $^{13}$C NMR (DMSO-$d_6$): 165.20 (C-4 and 6); 161.43 (C-2); 149.66 (C-6"); 148.86 (C-2"); 135.98 (C-4"); 135.20 (C-3"); 123.38 (C-5"); 119.12 (C-5); 32.00, 26.48, 21.64 (C-1', 2' and 3'); 13.23 (C-4'). For $C_{18}H_{19}N_5$: calculated: 70.80% C, 6.27% H, 22.93% N. found: 70.55% C, 6.42% H, 22.70% N. GC/MS-EI ($R_T$ 25.31 min), m/z (%): 304 and 305 [$M^+$] (100), 262 [$M^+$-Pr] (98), min. 99.5% purity.

2-amino-4,6-bis(benzofuran-2-yl)-5-butylpyrimidine (47)

Yield: 613 mg (80% of the theor. yield); m.p. 142-144° C. $^1$H NMR (DMSO-$d_6$): 7.80 ddd, 2H, J(4',5')=7.8, J(4',6')=1.4, J(4',7')=0.9 (H-4'); 7.67 dq, 2H, J(7',6')=8.3, J(7',5')=J(7',4')= 0.9 (H-7'); 7.53 d, 2H, J(3',7')=1.0 (H-3'); 7.44 ddd, 2H, J(6',7')=8.3, J(6',5')=7.2, J(6',4')=1.4 (H-6'); 7.34 ddd, 2H, J(5',4')=7.8, J(5',6')=7.2, J(5',7')=0.9 (H-5'); 6.80 bs, 2H, (NH$_2$); 3.14 m, 2H, 1.58 m, 2H and 1.42 m, 2H (3×CH$_2$); 0.90 t, 3H, J(4".3")=7.4 (H-4"). $^{13}$C NMR (DMSO-$d_6$): 161.52 (C-2); 156.77 (C-4 and 6); 154.74 (C-7a'); 154.23 (C-2'); 127.68 (C-3a'); 126.15 (C-6'); 123.71 (C-5'); 122.36 (C-4'); 118.60 (C-5); 111.59 (C-7'); 109.35 (C-3'); 33.16, 26.92, 22.41 (C-1", 2" and 3"); 13.79 (C-4"). For $C_{24}H_{21}N_3O_2$: calculated: 75.18% C, 5.52% H, 10.96% N. found: 75.03% C, 5.68% H, 10.75% N. GC/MS-EI ($R_T$ 30.67 min), m/z (%): 383 [$M^+$] (34), 340 [$M^+$-Pr] (100), min. 99.5% purity.

Further 5-substituted 2-amino-4,6-diarylpyrimidines are listed for clarity in Tables 1 and 2.

TABLE 1

Substances prepared from 2-amino-5-butyl-4,6-dichloropyrimidine; the values of the measured MS (EI), m/z.

Structure: X1 and X2 substituents on 5-butyl-2-aminopyrimidine core (H2N at 2-position, X1 at 6, X2 at 4, butyl at 5).

| X2 \ X1 = | Ph-Pyr | 4-F-C6H4-Pyr | 4-OCH3-C6H4-Pyr | 2-Pyridyl-Pyr | 3-Pyridyl-Pyr | 4-Pyridyl-Pyr | 2-Thienyl-Pyr | 2-Furyl-Pyr | 3-Furyl-Pyr | 3-Thienyl-Pyr | Benzofuran-2-yl-Pyr | Benzothiophen-2-yl-Pyr | Naphth-1-yl-Pyr |
|---|---|---|---|---|---|---|---|---|---|---|---|---|---|
| Ph-Pyr | 303 | 321 | 333 | 304 | 304 | 304 | 309 | 293 | 293 | 309 | 343 | 359 | 353 |
| 4-F-C6H4-Pyr | i | 339 | 351 | 322 | 322 | 322 | 327 | 311 | 311 | 327 | 361 | 377 | 371 |
| 4-OCH3-C6H4-Pyr | i | i | 363 | 334 | 334 | 334 | 339 | 323 | 323 | 339 | 373 | 389 | 383 |
| 2-Pyridyl-Pyr | i | i | i | 305 | 305 | 305 | 310 | 294 | 294 | 310 | 344 | 360 | 354 |

TABLE 1-continued

Substances prepared from 2-amino-5-butyl-4,6-dichloropyrimidine; the values of the measured MS (EI), m/z.

| $X_2$ \ $X_1$ = | Ph | 4-F-Ph | 4-OCH₃-Ph | 2-Pyridyl | 3-Pyridyl | 4-Pyridyl | 2-Thienyl | 2-Furyl | 3-Furyl | 3-Thienyl | 2-Benzofuryl | 2-Benzothienyl | 1-Naphthyl |
|---|---|---|---|---|---|---|---|---|---|---|---|---|---|
| 3-Pyridyl-Pyr | i | i | i | i | 305 | 305 | 310 | 294 | 294 | 310 | 344 | 360 | 354 |
| 4-Pyridyl-Pyr | i | i | i | i | i | 305 | 310 | 294 | 294 | 310 | 344 | 360 | 354 |
| 2-Thienyl-Pyr | i | i | i | i | i | i | 315 | 299 | 299 | 315 | 349 | 365 | 359 |
| 2-Furyl-Pyr | i | i | i | i | i | i | i | 283 | 283 | 299 | 333 | 349 | 343 |
| 3-Furyl-Pyr | i | i | i | i | i | i | i | 283 | 283 | 299 | 333 | 349 | 343 |

TABLE 1-continued

Substances prepared from 2-amino-5-butyl-4,6-dichloropyrimidine; the values of the measured MS (EI), m/z.

| $X_2$ \ $X_1$ = | Ph-Pyr | 4-F-C₆H₄-Pyr | 4-OCH₃-C₆H₄-Pyr | 2-Py-Pyr | 3-Py-Pyr | 4-Py-Pyr | 2-thienyl-Pyr | 2-furyl-Pyr | 3-furyl-Pyr | 3-thienyl-Pyr | 2-benzofuryl-Pyr | 2-benzothienyl-Pyr | 1-naphthyl-Pyr |
|---|---|---|---|---|---|---|---|---|---|---|---|---|---|
| 3-thienyl-Pyr | i | 279 | 291 | 262 | 262 | 262 | 267 | 251 | 251 | 315 | 349 | 365 | 359 |
| 2-benzofuryl-Pyr | i | i | i | i | i | i | i | i | i | i | 383 | 399 | 393 |
| 2-benzothienyl-Pyr | i | i | i | i | i | i | i | i | i | i | i | 415 | 409 |
| 1-naphthyl-Pyr | i | i | i | i | i | i | i | i | i | i | i | i | 403 |
| Cl | 261 | 279 | 291 | 262 | 262 | 262 | 267 | 251 | 251 | 267 | 301 | 317 | 311 | i — the same combination as in the upper half of the table

The table of the measured MS (EI), m/z: the value reflects the signal found corresponding to $M^+$. In the spectrum, the signal present was always less than 43 units (mainly with a 100% intensity), corresponding to $[M^+-Pr]$ like with the all of the other 5-butylpyrimidines prepared (see above). With the pyridine-substituted derivatives, a signal was also observed with a mass one unit lower $[M^+-H]$, which is likely to correspond to the dissociation of the zwitterion present. With derivatives containing chlorine, a signal was always observed also with a mass two units higher (with approximately one-third intensity), corresponding to the second isotope of chlorine (and its natural representation). The symmetrical diarylpyrimidines were prepared following the method in Example 8. The monoarylpyrimidines were prepared following the method in Example 7. The asymmetrical diarylpyrimidines were prepared from monoarylpyrimidines using the same charges of reactants as in Example 8.

TABLE 2

Substances prepared from 2-amino-5-benzyl-4,6-dichloropyrimidine; the values of the measured MS (EI), m/z.

| $X_2$ = | $X_1$ = Ph | 4-F-Ph | 4-OCH₃-Ph | 2-Pyridyl | 3-Pyridyl | 4-Pyridyl | 2-Thienyl | 2-Furyl | 3-Furyl | 3-Thienyl | 2-Benzofuryl | 2-Benzothienyl | 1-Naphthyl |
|---|---|---|---|---|---|---|---|---|---|---|---|---|---|
| Ph | 337 | 355 | 367 | 337 | 337 | 337 | 343 | 227 | 227 | 343 | 377 | 393 | 387 |
| 4-F-Ph | i | 373 | 385 | 356 | 356 | 356 | 361 | 345 | 345 | 361 | 395 | 411 | 405 |
| 4-OCH₃-Ph | i | i | 397 | 368 | 368 | 368 | 373 | 357 | 357 | 373 | 407 | 423 | 417 |
| 2-Pyridyl | i | i | i | 339 | 339 | 339 | 344 | 328 | 328 | 344 | 378 | 394 | 388 |

TABLE 2-continued

Substances prepared from 2-amino-5-benzyl-4,6-dichloropyrimidine; the values of the measured MS (EI), m/z.

| X₁ / X₂ | Ph | 4-F-C₆H₄ | 4-OCH₃-C₆H₄ | 2-Pyridyl | 3-Pyridyl | 4-Pyridyl | 2-Thienyl | 2-Furyl | 3-Furyl | 3-Thienyl | Benzofuran-2-yl | Benzothiophen-2-yl | Naphth-1-yl |
|---|---|---|---|---|---|---|---|---|---|---|---|---|---|
| 3-Pyridyl-Pyr | i | i | i | i | 339 | 339 | 344 | 328 | 328 | 344 | 378 | 394 | 388 |
| 4-Pyridyl-Pyr | i | i | i | i | i | 339 | 344 | 328 | 328 | 344 | 378 | 394 | 388 |
| 2-Thienyl-Pyr | i | i | i | i | i | i | 349 | 333 | 333 | 349 | 383 | 399 | 393 |
| 2-Furyl-Pyr | i | i | i | i | i | i | i | i | 317 | 333 | 367 | 383 | 377 |
| 3-Furyl-Pyr | i | i | i | i | i | i | i | 317 | 317 | 333 | 367 | 383 | 377 |

TABLE 2-continued

Substances prepared from 2-amino-5-benzyl-4,6-dichloropyrimidine; the values of the measured MS (EI), m/z.

| $X_1$ / $X_2$ | Ph-Pyr | 4-F-C6H4-Pyr | 4-OCH3-C6H4-Pyr | 2-Pyridyl-Pyr | 3-Pyridyl-Pyr | 4-Pyridyl-Pyr | 2-Thienyl-Pyr | 2-Furyl-Pyr | 3-Furyl-Pyr | 3-Thienyl-Pyr | Benzofuran-2-yl-Pyr | Benzothiophen-2-yl-Pyr | Naphth-1-yl-Pyr |
|---|---|---|---|---|---|---|---|---|---|---|---|---|---|
| 3-Thienyl-Pyr | i | 313 | 325 | 296 | 296 | 296 | 301 | 285 | 285 | 349 | 383 | 399 | 393 |
| Benzofuran-2-yl-Pyr | i | i | i | i | i | i | i | i | i | i | 417 | 433 | 427 |
| Benzothiophen-2-yl-Pyr | i | i | i | i | i | i | i | i | i | i | i | 449 | 443 |
| Naphth-1-yl-Pyr | i | i | i | i | i | i | i | i | i | i | i | i | 437 |
| Cl | 295 | 313 | 325 | 296 | 296 | 296 | 301 | 285 | 285 | 301 | 335 | 351 | 345 | i—the identical combination as in the upper half of the table

The table of the measured MS (EI), m/z: the value reflects the signal found corresponding to [M$^+$]. This signal was in most cases the signal with the greatest intensity. With the pyridine-substituted derivatives, a signal was also observed with a mass one unit lower [M$^+$-H], which is likely to correspond to the dissociation of the zwitterion present. With derivatives containing chlorine, a signal was always observed also with a mass two units higher (with approximately one-third intensity) corresponding to the second isotope of chlorine (and its natural representation). The symmetrical diarylpyrimidines were prepared following the method in Example 8. The monoarylpyrimidines were prepared following the method in Example 7. The asymmetrical diarylpyrimidines were prepared from monoarylpyrimidines using the same charges of reactants as in Example 8.

Example 7

Preparation of 5-substituted 4,6-dichloro-2-formamidopyrimidines

Selective preparation of 5-substituted 2-formamido-4,6-dichloropyrimidines was achieved using an innovative method of partial hydrolysis of 5-substituted 4,6-dichloro-2-{[(dimethylamino)methylene]amino}pyrimidines. A number of various systems of acidic or basic hydrolysis were tested for this method. After thorough optimization, the method of selective hydrolysis of 5-substituted 4,6-dichloro-2-{[(dimethylamino)methylene]amino}pyrimidines into 5-substituted 4,6-dichloro-2-formamidopyrimidines, which is sufficiently selective and enables the preparation of the substances according to this invention also on an industrial scale, was described in the submitted invention application for substances according to this invention. The mentioned method takes advantage of the surprising discovery that silica gel (Merck 9385, 230-400 mesh) is capable of selectively catalyzing the described reaction. The supposed essence of this phenomenon is the acidity and suitable spatial structure of the silica gel used. Through the effect of the releasing dimethylamine, the silica gel is however gradually neutralized and the reaction begins to slow dramatically. For complete conversion, it would be necessary for this reason to use a great amount of silica gel, which limits the industrial applicability of this method. The innovative solution is the addition of less than one equivalent of acetic acid, which binds the dimethylamine being created into dimethylammonium salt. The silica gel hence remains catalytically active and the entire reaction runs to almost full conversion. The use of acetic acid itself by far does not have such a catalytic effect as a mixture of the siligagel and acetic acid. The use of stronger acids (e.g. diluted hydrochloric acid) leads to the formation of 5-substituted 2-amino-4,6-dichloropyrimidines.

Selective preparation of 5-substituted 4,6-dichloro-2-formamidopyrimidines:

A flask was filled with 2 mmol of 5-substituted 4,6-dichloro-2-{[(dimethylamino)methylene]amino}-pyrimidine, 0.5 g of silica gel, 40 mg (2.2 mmol) of water, 15 ml of ethyl-acetate and 114 mg (1.9 mmol) of ice-cold acetic acid. This mixture was stirred at room temperature for two days while reaching an almost 100% conversion of the starting substance selectively into the desired 5-substituted 2-formylamino-4,6-dichloropyrimidine. Subsequently, the reaction mixture was evaporated (under 2 mbar and a bath temperature of 45° C.) on a vacuum rotary evaporator and the solid evaporation residue was poured on sintered glass, which already contained 1 g of silica gel. The content of the cullet was subsequently rinsed with 10 ml of hexane. The desired product was then eluted with an ethyl-acetate/hexane mixture (20/80). After evaporation of the organic solvents, the product was recrystallized from the ethyl-acetate hexane mixture and yielded white (to translucent) crystals. After thorough cooling of the entire mixture to 0° C., the separated crystals were sucked off on the sintered glass and rinsed 3 times with 5 ml of cold hexane. The product was subsequently dried for one day in a vacuum drier at laboratory temperature and under 0.1 mbar.

4,6-dichloro-2-formamido-5-methylpyrimidine (48)

Figure 4:
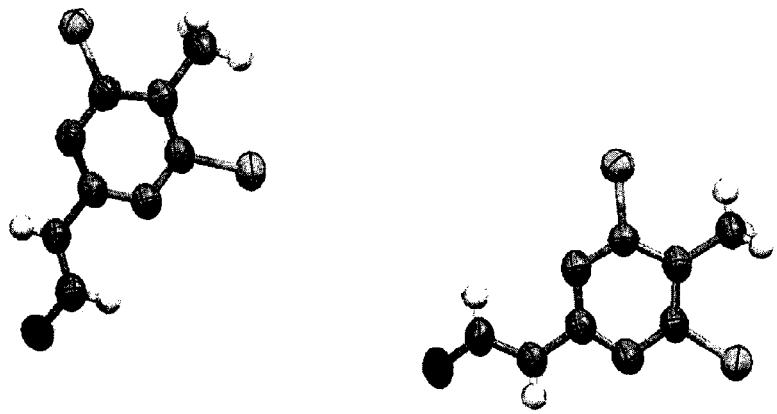
FIG. 4 depicts a graphic interpretation of the measured x-ray structures of substance 48 in the ORTEP (Oak Ridge Thermal-Ellipsoid Plot) format.
Figure 7:
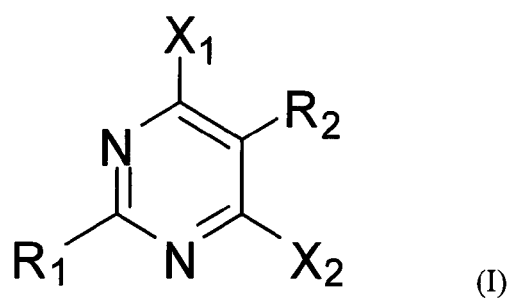
FIG. 7 represents the general formula (I).

Yield: 329 mg (80% of the theor. yield); m.p. 123-124° C. $^1$H NMR (DMSO-d$_6$): 11.36 bs, 1H, (NH); 9.20 bs, 1H, (CHO); 2.31 s, 3H, (H-1'). $^{13}$C NMR (DMSO-d$_6$): 163.12 (CHO); 161.41 (C-4 and 6); 155.00 (C-2); 122.68 (C-5); 15.54 (C-1'). For C$_6$H$_5$Cl$_2$N$_3$O: calculated: 34.98% C, 2.45% H, 34.42% Cl, 20.40% N. found: 34.74% C, 2.43% H, 34.71% Cl, 20.09% N. GC/MS-EI (R$_T$ 17.13 min), m/z (%): 205 and 207 [M$^+$] (21), 177 and 179 [M$^+$-CHO] (100), min. 99.5% purity. For the solution of the X-Ray structure of the crystal of substance 55, see FIG. 4.

4,6-dichloro-5-ethyl-2-formamidopyrimidine (49)

Yield: 345 mg (78% of the theor. yield); m.p. 116-118° C. $^1$H NMR (DMSO-d$_6$): 11.36 bs, 1H, (NH); 9.20 s, 1H, (CHO); 2.74 q, 2H, J(1',2')=7.5 (H-1'); 1.12 t, 3H, J(2',1')=7.5 (H-2'). $^{13}$C NMR (DMSO-d$_6$): 163.05 (CHO); 161.18 (C-4 and 6); 155.18 (C-2); 127.41 (C-5); 22.91 (C-1'); 12.09 (C-2'). For C$_7$H$_7$Cl$_2$N$_3$O: calculated: 38.21% C, 3.21% H, 32.22% Cl, 19.10% N. found: 38.13% C, 3.22% H, 32.66% Cl, 19.04% N. GC/MS-EI (R$_T$ 17.13 min), m/z (%): 219 and 221 [M$^+$] (10), 191 and 193 [M$^+$-CHO] (49), 176 and 178 [M$^+$-CHO and Me] (100), min. 99.5% purity.

4,6-dichloro-2-formamido-5-propylpyrimidine (50)

Yield: 412 mg (88% of the theor. yield); m.p. 92-94° C. $^1$H NMR (DMSO-d$_6$): 11.37 bs, 1H, (NH); 9.21 bs, 1H, (CHO), 2.72 m, 2H, (H-1'); 1.56 m, 2H, (H-2'); 0.96 t, 3H, J(3',2')=7.4 (H-3'). $^{13}$C NMR (DMSO-d$_6$): 163.09 (CHO); 161.46 (C-4 and 6); 155.18 (C-2); 126.09 (C-5); 31.03 (C-1'); 21.00 (C-2'); 13.84 (C-3'). For C$_8$H$_9$Cl$_2$N$_3$O: calculated: 41.05% C, 3.88% H, 30.29% Cl, 17.95% N. found: 41.02% C, 3.92% H, 30.57% Cl, 17.67% N. GC/MS-EI (R$_T$ 18.02 min), m/z (%): 233 and 235 [M$^+$] (9), 205 and 207 [M$^+$-CHO] (37), 176 and 178 [M$^+$-CHO and Et] (100), min. 99.5% purity.

5-butyl-4,6-dichloro-2-formamidopyrimidine (51)

Yield: 423 mg (85% of the theor. yield); m.p. 82-83° C. $^1$H NMR (DMSO-d$_6$): 11.36 bs, 1H, (NH); 9.20 bs, 1H, (CHO); 2.73 m, 2H, (H-1'); 1.50 m, 2H, (H-2'); 1.38 m, 2H (H-3'); 0.92 t, 3H, J(4'.3')=7.2 (H-4'). $^{13}$C NMR (DMSO-d$_6$): 163.03 (CHO); 161.34 (C-4 and 6); 155.14 (C-2); 126.29 (C-5); 29.62 (C-2'); 28.90 (C-1'); 22.10 (C-3'); 13.79 (C-4'). For C$_9$H$_{11}$Cl$_2$N$_3$O: calculated: 43.57% C, 4.47% H, 28.58% Cl, 16.94% N. found: 43.69% C, 4.35% H, 28.39% Cl, 16.65% N. GC/MS-EI (R$_T$ 17.56 min), m/z (%): 247 and 249 [M$^+$] (8), 219 and 221 [M$^+$-CHO] (43), 176 and 178 [M$^+$-CHO and Pr] (100), min. 99.5% purity.

5-(perdeutero-butyl)-4,6-dichloro-2-formamidopyrimidine (52)

Yield: 476 g (93% of the theor. yield); m.p. 83-84° C. $^1$H NMR (DMSO-d$_6$): 11.37 bs, 1H, (NH); 9.20 s, 1H, (CHO).

¹³C NMR (DMSO-d₆): 163.06 (CHO); 161.34 (C-4 and 6); 155.17 (C-2); 126.27 (C-5); 28.29 m, 28.29 m and 20.88 m (C-1', 2' and 3'); 12.72 m (C-4'). For C₉H₂D₉Cl₂N₃O: calculated: 42.03% C, 7.83% H (+D), 27.57% Cl, 16.34% N. found: 42.15% C, 4.18% H, 27.39% Cl, 16.14% N (recalculation of % H to H+D 7.60%). GC/MS-EI (R$_T$ 17.61 min), m/z (%): 256 and 258 [M⁺] (7), 228 and 230 [M⁺-CHO] (41), 178 and 180 [⁺-CHO and derD-Pr] (100), min. 99.5% purity.

4,6-dichloro-2-formamido-5-isopropylpyrimidine (53)

Yield: 417 mg (89% of the theor. yield); m.p. 95-96° C. ¹H NMR (DMSO-d₆): 11.36 bs, 1H, (NH); 9.20 s, 1H, (CHO); 3.58 sept, 1H, J(CH,CH₃)=7.2 (CH); 1.33 d, 6H, J(CH₃,CH)=7.2 (2×CH₃). ¹³C NMR (DMSO-d₆): 163.06 (CHO); 161.10 (C-4 and 6); 154.83 (C-2); 129.97 (C-5); 29.10 (CH); 19.16 (CH₃). For C₈H₉Cl₂N₃O: calculated: 41.05% C, 3.88% H, 30.29% Cl, 17.95% N. found: 40.84% C, 3.90% H, 30.58% Cl, 17.70% N. GC/MS-EI (R$_T$ 17.84 min), m/z (%): 233 and 235 [M⁺] (7), 208 and 207 [M⁺-CHO] (56), 190 and 192 [M⁺-CHO and Me] (100), min. 99.5% purity.

5-(sec-butyl)-4,6-dichloro-2-formamidopyrimidine (54)

Yield: 435 mg (88% of the theor. yield); m.p. 92-93° C. ¹H NMR (DMSO-d₆): 11.37 bs, 1H, (NH); 9.21 s, 1H, (CHO); 3.37 m, 1H, (H-1'); 1.89 m, 1H and 1.71 m, 1H (H-2'); 1.31 d, 3H, J(1".1')=7.2 (H-1"); 0.80 t, 3H, J(3'.2')=7.4 (H-3'). ¹³C NMR (DMSO-d₆): 163.04 (CHO); 154.96 (C-2); C-4 and C-6 not found; 128.63 (C-5); 36.23 (C-1'); 26.28 (C-2'); 17.42 (C-1"); 12.47 (C-3'). For C₉H₁₁Cl₂N₃O: calculated: 43.57% C, 4.47% H, 28.58% Cl, 16.94% N. found: 43.51% C, 4.46% H, 28.50% Cl, 16.86% N. GC/MS-EI (R$_T$ 18.67 min), m/z (%): 247 and 249 [M⁺] (12), 219 and 221 [M⁺-CHO] (63), 190 and 192 [M⁺-CHO and Et] (100), min. 99.5% purity.

4,6-dichloro-2-formamido-5-hexylpyrimidine (55)

Yield: 483 mg (87% of the theor. yield); m.p. 80-81° C. ¹H NMR (DMSO-d₆): 11.37 bs, 1H, (NH); 9.20 bs, 1H, (CHO); 2.72 m, 2H, (H-1'); 1.51 m, 2H, (H-2'); 1.36 m, 2H(H-3'); 1.26-1.32 m, 4H, (H-4' and 5'); 0.86 m, 3H, (H-6'). ¹³C NMR (DMSO-d₆): 163.03 (CHO); 161.33 (C-4 and 6); 155.15 (C-2); 126.28 (C-5); 31.04 (C-4'); 29.19 (C-1'); 28.56 (C-3'); 27.42 (C-2'); 22.16 (C5'); 14.08 (C-6'). For C₁₁H₁₅Cl₂N₃O: calculated: 47.84% C, 5.47% H, 25.68% Cl, 15.22% N. found: 47.94% C, 5.41% H, 25.68% Cl, 15.05% N. GC/MS-EI (R$_T$ 19.73 min), m/z (%): 275 and 277 [M⁺] (5), 247 and 249 [M⁺-CHO] (32), 176 and 178 [M⁺-CHO and Pn] (100), min. 99.5% purity.

4,6-dichloro-2-formamido-5-phenylpyrimidine (56)

Yield: 467 mg (87% of the theor. yield); m.p. 95-96° C. ¹H NMR (DMSO-d₆): 11.55 bs, 1H, (NH); 9.30 bs, 1H, (CHO); 7.53-7.45 m, 3H and 7.38 m, 2H, (phenyl). ¹³C NMR (DMSO-d₆): 163.13 (CHO); 160.90 (C-4 and 6); 156.06 (C-2); 133.18, 129.83, 129.21 and 128.86 (phenyl); 127.49 (C-5). For C₁₁H₇Cl₂N₃O: calculated: 49.28% C, 2.63% H, 26.45% Cl, 15.67% N. found: 49.53% C, 2.70% H, 26.29% Cl, 15.44% N. GC/MS-EI (R$_T$ 20.31 min), m/z (%): 239 and 241 [M⁺-CHO] (100), min. 99.5% purity.

5-allyl-4,6-dichloro-2-formamidopyrimidine (57)

Yield: 385 mg (83% of the theor. yield); m.p. 85-86° C. ¹H NMR (DMSO-d₆): 11.42 bs, 1H, (NH); 9.22 s, 1H, (CHO); 5.86 ddt, 1H, J(2',1')=5.7, J(2',3'cis)=10.2, J(2',3'$_{trans}$)=17.2 (H-2'); 5.11 dq, 1H, J(3'trans,1')=J(gem)=1.6, J(3'trans,2')=17.2 (H-3'$_{trans}$); 5.02 dq, 1H, J(3'cis,1')=J(gem)=1.6, J(3'$_{cis}$,2')=10.2 (H-3'$_{cis}$); 3.50 dt, 2H, J(1',3')=1.7, J(1',2')=5.7 (H-1'). ¹³C NMR (DMSO-d₆): 163.14 (CHO); 161.80 (C-4 and 6); 155.59 (C-2); 132.29 (C-2'); 123.64 (C-5); 117.20 (C-3'); 33.13 (C-1'). For C₈H₇Cl₂N₃O: calculated: 41.40% C, 3.04% H, 30.55% Cl, 18.11% N. found: 41.32% C, 3.30% H, 30.37% Cl, 18.08% N. GC/MS-EI (R$_T$ 18.10 min), m/z (%): 231 and 233 [M⁺] (14), 203 and 205 [M⁺-CHO] (100), min. 99.5% purity.

4,6-dichloro-2-formamido-5-(prop-2-yn-1-yl)pyrimidine (58)

Yield: 386 mg (84% of the theor. yield); m.p. 127-128° C. ¹H NMR (DMSO-d₆): 11.46 bs, 1H, (NH); 9.22 s, 1H, (CHO); 3.69 d, 2H, J(1'.3')=2.7 (H-1'); 3.05 t, 1H, J(3',1')=2.7 (H-3'). ¹³C NMR (DMSO-d₆): 163.18 (CHO); 161.32 (C-4 and 6); 155.87 (C-2); 121.78 (C-5); 78.56 (C-2'); 72.79 (C-3'); 19.51 (C-1'). For C₈H₅Cl₂N₃O: calculated: 41.77% C, 2.19% H, 30.82% Cl, 18.27% N. found: 41.65% C, 2.13% H, 30.89% Cl, 18.12% N. GC/MS-EI (R$_T$ 18.18 min), m/z (%): 229 and 231 [M⁺] (6), 201 and 203 [M⁺-CHO] (100), min. 99.5% purity.

5-benzyl-4,6-dichloro-2-formamidopyrimidine (59)

Yield: 460 mg (82% of the theor. yield); m.p. 93-95° C. ¹H NMR (DMSO-d₆): 11.45 bs, 1H, (NH); 9.24 s, 1H, (CHO); 7.30 m, 2H, 7.22 m, 1H and 7.19 m, 2H (phenyl); 4.16 s, 2H, (CH₂). ¹³C NMR (DMSO-d₆): 163.17 (CHO); 162.17 (C-4 and 6); 155.68 (C-2); 136.87, 128.82, 128.10 and 126.86 (C-phenyl); 124.76 (C-5); 34.54 (CH₂). For C₁₂H₉Cl₂N₃O: calculated: 51.09% C, 3.22% H, 25.13% Cl, 14.89% N. found: 50.88% C, 3.26% H, 25.41% Cl, 14.68% N. GC/MS-EI (R$_T$ 23.00 min), m/z (%): 281 and 283 [M⁺] (37), 253 and 255 [M⁺-CHO] (100), min. 99.5% purity.

A flask was filled with 2.02 g (10 mmol) of 2-amino-4,6-dichloro-5-(prop-2-yn-1-yl)pyrimidine and 10 ml of 2 mol·l⁻¹ (20 mmol) of a solution of the Vilsmeier-Haack-Arnold reagent in chloroform. The reaction mixture was refluxed for eight hours. Having been cooled to laboratory temperature, the reaction mixture was poured onto ice and rapidly neutralized by NaHCO₃. The obtained mixture was quickly transferred into a separatory funnel and immediately extracted by 3×20 ml of chloroform. The organic fractions were connected and dried using MgSO₄. According to TLC, the reaction mixture contained another substance besides 4,6-dichloro-2-{[(dimethylamino)methylene]amino}-5-(prop-2-yn-1-yl)pyrimidine. The acquired mixture was therefore separated by column chromatography with a hexane/ethyl-acetate mobile phase (80/20 to 50/50). After evaporation of the organic solvents, the isolated substances were 686 mg of 4,6-dichloro-2-{[(dimethylamino)methylene]amino}-5-(prop-2-yn-1-yl)pyrimidine, 317 mg of 4,6-dichloro-2-formamido-5-(prop-2-yn-1-yl)pyrimidine and 458 mg of 4,6-dichloro-5-(2-chloroallyl)-2-formamidopyrimidine, which is created by the addition of hydrochloric acid (developed during the reaction) to the triple bond present. The hydrolysis to 2-formamido derivatives did not occur until during the chromatography.

4,6-dichloro-5-(2-chloroallyl)-2-formamidopyrimidine (60)

M.p. 113-115° C. ¹H NMR (DMSO-d₆): 11.48 bs, 1H, (NH); 9.24 s, 1H, (CHO); 5.38 dt, 1H, J(3' a.1')=1.2, J(gem)=

2.3 (H-3'a); 5.31 dt, 1H, J(3'b.1')=1.5, J(gem)=2.3 (H-3'b); 3.84 t, 2H, J(1'.3')=1.4 (H-1'). $^{13}$C NMR (DMSO-d$_6$): 163.19 (CHO); 162.32 (C-4 and 6); 156.07 (C-2); 136.04 (C-2'); 121.46 (C-5); 115.29 (C-3'); 38.40 (C-1'). For C$_8$H$_6$Cl$_3$N$_3$O: calculated: 36.05% C, 2.27% H, 39.91% Cl, 15.77% N. found: 36.19% C, 2.08% H, 39.63% Cl, 15.49% N. GC/MS-EI (R$_T$ 19.77 min), m/z (%): 265, 267 and 269 [M$^+$] (7), 237, 239 and 241 [M$^+$-CHO] (100), min. 99.5% purity.

Example 8

Other Modifications of Position 2 on the Pyrimidine Ring

8A. The Preparation of Derivatives Bearing a Hydrogen Atom or an Alkyl or Aryl Group in Position 2 of the Pyrimidine Ring:

10 mmol of 5-substituted 4,6-dihydroxypyrimidine [prepared following U.S. Pat. No. 6,248,571] were suspended under inert atmosphere in a 40 ml 2 mol·l$^{-1}$ solution of Vilsmeier-Haack-Arnold reagent (0.08 mol=8 equivalents) in chloroform. The reaction mixture was subsequently refluxed for four hours. During this period, the starting substance became completely dissolved and the color of the reaction mixture changed to between yellow and red. Having been cooled to laboratory temperature, the reaction mixture was poured onto ice and quickly neutralized with NaHCO$_3$. The obtained mixture was quickly transferred into a separatory funnel and immediately extracted by 3×20 ml of chloroform. The organic fractions were connected and dried using MgSO$_4$. The chloroform solution obtained in this manner was filtered through a thin layer (ca 0.5 cm) of neutral silica gel and subsequently thoroughly evaporated on a vacuum evaporator with a yield of an oily yellow product. After the addition of a 10 ml mixture of hexane and ether, the product was subjected to ultrasound for 10 min. Having been cooled by iced bath, the crystals were exclusively sucked off and twice rinsed with the hexane and ether mixture. The isolated product was dried in a vacuum drier at room temperature and under 0.1 mbar for one day.

5-butyl-4,6-dichloropyrimidine (61)

Yield: 1.56 g (76% of the theor. yield); m.p. 62-63° C. $^1$H NMR (DMSO-d$_6$): 8.83 s, 1H, (H-1); 2.36 m, 2H, 1.32 m, 2H and 1.24 m, 2H (3×CH$_2$); 0.82 t, 3H, J(4'.3')=7.2 (H-4'). $^{13}$C NMR (DMSO-d$_6$): 163.24 (C-2); 158.12 (C-4 and 6); 120.71 (C-5); 30.47, 28.53 and 22.13 (C-1', 2' and 3'); 13.60 (C-4'). For C$_8$H$_{10}$Cl$_2$N$_2$: calculated: 46.85% C, 4.92% H, 34.57% Cl, 13.66% N. found: 46.78% C, 4.83% H, 34.37% Cl, 13.42% N. MS (EI), m/z (%): 204 and 206 [M$^+$] (34), 161 and 163 [M$^+$-Pr] (100).

5-butyl-4,6-dichloro-2-methylpyrimidine (62)

Yield: 1.78 g (81% of the theor. yield); m.p. 50-51° C. $^1$H NMR (DMSO-d$_6$): 2.86 s, 3H, (CH$_3$); 2.32 m, 2H, 1.37 m, 2H and 1.28 m, 2H (3×CH$_2$); 0.76 t, 3H, J(4'.3')=7.3 (H-4'). $^{13}$C NMR (DMSO-d$_6$): 168.43 (C-2); 161.43 (C-4 and 6); 119.58 (C-5); 30.64, 28.47 and 22.11 (C-1', 2' and 3'); 25.76 (CH$_3$); 13.56 (C-4'). For C$_9$H$_{12}$Cl$_2$N$_2$: calculated: 49.33% C, 5.52% H, 32.36% Cl, 12.79% N. found: 49.20% C, 5.67% H, 32.40% Cl, 12.63% N. MS (EI), m/z (%): 218 and 220 [M$^+$] (44), 175 and 177 [M$^+$-Pr] (100).

8B. The Preparation of Derivatives Bearing in Position 2 of the Pyrimidine Ring a Substituted or Unsubstituted NH$_2$, OH or SH Group by Nucleophile Aromatic Substitution:

The initial 5-substituted 2,4,6-trichloropyrimidines were prepared according to [Chemical & Pharmaceutical Bulletin 54(9), 1248-1253, 2006].

A flask was filled under inert atmosphere with 10 mmol of 5-substituted 2,4,6-trichloropyrimidine, 50 ml of dry acetonitrile, and this mixture was cooled to −30° C. A solution of nucleophile was then slowly added dropwise such that the temperature of the reaction mixture would not surpass −25° C. For the introduction of the substituted NH$_2$ group, 21 mmol of the relevant amine were always used (2.1 equivalents, when one equivalent was used to bind the created HCl) in 20 ml of ethanol.

For the introduction of the substituted OH group, 10 mmol of the relevant sodium alcoholate were used in 20 ml of the corresponding alcohol.

For the introduction of the OH group, 400 mg (10 mmol) of NaOH were used in 20 ml of ethanol.

For the introduction of the substituted SH group, a solution containing 10 mmol of the relevant alkyl- or arylthiol and 680 mg (10 mmol) of sodium ethanolate were used in 20 ml of ethanol.

The reaction was mixed to a constant conversion (according to TLC), always around three hours.

The mixture of the products was subsequently divided by column chromatography on a silica gel with a hexane/chloroform/methanol mobile phase (gradient from 100/0/0 to 50/45/5). The mixture of 2 and 4 substituted derivatives was separated in this manner.

5-butyl-4,6-dichloro-2-(dimethylamino)pyrimidine (63)

Yield: 513 mg (21% of the theor. yield); m.p. 42-45° C. $^1$H NMR (DMSO-d$_6$): 3.09 s, 6H, (CH$_3$); 2.39 m, 2H, 1.34 m, 2H and 1.21 m, 2H (3×CH$_2$); 0.83 t, 3H, J(4'.3')=7.4 (H-4'). $^{13}$C NMR (DMSO-d$_6$): 160.95 (C-4 and 6); 160.87 (C-2); 112.31 (C-5); 37.02 (CH$_3$); 30.75, 28.34 and 22.12 (C-1', 2' and 3'); 13.63 (C-4'). For C$_{10}$H$_{15}$Cl$_2$N$_3$: calculated: 48.40% C, 6.09% H, 28.57% Cl, 16.93% N. found: 48.23% C, 6.31% H, 28.42% Cl, 16.68% N. MS (EI), m/z (%): 247 and 249 [M$^+$] (32), 204 and 206 [M$^+$-Pr] (100)+mono- and di-demethylated fragments (i.e. −15 and −29). Further, 750 mg (30% of the theor. yield) of a second isomer were isolated.

5-butyl-4,6-dichloro-2-methoxypyrimidine (64)

Yield: 477 mg (20% of the theor. yield) of an oily product. $^1$H NMR (DMSO-d$_6$): 3.78 s, 3H, (CH$_3$); 2.42 m, 2H, 1.37 m, 2H and 1.20 m, 2H (3×CH$_2$); 0.86 t, 3H, J(4'.3')=7.3 (H-4'). $^{13}$C NMR (DMSO-d$_6$): 165.16 (C-2); 161.45 (C-4 and 6); 116.31 (C-5); 53.61 (CH$_3$); 30.77, 28.32 and 22.13 (C-1', 2' and 3'); 13.67 (C-4'). For C$_9$H$_{12}$Cl$_2$N$_2$O: calculated: 45.98% C, 5.14% H, 30.16% Cl, 11.91% N. found: 45.74% C, 5.18% H, 30.31% Cl, 11.67% N. MS (EI), m/z (%): 234 and 236 [M$^+$] (28), 191 and 193 [M$^+$-Pr] (100)+mono-demethylated fragments (i.e. −15). Further, 692 mg (29% of the theor. yield) of a second isomer were isolated.

5-butyl-4,6-dichloro-2-hydroxypyrimidine (65)

Yield: 414 mg (19% of the theor. yield); m.p. 73-75° C. $^1$H NMR (DMSO-d$_6$): 8.63 s, 1H, (OH or NH); 2.37 m, 2H, 1.36 m, 2H and 1.24 m, 2H (3×CH$_2$); 0.83 t, 3H, J(4'.3')=7.3 (H-4'). $^{13}$C NMR (DMSO-d$_6$): 164.52 (C-2); 160.37 (C-4 and 6); 108.47 (C-5); 31.03, 28.36 and 22.05 (C-1', 2' and 3'); 13.53 (C-4'). For C$_8$H$_{10}$Cl$_2$N$_2$O: calculated: 43.46% C, 4.56% H, 32.07% Cl, 12.67% N. found: 43.27% C, 4.47% H, 32.16%

Cl, 12.42% N. MS (EI), m/z (%): 220 and 222 [M+] (36), 177 and 179 [M+-Pr] (100). Further, 540 mg (24% of the theor. yield) of a second isomer were isolated.

5-butyl-4,6-dichloro-2-(methylthio)pyrimidine (66)

Yield: 817 mg (32% of the theor. yield) of an oily product. $^1$H NMR (DMSO-$d_6$): 2.44 s, 3H, (CH$_3$); 2.37 m, 2H, 1.36 m, 2H and 1.32 m, 2H (3×CH$_2$); 0.82 t, 3H, J(4'.3')=7.4 (H-4'). $^{13}$C NMR (DMSO-$d_6$): 169.6 (C-2); 161.23 (C-4 and 6); 121.26 (C-5); 30.36, 28.84 and 22.37 (C-1', 2' and 3'); 15.4 (CH$_3$); 13.84 (C-4'). For C$_9$H$_{12}$Cl$_2$N$_2$: calculated: 49.33% C, 5.52% H, 32.36% Cl, 12.79% N. found: 49.20% C, 5.67% H, 32.40% Cl, 12.63% N. MS (EI), m/z (%): 218 and 220 [M+] (44), 175 and 177 [M+-Pr] (100). Further, 540 mg (24% of the theor. yield) of a second isomer were isolated.

II. Biological Activities

In Vitro

Under in vitro conditions, the effect of the pyrimidine compounds according to this invention was tested in terms of the production of nitric oxide (NO) and in terms of the production of prostaglandin E2 (PGE2) in cultures of the peritoneal cells of mice.

Example 9

NO is a product of the metabolism of L-arginine, quickly changes to nitrates, which are then measured using the Griess reagent system. Under normal conditions, the production of NO is practically zero. It only occurs after some stimulation. In these experiments, interferon-gamma (IFN-γ) and bacterial lipopolysacharide (LPS) were used as stimulators. The values of NO induced in this way fluctuated in the individual experiments in a range from 52 to 89 μmol·l$^{-1}$; for the purposes of comparison between the experiments they were considered as 100%. The production of NO after the application of the substances was expressed in percentage with respect to the control values. (The lower the value, the higher the inhibition effect of the substances on NO production.) IC$_{50}$ are the concentrations of the substances reducing the production of NO by 50% with respect to the controls. The results are summarized in Table 3.

Example 10

The influence on the production of prostaglandin E2 (PGE2) in vitro caused by the activity of the pyrimidine compounds according to the submitted invention was determined in cultures of the peritoneal cells of mice using a commercial kit (R&DSystems). The concentrations of PGE2 after lipopolysacharide (LPS) stimulation reached in the individual experiments values in a range of 22 to 91 ng·ml$^{-1}$ and for the purposes of comparison between the experiments were considered as 100%. The influence of the substances on the production of PGE2 was evaluated in percentage with respect to the control values.

Cell viability was determined in the standard way using a WST-1 kit (Roche). The values of the viability of the control cells were for the purposes of comparison between experiments considered as 100%. The influence of the substances on the longevity of the cells was evaluated in percentage with respect to the control values. The results are summarized in Table 3.

TABLE 3A

Production of nitric oxide

| Substance No. | IC$_{50}$ in % of the controls | IC$_{50}$ (μmol·l$^{-1}$) average value and range of values | Production of prostaglandins in % of the controls | Cell viability in % of the controls |
|---|---|---|---|---|
| 13 | 21.39 ± 4.78 (n = 4) | not determined | 59.98 ± 1.82 (n = 2) | 77.29 ± 3.69 (n = 8) |
| 14 | 23.24 ± 6.78 (n = 12) | 13.6/11.8-15.7/ | 30.40 ± 0.80 (n = 2) | 162.93 ± 14.68 (n = 24) |
| 15 | 8.42 ± 4.75 (n = 6) | 14.9/9.7-23.0/ | 14.76 ± 0.52 (n = 4) | 109.35 ± 8.88 (n = 12) |
| 16 | 7.32 ± 2.68 (n = 8) | 8.6/6.6-11.9/ | 32.10 ± 2.31 (n = 6) | 134.83 ± 16.51 (n = 12) |
| 17 | 6.2 ± 0.91 (n = 4) | 3.3/2.7-4.1/ | 15.72 ± 0.46 (n = 4) | 136.13 ± 11.32 (n = 12) |
| 18 | 0.90 ± 0.22 (n = 2) | 4.2/3.5-5.2/ | 78.55 ± 0.38 (n = 2) | 67.89 ± 7.41 (n = 8) |
| 19 | 2.99 ± 0.53 (n = 6) | 5.1/4.2-6.3/ | 14.93 ± 3.11 (n = 4) | 123.21 ± 21.43 (n = 16) |
| 20 | 7.49 ± 13.51 (n = 4) | not determined | not determined | not determined |
| 21 | 0.69 ± 0.12 (n = 4) | 2.6/2.1-3.1/ | 8.14 ± 0.07 (n = 2) | 122.65 ± 14.39 (n = 12) |
| 22 | 61.34 ± 3.91 (n = 4) | not determined | not determined | not determined |
| 23 | 4.41 ± 0.59 (n = 4) | 3.4/2.9-4.0/ | 3.05 ± 1.26 (n = 6) | 96.24 ± 11.9 (n = 12) |
| 24 | 4.97 ± 2.00 (n = 6) | 7.1/4.7-10.7/ | 18.45 ± 13.68 (n = 4) | 80.00 ± 11.61 (n = 16) |
| 25 | 47.30 ± 13.48 (n = 6) | not determined | not determined | 98.55 ± 17.60 (n = 8) |
| 26 | 48.59 ± 9.49 (n = 10) | 146/99-213/ | not determined | 91.53 ± 10.78 (n = 8) |
| 27 | 46.98 ± 10.25 (n = 6) | not determined | 31.73 ± 4.35 (n = 2) | 87.86 ± 9.18 (n = 8) |
| 28 | 53.23 ± 5.79 (n = 20) | not determined | 13.14 ± 0.13 (n = 2) | 100.42 ± 5.77 (n = 12) |
| 29 | 36.97 ± 8.22 (n = 10) | not determined | not determined | 91.18 ± 9.90 (n = 8) |
| 30 | 47.48 ± 6.22 (n = 10) | 160/62-413/ | not determined | 111.90 ± 9.63 (n = 12) |
| 31 | 36.11 ± 8.38 (n = 10) | not determined | not determined | 82.53 ± 8.73 (n = 12) |
| 32 | 41.72 ± 9.27 (n = 8) | 145/173-289/ | 90.81 ± 5.95 (n = 2) | 93.55 ± 19.55 (n = 8) |
| 33 | 35.98 ± 14.08 (n = 6) | not determined | not determined | 90.58 ± 17.05 (n = 8) |
| 34 | 50.57 ± 9.31 (n = 12) | 403/171-948/ | 3.71 ± 2.00 (n = 6) | 105.92 ± 20.65 (n = 12) |
| 36 | 2.80 ± 1.28 (n = 4) | 11.0/5.7-21.5/ | not determined | not determined |
| 37 | 6.67 ± 5.15 (n = 4) | 14.0/8.0-24.6/ | not determined | 49.11 ± 3.29 (n = 4) |
| 38 | 34.80 ± 0.31 (n = 2) | not determined | not determined | 78.60 ± 5.33 (n = 4) |
| 39 | 18.30 ± 7.66 (n = 4) | 24.6/16.7-36.1/ | not determined | 67.81 ± 3.08 (n = 4) |
| 40 | 32.45 ± 10.99 (n = 4) | 26.1/16.9-40.3/ | not determined | 90.18 ± 3.75 (n = 4) |
| 41 | 47.82 ± 6.08 (n = 10) | 44.3/20.9-94.1/ | not determined | 108.24 ± 7.40 (n = 4) |
| 42 | 63.18 ± 0.89 (n = 4) | 85.6/48.5-150.9/ | not determined | 157.36 ± 5.16 (n = 4) |
| 43 | 58.68 ± 0.92 (n = 4) | 67.8/44.4-103.7/ | not determined | 166.77 ± 22.51 (n = 4) |
| 44 | 62.62 ± 0.19 (n = 4) | 68.6/39.0-120.7/ | not determined | 147.78 ± 5.90 (n = 4) |
| 45 | 73.29 ± 1.40 (n = 4) | 111.8/62.3-200.7/ | not determined | 297.33 ± 23.17 (n = 4) |
| 46 | 70.00 ± 4.82 (n = 4) | 92.5/42.8-199.5/ | not determined | 107.08 ± 2.94 (n = 4) |
| 47 | 41.23 ± 18.49 (n = 4) | 20.5/12.1-34.8/ | not determined | 75.01 ± 13.63 (n = 4) |
| 48 | 1.35 ± 0.01 (n = 4) | not determined | 36.31 ± 1.99 (n = 2) | 66.37 ± 8.13 (n = 8) |
| 49 | 5.76 ± 2.48 (n = 6) | 11.5/8.0-16.4/ | 20.58 ± 2.13 (n = 2) | 111.37 ± 10.44 (n = 8) |

TABLE 3A-continued

Production of nitric oxide

| Substance No. | in % of the controls | IC$_{50}$ (μmol · l$^{-1}$) average value and range of values | Production of prostaglandins in % of the controls | Cell viability in % of the controls |
|---|---|---|---|---|
| 50 | 3.95 ± 2.27 (n = 4) | 11.6/8.5-15.8/ | 14.20 ± 7.00 (n = 4) | 98.59 ± 6.59 (n = 8) |
| 51 | 8.37 ± 2.77 (n = 8) | 3.9/2.8-5.4/ | 5.22 ± 2.66 (n = 4) | 92.15 ± 9.90 (n = 12) |
| 52 | 10.40 ± 2.79 (n = 10) | 7.7/4.1-14.6/ | not determined | 123.88 ± 12.50 (n = 4) |
| 53 | 0.70 ± 0.22 (n = 6) | 2.8/1.8-4.2/ | 8.57 ± 0.99 (n = 2) | 60.02 ± 0.29 (n = 12) |
| 54 | 0.17 ± 0.17 (n = 4) | 3.3/2.3-5.0/ | 30.48 ± 1.79 (n = 2) | 77.51 ± 14.73 (n = 8) |
| 55 | 14.77 ± 9.19 (n = 8) | 12.6/6.9-23.2/ | not determined | 144.97 ± 18.27 (n = 4) |
| 56 | 0.80 ± 0.37 (n = 8) | 2.8/1.9-3.9/ | 46.40 ± 0.28 (n = 2) | 48.49 ± 4.44 (n = 16) |
| 57 | 1.21 ± 0.28 (n = 6) | 1.1/1.0-1.3/ | 16.42 ± 0.64 (n = 2) | 95.37 ± 15.40 (n = 20) |
| 58 | 0.69 ± 0.26 (n = 6) | 1.9/1.3-2.9/ | 12.30 ± 0.54 (n = 2) | not determined |
| 59 | 0.15 ± 0.01 (n = 6) | 2.9/2.3-3.7/ | 3.84 ± 0.11 (n = 2) | 58.75 ± 5.34 (n = 20) |
| 60 | 0.13 ± 0.13 (n = 2) | not determined | not determined | 37.13 ± 1.27 (n = 4) |
| 61 | 27.38 ± 1.88 (n = 2) | not determined | not determined | 73.73 ± 0.99 (n = 4) |
| 62 | 41.21 ± 5.50 (n = 2) | not determined | not determined | 80.93 ± 0.84 (n = 4) |
| 63 | 64.97 ± 2.92 (n = 2) | not determined | not determined | not determined |

The following substances, prepared as described in Example 6, were also tested:

2-amino-5-butyl-4,6-diphenylpyrimidine (67)
2-amino-5-butyl-4-chloro-6-phenylpyrimidine (68)
2-amino-5-butyl-4-(4-fluorophenyl)-6-phenylpyrimidine (69)
2-amino-5-butyl-4,6-bis(4-fluorophenyl)pyrimidine (70)
2-amino-5-butyl-4-chloro-6-(4-fluorophenyl)pyrimidine (71)
2-amino-5-butyl-4-(4-methoxyphenyl)-6-phenylpyrimidine (72)
2-amino-5-butyl-4-(4-fluorophenyl)-6-(4-methoxyphenyl)pyrimidine (73)
2-amino-5-butyl-4,6-bis(4-methoxyphenyl)pyrimidine (74)
2-amino-5-butyl-4-chloro-6-(4-methoxyphenyl)pyrimidine (75)
2-amino-5-butyl-4-phenyl-6-(pyridin-2-yl)pyrimidine (76)
2-amino-5-butyl-4-(4-methoxyphenyl)-6-(pyridin-2-yl)pyrimidine (77)
2-amino-5-butyl-4-phenyl-6-(pyridin-3-yl)pyrimidine (78)
2-amino-5-butyl-4-(4-fluorophenyl)-6-(pyridin-3-yl)pyrimidine (79)
2-amino-5-butyl-4-(4-methoxyphenyl)-6-(pyridin-3-yl)pyrimidine (80)
2-amino-5-butyl-4,6-bis(pyridin-3-yl)pyrimidine (81)
2-amino-5-butyl-4-chloro-6-(pyridin-3-yl)pyrimidine (82)
2-amino-5-butyl-4-(4-methoxyphenyl)-6-(pyridin-4-yl)pyrimidine (83)
2-amino-5-butyl-4-(pyridin-3-yl)-6-(pyridin-4-yl)pyrimidine (84)
2-amino-5-butyl-4-chloro-6-(pyridin-4-yl)pyrimidine (85)
2-amino-5-butyl-4-phenyl-6-(thiophen-2-yl)pyrimidine (86)
2-amino-5-butyl-4-(4-fluorophenyl)-6-(thiophen-2-yl)pyrimidine (87)
2-amino-5-butyl-4-(4-methoxyphenyl)-6-(thiophen-2-yl)pyrimidine (88)
2-amino-5-butyl-4-(pyridin-2-yl)-6-(thiophen-2-yl)pyrimidine (89)
2-amino-5-butyl-4-(pyridin-3-yl)-6-(thiophen-2-yl)pyrimidine (90)
2-amino-5-butyl-4-(pyridin-4-yl)-6-(thiophen-2-yl)pyrimidine (91)
2-amino-5-butyl-4,6-bis(thiophen-2-yl)pyrimidine (92)
2-amino-5-butyl-4-chloro-6-(thiophen-2-yl)pyrimidine (93)
2-amino-5-butyl-4-(furan-2-yl)-6-phenylpyrimidine (94)
2-amino-5-butyl-4-(4-fluorophenyl)-6-(furan-2-yl)pyrimidine (95)
2-amino-5-butyl-4-(furan-2-yl)-6-(4-methoxyphenyl)pyrimidine (96)
2-amino-5-butyl-4-(furan-2-yl)-6-(pyridin-3-yl)pyrimidine (97)
2-amino-5-butyl-4-(furan-2-yl)-6-(pyridin-4-yl)pyrimidine (98)
2-amino-5-butyl-4-(furan-2-yl)-6-(thiophen-2-yl)pyrimidine (99)
2-amino-5-butyl-4,6-bis(furan-2-yl)pyrimidine (100)
2-amino-5-butyl-4-chloro-6-(furan-2-yl)pyrimidine (101)
2-amino-5-butyl-4-(furan-3-yl)-6-phenylpyrimidine (102)
2-amino-5-butyl-4-(4-fluorophenyl)-6-(furan-3-yl)pyrimidine (103)
2-amino-5-butyl-4-(furan-3-yl)-6-(4-methoxyphenyl)pyrimidine (104)
2-amino-5-butyl-4,6-bis(furan-3-yl)pyrimidine (105)
2-amino-5-butyl-4-chloro-6-(furan-3-yl)pyrimidine (106)
2-amino-5-butyl-4-phenyl-6-(thiophen-3-yl)pyrimidine (107)
2-amino-5-butyl-4-(4-fluorophenyl)-6-(thiophen-3-yl)pyrimidine (108)
2-amino-5-butyl-4-(4-methoxyphenyl)-6-(thiophen-3-yl)pyrimidine (109)
2-amino-5-butyl-4-(pyridin-3-yl)-6-(thiophen-3-yl)pyrimidine (110)
2-amino-5-butyl-4-(thiophen-2-yl)-6-(thiophen-3-yl)pyrimidine (111)
2-amino-5-butyl-4-(furan-2-yl)-6-(thiophen-3-yl)pyrimidine (112)
2-amino-5-butyl-4-(furan-3-yl)-6-(thiophen-3-yl)pyrimidine (113)
2-amino-5-butyl-4,6-bis(thiophen-3-yl)pyrimidine (114)
2-amino-5-butyl-4-chloro-6-(thiophen-3-yl)pyrimidine (115)
2-amino-4-(benzofuran-2-yl)-5-butyl-6-phenylpyrimidine (116)
2-amino-4-(benzofuran-2-yl)-5-butyl-6-(4-methoxyphenyl)pyrimidine (117)
2-amino-4-(benzofuran-2-yl)-5-butyl-6-(pyridin-2-yl)pyrimidine (118)
2-amino-4-(benzofuran-2-yl)-5-butyl-6-(pyridin-3-yl)pyrimidine (119)
2-amino-4-(benzofuran-2-yl)-5-butyl-6-(pyridin-4-yl)pyrimidine (120)
2-amino-4-(benzofuran-2-yl)-5-butyl-6-(thiophen-2-yl)pyrimidine (121)
2-amino-4-(benzofuran-2-yl)-5-butyl-6-(furan-2-yl)pyrimidine (122)
2-amino-4-(benzofuran-2-yl)-5-butyl-6-(furan-3-yl)pyrimidine (123)
2-amino-4-(benzofuran-2-yl)-5-butyl-6-(thiophen-3-yl)pyrimidine (124)
2-amino-4,6-bis(benzofuran-2-yl)-5-butylpyrimidine (125)

2-amino-4-(benzofuran-2-yl)-5-butyl-6-chloropyrimidine (126)
2-amino-4-(benzo[b]thiophen-2-yl)-5-butyl-6-(pyridin-2-yl)pyrimidine (127)
2-amino-4-(benzo[b]thiophen-2-yl)-5-butyl-6-(pyridin-3-yl)pyrimidine (128)
2-amino-4-(benzo[b]thiophen-2-yl)-5-butyl-6-(pyridin-4-yl)pyrimidine (129)
2-amino-4-(benzo[b]thiophen-2-yl)-5-butyl-6-(thiophen-2-yl)pyrimidine (130)
2-amino-4-(benzo[b]thiophen-2-yl)-5-butyl-6-(furan-2-yl)pyrimidine (131)
2-amino-4-(benzo[b]thiophen-2-yl)-5-butyl-6-chloropyrimidine (132)
2-amino-5-butyl-4-(naphthalen-1-yl)-6-phenylpyrimidine (133)
2-amino-5-butyl-4-(4-methoxyphenyl)-6-(naphthalen-1-yl)pyrimidine (134)
2-amino-5-butyl-4-(naphthalen-1-yl)-6-(pyridin-2-yl)pyrimidine (135)
2-amino-5-butyl-4-(naphthalen-1-yl)-6-(pyridin-3-yl)pyrimidine (136)
2-amino-5-butyl-4-(naphthalen-1-yl)-6-(pyridin-4-yl)pyrimidine (137)
2-amino-5-butyl-4-(furan-2-yl)-6-(naphthalen-1-yl)pyrimidine (138)
2-amino-5-butyl-4-(furan-3-yl)-6-(naphthalen-1-yl)pyrimidine (139)
2-amino-5-butyl-4-(naphthalen-1-yl)-6-(thiophen-3-yl)pyrimidine (140)
2-amino-5-butyl-4,6-bis(naphthalen-1-yl)pyrimidine (141)
2-amino-5-butyl-4-chloro-6-(naphthalen-1-yl)pyrimidine (142)
5-butyl-4,6-dichloro-2-(N-cyclopropylamino)pyrimidine (143)
5-butyl-4,6-dichloro-2-[N-(furan-2-ylmethyl)amino]pyrimidine (144)
2-(N-benzylamino)-5-butyl-4,6-dichloropyrimidine (145)
5-butyl-4,6-dichloro-2-hydrazinylpyrimidine hydrochloride (146)
2-acetamido-5-butyl-4,6-dichloropyrimidine (147)
5-butyl-4,6-dichloro-2-(phenylthio)pyrimidine (148)
5-butyl-4,6-dichloro-2-mercaptopyrimidine (149)

Their activities are summarized in Table 3B:

TABLE 3B

| Subst. No. | Production of nitric oxide in % of the controls | Production of prostaglandins IC$_{50}$ ($\mu$mol · l$^{-1}$) average value and range of values | Cell viabilities in % of the controls |
|---|---|---|---|
| 67 | 80.37 ± 1.36; n = 4 | 76.75 ± 10.63; n = 4 | 93.60 ± 2.81; n = 4 |
| 68 | 27.78 ± 2.11; n = 4 | 18.12 ± 0.99; n = 6 | 94.17 ± 8.43; n = 8 |
| 69 | 71.24 ± 4.28; n = 4 | 75.40 ± 21.62; n = 4 | 121.04 ± 9.53; n = 4 |
| 70 | 87.03 ± 3.75; n = 4 | 51.70 ± 13.80; n = 2 | 108.03 ± 9.80; n = 4 |
| 71 | 37.07 ± 6.31; n = 4 | 26.66 ± 11.71; n = 4 | 94.59 ± 7.75; n = 4 |
| 72 | 55.45 ± 12.92; n = 6 | 3.61 ± 0.22; n = 4 | 108.35 ± 5.66; n = 8 |
| 73 | 65.09 ± 4.11; n = 6 | 3.92 ± 1.85; n = 4 | 130.12 ± 10.97; n = 12 |
| 74 | 86.27 ± 4.16; n = 4 | 38.22 ± 5.59; n = 2 | 98.75 ± 5.63; n = 12 |
| 75 | 15.96 ± 4.83; n = 4 | 4.7 ± 1.17; n = 4 | 86.35 ± 9.29; n = 8 |
| 76 | 45.05 ± 3.55; n = 4 | 42.94 ± 11.04; n = 6 | 97.97 ± 5.33; n = 8 |
| 77 | 58.20 ± 5.42; n = 6 | 13.48 ± 1.94; n = 4 | 100.86 ± 11.78; n = 4 |
| 78 | 52.81 ± 2.91; n = 4 | 59.49 ± 9.09; n = 2 | 78.08 ± 5.20; n = 4 |
| 79 | 62.58 ± 2.32; n = 6 | 47.26 ± 5.67; n = 2 | 104.50 ± 6.37; n = 8 |
| 80 | 35.18 ± 4.39; n = 4 | 41.84 ± 7.54; n = 2 | 103.13 ± 4.24; n = 8 |
| 81 | 50.07 ± 3.04; n = 6 | 51.26 ± 0.45; n = 2 | 82.21 ± 7.34; n = 8 |
| 82 | 12.07 ± 2.39; n = 8 | 92.02 ± 8.95; n = 4 | 45.38 ± 2.92; n = 12 |
| 83 | 63.81 ± 5.32; n = 6 | 82.76/2.12; n = 2 | 95.41 ± 4.70; n = 8 |
| 84 | 47.55 ± 7.12; n = 6 | 77.37/9.47; n = 2 | 109.54 ± 4.48; n = 8 |
| 85 | 49.34 ± 4.20; n = 4 | 61.11/0.00; n = 2 | 87.62 ± 6.58; n = 4 |
| 86 | 47.57 ± 8.58; n = 6 | 27.57 ± 8.77; n = 4 | 101.59 ± 9.19; n = 8 |
| 87 | 48.59 ± 10.92; n = 3 | 23.05 ± 11.33; n = 4 | 125.94 ± 4.49; n = 8 |
| 88 | 69.14 ± 9.10; n = 2 | 14.19 ± 4.00; n = 6 | 125.52 ± 5.28; n = 8 |
| 89 | 19.62 ± 4.08; n = 6 | 92.30 ± 9.20; n = 4 | 104.15 ± 10.36; n = 8 |
| 90 | 50.11 ± 3.95; n = 4 | 31.93 ± 15.87; n = 4 | 69.80 ± 6.79; n = 4 |
| 91 | 63.95 ± 2.00; n = 4 | 29.01 ± 5.46; n = 4 | 81.38 ± 6.86; n = 4 |
| 92 | 46.09 ± 7.92; n = 6 | 29.52 ± 11.77; n = 4 | 102.36 ± 6.45; n = 8 |
| 93 | 59.51 ± 6,63; n = 4 | 11.47 ± 2.73; n = 4 | 74.47 ± 0.81; n = 4 |
| 94 | 39.73 ± 5.57; n = 6 | 38.84 ± 15.99; n = 4 | 104.21 ± 14.38; n = 8 |
| 95 | 61.96 ± 6.41; n = 6 | 70.79 ± 11.61; n = 4 | 119.71 ± 4.71; n = 8 |
| 96 | 50.99 ± 2.60; n = 4 | 43.05 ± 21.74; n = 4 | 113.53 ± 4.93; n = 8 |
| 97 | 37.05 ± 6.68; n = 6 | 48.18 ± 19.94; n = 4 | 45.54 ± 4.96; n = 8 |
| 98 | 54.42 ± 2.64; n = 6 | 62.49 ± 11.98; n = 4 | 69.84 ± 3.62; n = 8 |
| 99 | 31.27 ± 2.12; n = 4 | 13.25 ± 6.33; n = 4 | 55.22 ± 5.10; n = 4 |
| 100 | 33.70 ± 2.71; n = 6 | 22.46 ± 7.25; n = 2 | 69.04 ± 4.47; n = 8 |
| 101 | 29.35 ± 6.38; n = 6 | 6.60 ± 5.34; n = 4 | 68.95 ± 3.02; n = 8 |
| 102 | 68.34 ± 4.63; n = 6 | 54.8 ± 10.70; n = 6 | 110.35 ± 5.69; n = 8 |
| 103 | 66.44 ± 3.19; n = 6 | 66.80 ± 8.64; n = 4 | 147.62 ± 3.25; n = 8 |
| 104 | 71.20 ± 2.85; n = 6 | 57.52 ± 12.44; n = 6 | 137.10 ± 2.72; n = 12 |
| 105 | 49.07 ± 4.67; n = 4 | 50.30 ± 9.52; n = 4 | 101.86 ± 5.13; n = 4 |
| 106 | 54.83 ± 2.82; n = 4 | 22.10 ± 3.44; n = 4 | 100.38 ± 5.55; n = 8 |
| 107 | 69.69 ± 6.09; n = 4 | 68.07 ± 2.56; n = 4 | 69.08 ± 1.78; n = 4 |
| 108 | 64.92 ± 2.30; n = 4 | 47.21 ± 2.59; n = 2 | 124.71 ± 15.20; n = 4 |
| 109 | 73.38 ± 4.58; n = 6 | 4.9 ± 1.72; n = 4 | 120.58 ± 7.53; n = 8 |
| 110 | 62.00 ± 2.93; n = 4 | 64.72 ± 14.00; n = 2 | 90.73 ± 10.89; n = 4 |
| 111 | 57.52 ± 1.81; n = 4 | 56.94 ± 12.51; n = 6 | 105.47 ± 5.51; n = 8 |
| 112 | 47.96 ± 4.90; n = 6 | 55.24 ± 7.98; n = 4 | 92.77 ± 7.75; n = 12 |
| 113 | 63.79 ± 1.64; n = 6 | 85.05 ± 9.96; n = 4 | 101.51 ± 12.74; n = 8 |
| 114 | 70.51 ± 5.78; n = 4 | 37.00 ± 16.33; n = 4 | 118.67 ± 2.26; n = 8 |
| 115 | 37.43 ± 8.29; n = 6 | 22.90 ± 11.94; n = 4 | 107.17 ± 2.03; n = 8 |
| 116 | 72.69 ± 10.36; n = 4 | 49.17 ± 9.72; n = 4 | 95.24 ± 4.78; n = 8 |
| 117 | 89.91 ± 4.02; n = 6 | 64.65 ± 4.88; n = 2 | 75.92 ± 9.72; n = 8 |
| 118 | 56.53 ± 3.33; n = 8 | 52.17 ± 14.96; n = 6 | 91.38 ± 4.41; n = 8 |
| 119 | 70.13 ± 10.10; n = 6 | 71.89 ± 0.36; n = 2 | 76.10 ± 6.23; n = 8 |
| 120 | 65.32 ± 3.72; n = 4 | 83.44 ± 11.03; n = 2 | 92.51 ± 2.77; n = 4 |
| 121 | 55.17 ± 7.88; n = 10 | 62.54 ± 21.79; n = 6 | 90.22 ± 7.99; n = 12 |
| 122 | 35.04 ± 5.71; n = 6 | 68.47 ± 8.71; n = 2 | 81.66 ± 4.41; n = 8 |
| 123 | 11.15 ± 2.99; n = 6 | 35.10 ± 14.56; n = 4 | 42.62 ± 11.49; n = 12 |
| 124 | 33.45 ± 13.04; n = 6 | 62.48 ± 5.45; n = 2 | 94.41 ± 9.01; n = 8 |
| 125 | 67.76 ± 6.80; n = 6 | 73.07 ± 1.91; n = 2 | 76.82 ± 8.89; n = 8 |
| 126 | 78.18 ± 9.03; n = 4 | 87.25 ± 13.99; n = 2 | 102.56 ± 5.92; n = 4 |
| 127 | 40.88 ± 6.83; n = 4 | 38.26 ± 14.52; n = 8 | 130.66 ± 2.87; n = 8 |
| 128 | 64.91 ± 6.60 n = 4 | 31.10 ± 10.43; n = 4 | 79.62 ± 4.12; n = 8 |
| 129 | 63.94 ± 1.84 n = 4 | 65.97 ± 25.34; n = 2 | 85.12 ± 0.76; n = 8 |
| 130 | 43.43 ± 7.18; n = 10 | 56.31 ± 19.61; n = 8 | 130.68 ± 8.17; n = 12 |
| 131 | 49.76 ± 4.85; n = 4 | 83.56 ± 5.83; n = 4 | 98.88 ± 1.65; n = 8 |
| 132 | 49.61 ± 6.36; n = 4 | 20.76 ± 9.35; n = 4 | 84.08 ± 4.71; n = 8 |
| 133 | 49.60 ± 9.26; n = 4 | 61.74 ± 17.48; n = 2 | 110.75 ± 3.69; n = 4 |
| 134 | 33.09 ± 7.25; n = 8 | 27.85 ± 10.82; n = 8 | 93.40 ± 5.59; n = 12 |
| 135 | 18.45 ± 5.66; n = 6 | 28.69 ± 0.00; n = 2 | 64.97 ± 12.85; n = 8 |
| 136 | 70.28 ± 3.71; n = 4 | 72.55 ± 19.06; n = 2 | 111.00 ± 0.97; n = 4 |
| 137 | 58.04 ± 6.68; n = 4 | 28.00 ± 9.43; n = 2 | 85.07 ± 1.02; n = 4 |
| 138 | 42.92 ± 3.77; n = 4 | 43.57 ± 4.53; n = 2 | 93.61 ± 5.46; n = 4 |
| 139 | 70.38 ± 4.95; n = 6 | 18.35 ± 3.26; n = 4 | 104.41 ± 10.83; n = 8 |
| 140 | 30.16 ± 2.96; n = 4 | 40.66 ± 6.87; n = 2 | 94.34 ± 2.62; n = 4 |
| 141 | 57.66 ± 6.53; n = 6 | 34.2 ± 8.01; n = 4 | 107.73 ± 5.36; n = 8 |
| 142 | 43.99 ± 6.06; n = 6 | 9.14 ± 2.71; n = 4 | 114.07 ± 8.00; n = 8 |
| 143 | 78.33 ± 13.82; n = 6 | 85.94 ± 12.69; n = 4 | 104.31 ± 8.28; n = 8 |
| 144 | 83.33 ± 11.72; n = 6 | 0.20 ± 0.33; n = 4 | 150.27 ± 4.96; n = 8 |
| 145 | 93.01 ± 9.25; n = 6 | 0.28 ± 0.23; n = 4 | 147.31 ± 4.88; n = 8 |
| 146 | 86.28 ± 9.01; n = 6 | 1.61 ± 0.27; n = 4 | 103.28 ± 4.62; n = 8 |
| 147 | 15.32 ± 2.33; n = 6 | 80.60 ± 4.63; n = 2 | 113.28 ± 8.99; n = 8 |
| 148 | 61.85 ± 10.25; =10 | 77.50 ± 16.19; n = 4 | 90.49 ± 4.62; n = 12 |
| 149 | 24.12 ± 11.22; n = 6 | 26.35 ± 10.89; n = 4 | 99.14 ± 6.73; n = 8 |

Experiments were performed on mice peritoneal cells C57BL/6 (Charles River, Germany—AnLabu).

NO production was induced using IFN-g (5000 pg/mL) plus LPS (100 pg/mL); evaluated (Griess reagent) after 24 h of the cell cultivation (2×10$^6$/mL). PGE2 was induced using LPS (10 ng/mL); evaluated (ELISA) following 6 h cultivation of cells (3×10$^6$/mL). Cell longevity was evaluated using WST-1 (tetrazolium salt), following 24 h cultivation of cells ($1\times10^6$/mL). The values mentioned in the table represent the effects of the substances tested in a concentration of 50 µmol·l$^{-1}$.

The substances are characterized by a unique selective effect. They inhibit the production of nitric oxide and prostaglandin PGE2 but do not inhibit the production of cytokines. The secretion of these fundamental mediators of immunity was determined in in vitro conditions with the peritoneal cells of mice, which were cultivated in the same way as was described in the case of the production of nitric oxide. The production of cytokines was evoked using bacterial lipopolysacharide (LPS, *E. coli*). The concentration of cytokines in the cell supernatants was determined by the ELISA method, which utilizes commercially available immunochemicals and is described in the literature [Eur. J. Pharmacol. 574, 2007, 77-81; Nitric Oxide 17, 2007, 160-169]. The substances mentioned in Table 3 did not change the production of the following cytokines and chemokines: tumor necrosis factor-alpha (TNF-α), interleukin-1beta (IL-1β), interleukin-6 (IL-6), RANTES and MIP-1α and hence show a highly selective effect only on the reduction of the production of NO and prostaglandin E2.

Example 11

With compound 28, its possible mutagenicity (genotoxicity) was assessed using the standard bacterial reverse mutation test. According to Council Regulation (ES) No. 440/2008, stipulating the test methods according to the European Parliament and Council regulation (ES), the method used was B.13/14, Mutagenicity—Reverse Mutation Test Using Bacteria, which is described in the same way also in the OECD Test Guideline No. 471.

Two indicators were used of the strain *Salmonella typhimurium* (types TA 98 and TA 100) and one indicator of the strain *Escherichia coli* WP2 uvrA in amounts of 20 to 2000 µg, spread on (agar) plates with a medium of 0.1 ml. The experiments were conducted without using metabolic activation and after activation with supernatant S9 from sewer rat livers and with mixtures of cofactors (NADP and glucoso-6-phosphate) to determine the mutagenicity of the metabolic products of the compound tested. Supernatant S9 was prepared according to the literature [Mutat. Res. 113, 173-215, 1983].

The principle of the test is to detect possible revertants created by reverse mutation, which would be induced in the bacterial culture by the tested compound. Specially constructed bacterial strains are used, carrying mutations in the place for his (trp), which are not capable of forming colonies on the minimum plates without histidine or tryptophan. The revertants created differ from these original mutants in the ability to synthesize histidine (tryptophan) and subsequently grow on plates with a selective minimum of glucose. Mutagenic potential is given by the growing number of revertants in the influenced groups in comparison with a negative control, and/or in dependence on the growing number of revertants on the dose of the tested compound.

Bacterial testers, types *Salmonella typhimurium* TA 98 (CCM 3811) and *Escherichia coli* WP2 uvrA (CCM 4751), were acquired from the Czech Collection of Microorganisms of Masaryk University, Brno and the strain *Salmonella typhimurium* TA100 (CIP 103796, lot No. 1008) from the Biological Resource Center, Institut Pasteur in Paris (CRBIP). Type TA 98 demonstrates frameshift mutations (reading frame shifts), type TA 100 serves to detect mutations caused by substitution of the base pairs and type *E. coli* WP2 uvrA detects cross-linking mutagens.

In the arrangement described above, the tested compounds 28, 34 and 51 were non-mutagenous for all of the mentioned bacterial strains and for all of the tested concentrations both using metabolic activation and without this activation. For more information, see FIG. 5; in the same arrangement, the negative control (freely growing bacteria) showed values of 112-133 and the positive controls for −MA I values of >500 (after the application of 1.5 µg of sodium azide) and for +MA I values of >1300 (after the application of 10 µg of 2-aminofluorene).

In Vivo

Under in vivo conditions, the effect of pyrimidine compounds of general formula (I) on adjuvant arthritis with sewer rat albinos (which is the animal model of the human disease of rheumatoid arthritis) and on experimental colitis in mice was tested.

Example 12

Adjuvant Arthritis

Adjuvant arthritis was induced in female sewer rats of the inbred strain Lewis, purchased from AnLab spol. s.r.o., Prague. The animals come from the breeding of laboratory animals of the company Charles River Deutschland (Sulzfeld, Germany). In the accredited laboratory animal facility of the Institute of Experimental Medicine of the ASCR, v.v.i., they were held in translucent breeding terrariums on a bedding of wood shavings in groups of five animals. The lighting regime was 12 hours of dark (6 PM-6 AM)/12 hours of light. The temperature fluctuated in a range of 21-23° C. For the entire time of the experiment, the animals had free access to a pelleted diet and drinking water.

For the experiment, female sewer rats of the inbred strain Lewis were used. Three groups of five animals each were created. The animals in the control group were applied with only Freund's complete adjuvant (FCA); the animals in the second control group were applied with FCA and administered 0.5% methylcelulose (i.e. vehicle), whereas the animals in the experimental group were applied with FCA and administered substance 51.

FCA was comprised of *Mycobacterium tuberculosis* strain H37 Ra (Difco Labs, Detroit, Mich., USA) and paraffin oil (Acros Organics, New Jersey, USA) (0.5 mg/l ml). The suspension was injected subcutaneously in the back left (ipsilateral) paw in a volume of 0.1 ml. The day of the application was marked as "Day 0". The size of the uninjected (the so-called contralateral) paws, which indicates the severity of the arthritic disease, i.e. secondary lesions, was measured with a UgoBasil 7150 plethysmometer (Varese, Italy).

The active substance was prepared as a mild suspension in 0.5% methylcellulose (Methocel 90HG, Lot: 050510BT, Sigma-Aldrich, Prague). The solutions were administered orally using stomach probes, in doses of 50 mg/kg and in a volume of 1 ml/200 g of the weight of the animal. The applications were begun on Day 9, completed on Day 16 after the induction of arthritis. The experiment was completed on Day 19 after the induction of illness.

The effect of the substance was statistically evaluated using variance analysis and subsequently by Bonferroni test. In comparison with the group of control animals, which were administered only methycellulose, a distinctive (statistically significant) reduction of the severity of the illness was observed in the animals that were administered active substance 51. The results are depicted in FIG. 1.

Example 13

Experimental Colitis

The compounds tested were dissolved in 0.5% methylcellulose (MC, Bio-test s.r.o., Konárovice, Czech Republic; Lot: 050510BT) to acquire a final concentration of 2 mg/ml (ca 10 mg/kg). To achieve homogeneity of the suspensions, the substances in MC were disintegrated by ultrasound (sonicated; 20 s, $\lambda$=0.1 µm). Fresh suspensions were prepared every day.

Animals and Arrangement

The female mice of strain BALB/c at 13 weeks old were acquired from the breeding of the Institute of Physiology of the ASCR, v.v.i. Colitis was induced in them by administering a 3% solution (weight/volume) of sodium dextran sulphate (DSS, mol. weight 36-50 kDa; MP Biomedicals, Inc.) in drinking water for a period of seven days [Gastroenterology 98, 694-7, 1990]. Beginning on Day 1 of DSS administration, also a dose of the tested compound, dissolved in 100 µl MC (only a dose of methylcellulose in the case of the control animals), was administered for seven days by stomach probe.

Colitis Severity Assessment

The severity of the colitis was assessed on the last day of the experiment by scoring the clinical activity, histological parameters and measuring the length of the intestine.

Intestine Length

The entire intestine was removed post mortem, without tightening it was placed on a ruler and measured. Shortening of the intestine is an indirect marker of infection (the shorter the intestine, the more serious the infection).

Disease Activity Index

The points of the clinical activity are the sum of the individual assessments from 0 to 4 and were calculated using the following parameters: reduction of body weight (none=0 points, reduction by 1 to 5%=1 point, by 5-10%=2 points, by 10-20%=3 points, by 20%=4 points), consistency of the feces (solid=0 points; not solid, but not sticking to the anus=2 points; liquid, sticking to the anus=4 points) and bleeding (none=0 points, positive Guajak reaction=2 body, strong bleeding=4 points). This point assessment was totaled and divided by three to acquire the overall index of the activity of the disease, which was in a range from 0.0 (a healthy individual) to 4.0 (maximum activity of colitis) as described by Cooper et al. [Lab. Invest. 69, 238-49, 1993].

Histological Assessment

The descending colon was fixed in a buffered solution of 4% formaldehyde and poured into paraffin for the histological assessment. The sections were stained in hematoxylin/eosin. For every sample, four cross cuts were tested, which had been separated from one another by sections of a length of 100 mm. The histological assessment was made for every cut by two pathologists in blind order, which provided an assessment combining the level of the infiltration of leukocytes into the layer of the lamia propria and into the submucosa along with the extent of the damage of the mucous membrane (see Table 1). The overall assessment is the average of the evaluation of the four sections, which was in a range from 0 (no signs of colitis) to 3 (severe colitis).

TABLE 4

Description of the individual histological levels

| Level | Damage | Description |
|---|---|---|
| 0 | norm. mucous membrane | The wall of the small intestine without swelling or infiltration, intestinal crypt without disturbance, well preserved mucus production. |
| 0.5 | borderline | Separate focus infiltration into the crypt bases without mucous membrane disturbance. Appearance also in some of the control animals. |
| 1.0 | mild | Spread of the cellular infiltration into the upper layer of the connective tissue and tela submucosa. Slight swelling of the muscularis mucosae and flattening of the crypts without defects of the epithelium. |
| 1.5 | medium | Concurrence of inflammatory cells and swelling in the muscularis mucosae and irregular infiltrations in the tela submucosa. The membrane is noticeably flat with separated erosions or ulcers, covering less than 10% of the diameter of the intestine. |
| 2.0 | medium to severe | The same as above, but ulcers cover 10-50% of the diameter of the intestine, mostly with suppurative exudate. The crypts are in withdrawal, the production of mucus is suppressed. |
| 2.5 | very severe | The same as above, ulcers cover 50% of the diameter of the intestine. Severe inflammatory infiltration and swelling in the mucous and submucous layers with pseudo-suppurating ulcers and intravascular leukostasis. |
| 3.0 | extreme | The same as above, but with pseudo-total/total denuding of the mucous membrane. |

Statistical Analysis

The differences in the intestinal length, DAI (disease activity index) and histological assessment of multiple groups were compared with the control group (MC/DSS) using a one-way analysis of the differences with a Dunnett test of multiple comparison. The differences were considered as statistically significant at $P<0.05$.

Compounds 28 and 51 were suspended in 0.5% methylcellulose (MC, Bio-test s.r.o., Konárovice, Czech Republic, Lot: 050510BT) to a concentration of 2 mg/ml (approximately 10 mg/kg). Sterile 0.5% MC was used as a placebo and a dose of 40 mg/each administration of 6-thioguanine (6TG) in 0.5% MC as a positive control. The administered suspensions were prepared freshly every other day.

With the application of compounds 28 or 51, a statistically significant reduction of the course of the induced (severe form) experimental colitis in mice took place (see FIG. 2). The therapeutical effect was minimally equal with the effect of 6-TG (a very toxic cancerostatic and immunosuppressant agent, which demonstrates one of the highest activities in this test of the treatment of experimental colitis). The effect of a lower dose of 2.5 mg/kg is not mentioned but had a similar course. It can be said that compounds 28 and 51 in daily, orally administered doses of 2.5 mg/kg or 10 mg/kg protect mice from the severe forms of acute experimental colitis.

Example 14

Chronic Murine Colitis

Chronic colitis was induced in mice (Balb/c) by dextran sulfate sodium (DSS), used as a 3% solution in drinking water. DSS treatment was applied intermittently on the three 5-day intervals, separated by the 9-day intervals (i.e. between the DSS cycles 1/2 and 2/3) during which the mice drunk normal water.

The test compounds were given orally, suspended in 0.5% methylcellulose. The dose was 10 mg/kg. The daily dosing started immediately after the second DSS interval and lasted to the end of the $3^{rd}$ DSS interval, i.e. for the duration of 15 days. At this point, the animals were sacrificed and clinical signs of colitis were examined. Except of continuous monitoring the body weight, the following parameters were evaluated: a) colon length, b) disease activity index, and c) histological grade. Three compounds were included in this experiment: nos. 19, 51, and 28. 5-Aminosalycilic acid was used as a positive reference drug. The effects were compared to the group of mice receiving placebo (0.5% methylcellulose).

The results demonstrate that oral dosing of compound 28 significantly lowers the clinical signs of chronic experimental colitis. Notably, it reduces inflammation in the gut, as shown by the protection against the shortening of colon. The overall disease activity index was lower than in the placebo group. The compound 28 was slightly more effective than the reference drug, i.e. 5-aminosalycilic acid.

Example 15

Chromosomal Aberration Test In Vitro

The clastogenicity potential of compound no. 28 was determined using chromosomal aberration test in vitro. The test was carried out in human peripheral blood lymphocytes both with and without metabolic activation system in two separate assays.

Three concentrations were selected for the test: 0.1, 0.2 and 0.5 mg/ml of final culture. Cells were arrested at metaphase by colchicine, harvested and slides were stained. Metaphase cells were analyzed microscopically for the presence of chromosomal aberrations. A total of 200 well-spread metaphases were examined per concentration on coded slides. Concurrent positive (thiotepa, cyclophosphamide) and negative (2% DMSO) controls were included in each experiment. Under the test conditions used compound n. 28 did not induce an increase in numerical and structural chromosome aberrations in cultured human peripheral blood lymphocytes.

Example 16

Pilot Toxic-Kinetic Study

The study was performed in female rats (Wistar rats) using single per-oral administration and dose of 800 mg/kg of compound n. 28. The plasma samples were taken in intervals during 48 hours. No apparent toxic effect was observed in animals. Plasma samples were prepared by centrifugation (3500 rpm, 10 min, 4° C.), transferred into appropriately labelled and sealed Eppendorf tubes and frozen at −20° C. until transportation to analyses. The plasma was split into two aliquots. All samples were transported in a sufficient amount of dry ice to the analytical laboratory.

The analysis was performed using HPLC/MS/MS method with the use of internal deuterated standard and precipitation separation method. The analytical method used 50 μl of plasma sample for each analysis. The method was validated for concentration as low as 10.0 ng of the compound in 1 ml of plasma. A weighted liner regression was evaluated over the concentration range from 10.0-10 000.0 ng of the compound in 1 ml of plasma. Spiked plasma samples were precipitated with the solution of internal standard. The sample supernatant was analyzed on HPL/MS/MS system TSQ-03.

The main results of the measurements are summarized in the Table 5

TABLE 5

| | |
|---|---|
| $C_{max}$ = maximum concentration | 337.2 ng/ml |
| $T_{max}$ = sampling time of $C_{max}$ | 6.0 hours |
| Terminal elimination rate half-life | 15.9 hours |

Example 16

Effect on Angiogenesis

The supply of nutrient and oxygen to growing solid tumors is allowed by the formation of new blood vessels from pre-existing ones in a complex process termed tumor angiogenesis. Thus, excessive pathological angiogenesis plays an essential role for tumor growth and metastasis and has been identified as an important target for antineoplastic therapy.

Compounds 19, 23, 51 and 53 disrupt in vitro angiogenesis on Matrigel.

Compounds 19, 23, 51 and 53 have been shown to possess antiangiogenic properties using tube formation of human umbilical vein endothelial cells (HUVEC), an in vitro angiogenesis assay considered a model of in vivo capillary development. This so called "Tube Formation Assay" is a method based on the ability of endothelial cells to form capillary-like tubular structures when cultured on Matrigel™ (a gel of basement membrane extract—their natural substrate). The process of capillary-like tube formation includes endothelial cell attachment, migration, and differentiation into tubules. In this experiment, treatment with tested compounds started at the time of seeding HUVEC onto Matrigel and the extent of tubule development was observed after an 8 h time period. Disruption of tube formation was then assessed through observation of the tubular network and direct comparison to solvent-only controls. The quantitative and qualitative measurement of tubular network complexity was performed using web-based S.CORE imaging software and expressed by means of number of tubes, their total length, quality, number of branching points, etc. All these parameters were integrated into "tube formation index" which corresponds to the degree of complexity of tubular network. We observed that compounds 19, 23, 51 and 53 inhibited capillary tube formation in a dose dependent manner. Antiangiogenic activity of compound 23, the most potent one, was apparent from 5 μmol/L concentration and higher. At a 10 μmol/L concentration, compound 23 reduced tube formation by >90%. Compounds 51 and 53 had only limited effect at 10 μmol/L concentration. Cells treated with the same compounds at a 25 μmol/L concentration showed a similar pattern with incomplete tube formation of ~6% and ~46%, respectively. Partial differentiation was observed with compound 19 at 25 μmol/L, whereas, at 10 μmol/L concentration, no inhibitory activity was detectable, resulting in an extensive tubular network after 8 hours. Within this incubation period (8 hours), compounds 19, 23, 51 and 53 did not influence HUVEC cell proliferation in a concentration range of 10 to 50 μmol/L relevant for the tube formation assay (as determined by XTT assay), indicating that the observed effects were not due to antiproliferative effects of these compounds under the experimental conditions. Apoptosis in HUVECs (at ~70% confluency) treated with or without varying concentrations (relevant for the tube formation assay) of tested substances was assessed by a combination of Annexin V and JC-1 staining. After 8 h of these treatments, cells were collected, and the cell population undergoing apoptosis was identified by double-parameter flow cytometry using annexin V and the vital dye propidium iodide (PI). Mitochondrial membrane potential in treated endothelial cells was measured using the lypophilic probe JC-1, which aggregates in healthy mitochondria and fluoresces red, but diffuses in the cytoplasm and fluoresces green upon mitochondrial damage. In both cases, quantification of apoptotic cells were conducted in BD FACSDiva software. As determined by XTT and apoptosis assays, the tested compounds inhibit capillary tube formation in non-toxic concentrations.

The results provide in vitro evidence for antiangiogenic effects of tested substances. Compounds 19, 23, 51 and 53 exert antiangiogenic properties dose-dependently (at physiologically relevant concentrations) that could contribute to their therapeutical potential. We suggest that the mechanism of their antiangio-genic effects on HUVECs is different from inhibition of proliferation and induction of apoptosis. The tube formation ability of endothelial cells was dramatically inhibited by the tested compounds, but their antiangiogenic mechanism at cellular level remains unclear.

III. Physical and Other Characteristics

Example 17

Substances carrying a dimethylaminomethyleneamino group in position 2 of the pyrimidine ring under physiological conditions hydrolyze to the corresponding 2-formamidopyrimidines. This characteristic was demonstrated by monitoring the speed of this conversion using HPLC with a UV detector. The described characteristics can be used for controlled release of active 2-formamidopyrimidines.

The rate of the hydrolysis of substance 19 (in live medium for the in vitro experiments) into substance 51.

Figure 3:
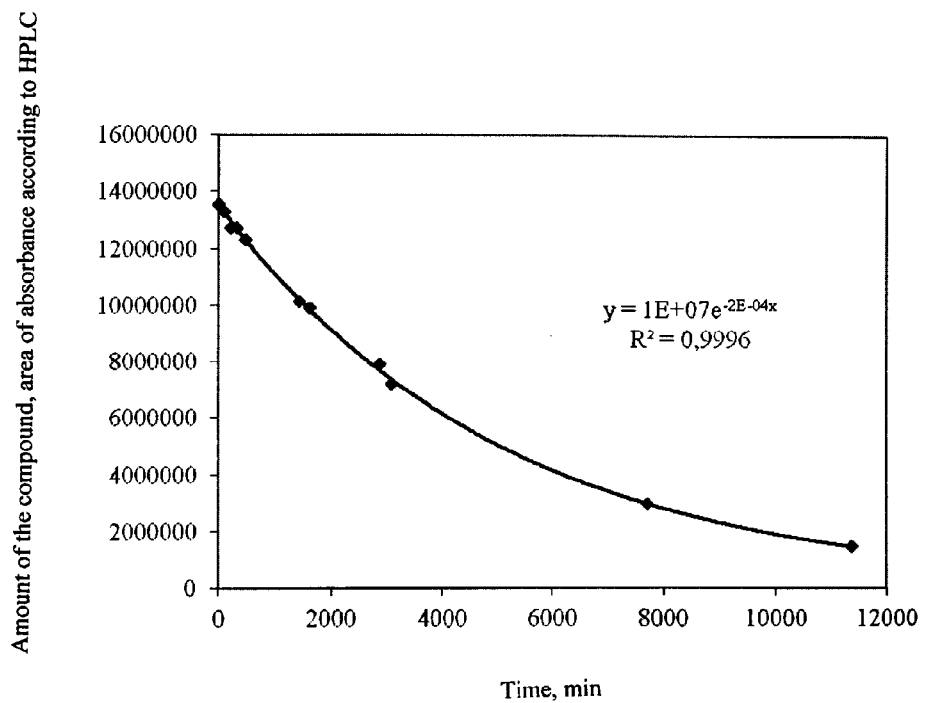
FIG. 3 depicts the speed of the hydrolysis of the compounds according to the invention which bear a dimethylaminomethyleneamino group in position 2 of the pyrimidine ring, into the corresponding 2-formylaminopyrimidines under physiological conditions (a pseudo-first-order reaction). The time in minutes is on the x axis, on the y axis the residual amount of the starting compound determined by measuring the UV absorbance.

The speed of the reaction was observed under pseudo-first-order conditions (these conditions correspond to the concentrations in in vitro tests), see FIG. 3.

After linearization (log(amount of the substance)), a linear dependence with a regressive coefficient of 0.9996 was acquired. From the gradient of the line, the half-time of the conversion of substance 19 into substance 51 was determined as $T_{1/2}$=58.7 hours.

INDUSTRIAL APPLICABILITY

The pyrimidine derivatives according to the present invention simultaneously reduce the production of nitric oxide (NO) and prostaglandin E2, while not having negative effect on the viability of healthy cells in the concentrations in which they reduce the production of these factors by 50%; they are not cytotoxic. They are hence suitable for use for the treatment of diseases that are which are induced or the severity of which is potentiated by the overproduction of NO and/or prostaglandin E2, mainly inflammatory and cancer diseases.

The invention claimed is:

1. A method of treating arthritis or colitis in a subject by administering to the subject a pyrimidine compound of general formula I or a pharmaceutically acceptable salt thereof,

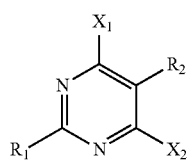

(I)

wherein,
$X_1$ is selected from the group consisting of —Cl, —Br, —I, aryl, and heteroaryl;
$X_2$ is selected from the group consisting of aryl and heteroaryl;
$R_1$ is selected from the group consisting of —H, —NH$_2$, —OH, —SH, and —NHNH$_2$;
$R_2$ is selected from the group consisting of halogen, alkyl, alkenyl, alkynyl, cycloalkyl, and cycloalkenyl,
wherein,
alkyl is a linear or branched $C_1$-$C_{10}$ alkyl chain, wherein alkyl can be unsubstituted or substituted by 1 to 5 substituents selected from the group consisting of —OH, —SH, =NH, =S, halogen, aryl, heteroaryl, —NH$_2$, —CN, —NO$_2$, and —COOR$_d$, wherein R$_d$ is H or $C_1$-$C_6$alkyl;
alkenyl is a linear or branched $C_2$-$C_{10}$ hydrocarbon chain comprising at least one double bond, wherein the alkenyl can be unsubstituted or substituted by 1-5 substituents selected from the group consisting of —OH, —SH, =O, =NH, =S, =N, halogen, —NH$_2$, aryl, heteroaryl, —CN, —NO$_2$, and —COOR$_f$, wherein Rf is H or $C_1$-$C_6$alkyl;
alkynyl is a linear or branched $C_2$-$C_{10}$ hydrocarbon chain comprising at least one triple bond, which can optionally comprise also a double bond, wherein the alkynyl can be unsubstituted or substituted by 1-5 substituents selected from the group consisting of —OH, —SH, =O, =NH, =S, =N, halogen, —NH$_2$, —CN, —NO$_2$, aryl, heteroaryl and —COOR$_h$, wherein Rh is H or $C_1$-$C_6$ alkyl;
cycloalkyl is a $C_3$-$C_{10}$ saturated, carbocyclic ring, which can be unsubstituted or substituted by 1-5 substituents selected from the group consisting of —OH, —SH, =O, =NH, =S, halogen, —NH$_2$, —CN, —NO$_2$, aryl, heteroaryl and —COOR$_j$, where R$_j$ is H or $C_1$-$C_6$ alkyl;
cycloalkenyl is a $C_3$-$C_{10}$ unsaturated, non-aromatic ring, which can be unsubstituted or substituted by 1-5 substituents selected from the group consisting of —OH, —SH, =O, =NH, =S, halogen, —NH$_2$, —CN, —NO$_2$, aryl, heteroaryl and —COOR$_m$, wherein R$_m$ is H or $C_1$-$C_6$ alkyl;
alkoxy is a group —OR$_a$, wherein R$_a$ is a group selected from the group consisting of alkyl, alkenyl, alkynyl, cycloalkyl, and cycloalkenyl as defined above;
alkylthio is a group —SR$_b$, wherein R$_b$ is a group selected from the group consisting of alkyl, alkenyl, alkynyl, cycloalkyl, and cycloalkenyl as defined above;
aryl is phenyl, benzyl, or naphthyl which can be unsubstituted or substituted by 1-5 substituents selected from the group consisting of —OH, —SH, halogen, $C_1$-$C_6$ alkyl, $C_1$-$C_6$ alkoxy, $C_1$-$C_6$ alkylthio, —NH$_2$, —CN, —NO$_2$, and —COOR$_n$, wherein R, is H or $C_1$-$C_6$ alkyl;
heteroaryl is pyrrolyl, furanyl, thiopheneyl, imidazolyl, thiazolyl, oxazolyl, indolyl or pyridinyl, which can be unsubstituted or substituted by 1-5 substituents selected from the group consisting of —OH, —SH, halogen, $C_1$-$C_6$ alkyl, $C_1$-$C_6$ alkoxy, $C_1$-$C_6$ alkylthio, —NH$_2$, —CN, NO$_2$, and —COOR$_p$, wherein R$_p$ is H or $C_1$-$C_6$ alkyl;
halogen is selected from the group consisting of —F, —Cl, —Br, and —I;

provided that X₁ and/or X₂ are not unsubstituted or substituted indole bound directly to the pyrimidine ring by the position 3 of the indole ring.

2. The method of claim 1, wherein the pyrimidine compound of general formula I is selected from the group consisting of:

2-amino-5-butyl-6-chloro-4-phenylpyrimidine;
2-amino-5-butyl-4-chloro-6-(pyridin-3-yl)pyrimidine;
2-amino-5-butyl-4-chloro-6-(pyridin-4-yl)pyrimidine;
2-amino-5-butyl-4-chloro-6-(4-chlorophenyl)pyrimidine;
2-amino-5-butyl-4-chloro-6-(4-nitrophenyl)pyrimidine;
2-amino-5-butyl-4-chloro-6-(4-fluorophenyl) pyrimidine;
2-amino-5-butyl-4-chloro-6-(4 methoxyphenyl)pyrimidine;
2-amino-5-butyl-4-chloro-6-(perfluorophenyl)pyrimidine;
2-amino-5-butyl-4-chloro-6-(furan-2-yl)pyrimidine;
2-amino-5-butyl-4-chloro-6-(furan-3-yl)pyrimidine;
2-amino-5-butyl-4-chloro-6-(thiophenee-3-yl)pyrimidine;
2-amino-5-butyl-4-chloro-6-(thiophenee-2-yl)pyrimidine;
2-amino-5-butyl-4-chloro-6-(1H-pyrrol-2-yl)pyrimidine;
2-amino-5-butyl-4-chloro-6-(1H-pyrrol-3-yl)pyrimidine;
2-amino-5-butyl-4-chloro-6-(1H-imidazol-4-yl)pyrimidine;
2-amino-5-butyl-4-chloro-6-(1H-imidazol-2-yl)pyrimidine;
2-amino-4-(benzofuran-2-yl)-5-butyl-6-chloropyrimidine;
2-amino-4-(benzo[b]thiophenee-2-yl)-5-butyl-6-chloropyrimidine;
2-amino-5-butyl-4-chloro-6-(naphthalen-1-yl)pyrimidine;
2-amino-5-benzyl-4-chloro-6-phenylpyrimidine;
2-amino-5-benzyl-4-chloro-6-(pyridin-3-yl)pyrimidine;
2-amino-5-benzyl-4-chloro-6-(pyridin-4-yl)pyrimidine;
2-amino-5-benzyl-4-chloro-6-(4-chlorophenyl)pyrimidine;
2-amino-5-benzyl-4-chloro-6-(4-nitrophenyl)pyrimidine;
2-amino-5-benzyl-4-chloro-6-(4-fluorophenyl)pyrimidine;
2-amino-5-benzyl-4-chloro-6-(perfluorophenyl)pyrimidine;
2-amino-5-benzyl-4-chloro-6-(furan-2-yl)pyrimidine;
2-amino-5-benzyl-4-chloro-6-(furan-3-yl)pyrimidine;
2-amino-5-benzyl-4-chloro-6-(thiophenee-3-yl)pyrimidine;
2-amino-5-benzyl-4-chloro-6-(thiophenee-2-yl)pyrimidine;
2-amino-5-benzyl-4-chloro-6-(1H-pyrrol-2-yl)pyrimidine;
2-amino-5-benzyl-4-chloro-6-(1H-pyrrol-3-yl)pyrimidine;
2-amino-5-benzyl-4-chloro-6-(1H-imidazole-4-yl)pyrimidine;
2-amino-5-benzyl-4-chloro-6-(1H-imidazole-2-yl)pyrimidine;
2-amino-5-butyl-4,6-diphenylpyrimidine;
2-amino-5-butyl-4-(4-fluorophenyl)-6-phenylpyrimidine;
2-amino-5-butyl-4,6-bis(4-fluorophenyl)pyrimidine;
2-amino-5-butyl-4-(4-methoxyphenyl)-6-phenylpyrimidine;
2-amino-5-butyl-4-(4-fluorophenyl)-6-(4-methoxyphenyl)pyrimidine;
2-amino-5-butyl-4,6-bis(4-methoxyphenyl)pyrimidine;
2-amino-5-butyl-4-phenyl-6-(pyridin-2-yl)pyrimidine;
2-amino-5-butyl-4-(4-methoxyphenyl)-6-(pyridin-2-yl)pyrimidine;
2-amino-5-butyl-4-phenyl-6-(pyridin-3-yl)pyrimidine;
2-amino-5-butyl-4-(4-fluorophenyl)-6-(pyridin-3-yl)pyrimidine;
2-amino-5-butyl-4-(4-methoxyphenyl)-6-(pyridin-3-yl)pyrimidine;
2-amino-5-butyl-4,6-bis(pyridin-3-yl)pyrimidine;
2-amino-5-butyl-4-(4-methoxyphenyl)-6-(pyridin-4-yl)pyrimidine;
2-amino-5-butyl-4-(pyridin-3-yl)-6-(pyridin-4-yl)pyrimidine;
2-amino-5-butyl-4-phenyl-6-(thiophenee-2-yl)pyrimidine;
2-amino-5-butyl-4-(4-fluorophenyl)-6-(thiophenee-2-yl)pyrimidine;
2-amino-5-butyl-4-(4-methoxyphenyl)-6-(thiophenee-2-yl)pyrimidine;
2-amino-5-butyl-4-(pyridin-2-yl)-6-(thiophenee-2-yl)pyrimidine;
2-amino-5-butyl-4-(pyridin-3-yl)-6-(thiophenee-2-yl)pyrimidine;
2-amino-5-butyl-4-(pyridin-4-yl)-6-(thiophenee-2-yl)pyrimidine;
2-amino-5-butyl-4,6-bis(thiophenee-2-yl)pyrimidine;
2-amino-5-butyl-4-(furan-2-yl)-6-phenylpyrimidine;
2-amino-5-butyl-4-(4-fluorophenyl)-6-(furan-2-yl)pyrimidine;
2-amino-5-butyl-4-(furan-2-yl)-6-(4-methoxyphenyl)pyrimidine;
2-amino-5-butyl-4-(furan-2-yl)-6-(pyridin-3-yl)pyrimidine;
2-amino-5-butyl-4-(furan-2-yl)-6-(pyridin-4-yl)pyrimidine;
2-amino-5-butyl-4-(furan-2-yl)-6-(thiophenee-2-yl)pyrimidine;
2-amino-5-butyl-4,6-bis(furan-2-yl)pyrimidine;
2-amino-5-butyl-4-(furan-3-yl)-6-phenylpyrimidine;
2-amino-5-butyl-4-(4-fluorophenyl)-6-(furan-3-yl)pyrimidine;
2-amino-5-butyl-4-(furan-3-yl)-6-(4-methoxyphenyl)pyrimidine;
2-amino-5-butyl-4,6-bis(furan-3-yl)pyrimidine;
2-amino-5-butyl-4-phenyl-6-(thiophene-3-yl)pyrimidine;
2-amino-5-butyl-4-(4-fluorophenyl)-6-(thiophene-3-yl)pyrimidine;
2-amino-5-butyl-4-(4-methoxyphenyl)-6-(thiophene-3-yl)pyrimidine;
2-amino-5-butyl-4-(pyridin-3-yl)-6-(thiophene-3-yl)pyrimidine;
2-amino-5-butyl-4-(thiophene-2-yl)-6-(thiophene-3-yl)pyrimidine;
2-amino-5-butyl-4-(furan-2-yl)-6-(thiophene-3-yl)pyrimidine;
2-amino-5-butyl-4-(furan-3-yl)-6-(thiophene-3-yl)pyrimidine;
2-amino-5-butyl-4,6-bis(thiophene-3-yl)pyrimidine;
2-amino-4-(benzofuran-2-yl)-5-butyl-6-phenylpyrimidine;
2-amino-4-(benzofuran-2-yl)-5-butyl-6-(4-methoxyphenyl)pyrimidine;
2-amino-4-(benzofuran-2-yl)-5-butyl-6-(pyridin-2-yl)pyrimidine;
2-amino-4-(benzofuran-2-yl)-5-butyl-6-(pyridin-3-yl)pyrimidine;
2-amino-4-(benzofuran-2-yl)-5-butyl-6-(pyridin-4-yl)pyrimidine;

2-amino-4-(benzofuran-2-yl)-5-butyl-6-(thiophene-2-yl)pyrimidine;
2-amino-4-(benzofuran-2-yl)-5-butyl-6-(furan-2-yl)pyrimidine;
2-amino-4-(benzofuran-2-yl)-5-butyl-6-(furan-3-yl)pyrimidine;
2-amino-4-(benzofuran-2-yl)-5-butyl-6-(thiophene-3-yl)pyrimidine;
2-amino-4,6-bis(benzofuran-2-yl)-5-butylpyrimidine;
2-amino-4-(benzo[b]thiophene-2-yl)-5-butyl-6-(pyridin-2-yl)pyrimidine;
2-amino-4-(benzo[b]thiophene-2-yl)-5-butyl-6-(pyridin-3-yl)pyrimidine;
2-amino-4-(benzo[b]thiophene-2-yl)-5-butyl-6-(pyridin-4-yl)pyrimidine;
2-amino-4-(benzo[b]thiophene-2-yl)-5-butyl-6-(thiophene-2-yl)pyrimidine;
2-amino-4-(benzo[b]thiophene-2-yl)-5-butyl-6-(furan-2-yl)pyrimidine;
2-amino-5-butyl-4-(naphthalen-1-yl)-6-phenylpyrimidine;
2-amino-5-butyl-4-(4-methoxyphenyl)-6-(naphthalen-1-yl)pyrimidine;
2-amino-5-butyl-4-(naphthalen-1-yl)-6-(pyridin-2-yl)pyrimidine;
2-amino-5-butyl-4-(naphthalen-1-yl)-6-(pyridin-3-yl)pyrimidine;
2-amino-5-butyl-4-(naphthalen-1-yl)-6-(pyridin-4-yl)pyrimidine;
2-amino-5-butyl-4-(furan-2-yl)-6-(naphthalen-1-yl)pyrimidine;
2-amino-5-butyl-4-(furan-3-yl)-6-(naphthalen-1-yl)pyrimidine;
2-amino-5-butyl-4-(naphthalen-1-yl)-6-(thiophene-3-yl)pyrimidine;
2-amino-5-butyl-4,6-bis(naphthalen-1-yl)pyrimidine;
2-amino-5-benzyl-4,6-diphenylpyrimidine;
2-amino-5-benzyl-4,6-bis(pyridin-3-yl)pyrimidine; and
2-amino-4,6-bis(benzofuran-2-yl)-5-benzylpyrimidine.

3. The method of claim 1, wherein prior to administration the pyrimidine compound of general formula I or a pharmaceutically acceptable salt thereof is combined with at least one pharmaceutical carrier, excipient and/or diluent.

4. The method of claim 1 wherein,
$X_1$ is Br,
$X_2$ is aryl or heteroaryl,
$R_1$ is $NH_2$, and
$R_2$ is alkyl, alkenyl, alkynyl, cycloalkyl, or cycloalkenyl.

5. The method of claim 1 wherein $R_2$ is selected from the group consisting of halogen, alkyl, alkenyl, and alkynyl.

* * * * *